(12) United States Patent
Abel et al.

(10) Patent No.: US 8,247,424 B2
(45) Date of Patent: *Aug. 21, 2012

(54) FREDERICAMYCIN DERIVATIVES

(75) Inventors: Ulrich Abel, Heidelberg (DE); Werner Simon, Hüffelsheim (DE)

(73) Assignee: Zentopharm GmbH, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/509,066

(22) PCT Filed: Mar. 20, 2003

(86) PCT No.: PCT/EP03/02922
§ 371 (c)(1),
(2), (4) Date: Sep. 24, 2004

(87) PCT Pub. No.: WO03/080582
PCT Pub. Date: Oct. 2, 2003

(65) Prior Publication Data
US 2005/0256066 A1 Nov. 17, 2005

(30) Foreign Application Priority Data

Mar. 26, 2002 (DE) .................................. 102 13 580
Oct. 17, 2002 (DE) .................................. 102 48 451

(51) Int. Cl.
C07D 471/00 (2006.01)
A61K 31/438 (2006.01)
(52) U.S. Cl. ......................................... 514/278; 546/18
(58) Field of Classification Search .................... 546/18; 514/278, 58
See application file for complete search history.

(56) References Cited

U.S. PATENT DOCUMENTS 4,584,377 A 4/1986 Yokoi et al.
4,673,678 A 6/1987 Misra
5,166,208 A 11/1992 Kelly et al.
2005/0153997 A1* 7/2005 Simon et al. .................. 514/278
2005/0215579 A1* 9/2005 Simon et al. .................. 514/278

FOREIGN PATENT DOCUMENTS

JP 61 044868 3/1986

OTHER PUBLICATIONS

Cyclodextrin solubilization of the antibacterial agents . . . Matt Duan et al, 2005.*
Reaction of β- Cyclodextrin with N-2,3-epoxypropylphthalimide. Preparation, Characterisation and Study of a New Substituted Cycloheptaamylose. Effect on Water Solubility of drugs by Raquel Delgado et al. Sep. 1996.*
Releases of Testoseterone from an osmotic pump tablet utilizing (SBE)7m-β-cyclodextrin as both a solubilizing and an osmotic pump agent by Kazuto Okimoto et al. Jul. 1998.*
Dorwald F. A. Side Reactions in Organic Synthesis, 2005, Wiley: VCH, Weinheim p. IX of Preface.*
Dorwald, 2005, Preface, Side reactions in Organic synthesis.*
Dana Warnick-Pickle et al, Fredericamycin, A new antitumor antibiotic. Nov. 1981.*
Wikepedia definition of glucose, 2010.*
Biology, Chapter 4, Carbon and the Molecular Diversity of Life. Functional groups. Campbell Reese, 2002.*
Nakajima Toshiaki, "Novel Frediricamycin A Derivative" Patent Abs. of Japan 10:No. 203. Abstract of JP61044868 (Mar. 4, 1986).
Latham, M.D., et al., "Inhibition of topoisomerases by fredericamycin A," Cancer Chemother Pharmacol 24:167-171 (1989).

* cited by examiner

Primary Examiner — Rita Desai
(74) Attorney, Agent, or Firm — Connolly Bove Lodge & Hutz LLP

(57) ABSTRACT

The invention relates to novel fredericamycin derivatives, to drugs containing said derivatives or the salts thereof, and to the use of the fredericamycin derivatives for treating diseases, especially cancer diseases.

12 Claims, No Drawings

FREDERICAMYCIN DERIVATIVES

RELATED APPLICATIONS

This application is a national stage application (under 35 U.S.C. 371) of PCT/EP03/02922 filed Mar. 20, 2003 which claims benefit to German Application Serial No. 102 48 451.1 filed Oct. 17, 2002 and German Application Serial No. 102 13 580.0 filed Mar. 26, 2002.

The invention relates to novel fredericamycin derivatives, to drugs containing said derivatives or the salts thereof, and to the use of the fredericamycin derivatives for treating diseases, particularly cancer diseases.

Fredericamycin has been isolated 1981 from *Streptomyces griseus*, and demonstrates anti-cancer activity.

Fredericamycin and several fredericamycin derivatives are known.

In Heterocycles 37 (1994) 1893-1912, J. Am. Chem. Soc. 116 (1994) 9921-9926, J. Am. Chem. Soc. 116 (1994) 11275-11286, J. Am. Chem. Soc. 117 (1995) 11839-11849, JP 2000-072752, and in J. Am. Chem. Soc. 123 (2001), various total syntheses of fredericamycin A have been described, some being enantio-selective.

In U.S. Pat. No. 4,673,768, alkali salts of the fredericamycin A are described. In U.S. Pat. No. 4,584,377, fredericamycin derivatives are described, particularly derivatives acylated in ring E and F. In U.S. Pat. No. 5,166,208, fredericamycin derivatives are described as well, particularly derivatives carrying thio and amino substituents in ring F. The derivatives are generated semi-synthetically or fully synthetically.

Surprisingly it was found that fredericamycin derivatives, especially those derivatized in ring A, represent potent drugs. Also, a possibility was found to introduce such residues in ring A semi-synthetically, with which the water solubility and/or the biological effect, the spectrum of action in comparison with fredericamycin, can be significantly increased. Furthermore, an alternative method was found to make fredericamycin and its derivatives water-soluble by generating cyclodextrin inclusion compounds.

The invention relates to novel fredericamycin derivatives with the general Formula Ia or Ib:

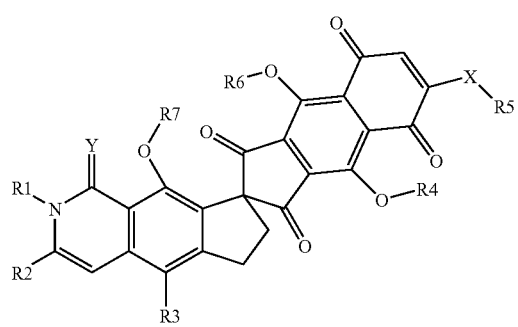

Ia

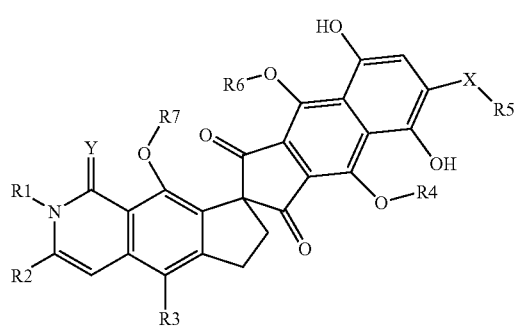

Ib wherein in each,

R1 means H, $C_1$-$C_6$ alkyl, cycloalkyl, $C_1$-$C_4$ alkylcycloalkyl,

R2 means H, $C_1$-$C_{14}$ alkyl, $C_2$-$C_{14}$ alkenyl, aryl, $C_1$-$C_4$ alkylaryl, heteroaryl, $C_1$-$C_4$ alkyl heteroaryl, $C_2$-$C_4$ alkenylheteroaryl, cycloalkyl, $C_1$-$C_4$ alkylcycloalkyl, heterocycloalkyl, $C_1$-$C_4$ alkylheterocycloalkyl, $C_mH_{2m+o-p}Y'_p$ (with m=1 to 6, for o=1, p=1 to 2m+o; for m=2 to 6, o=−1, p=1 to 2m+o; for m=4 to 6, o=−2, p=1 to 2m+o; Y'=independently selected from the group consisting of halogen, OH, OR21, $NH_2$, NHR21, NR21R22, SH, SR21), $(CH_2)_rCH_2NHCOR21$, $(CH_2)_rCH_2OCOR21$, $(CH_2)_rCH_2NHCSR21$, $(CH_2)_rCH_2S(O)_nR21$, with n=0, 1, 2, $(CH_2)_rCH_2SCOR21$, $(CH_2)_rCH_2OSO_2$—R21, $(CH_2)_r$CHO, $(CH_2)_rCH$=NOH, $(CH_2)_rCH(OH)R21$, —$(CH_2)_r$CH=NOR21, $(CH_2)_rCH$=NOCOR21, $(CH_2)_r$CH=NOCH$_2$CONR21R22, $(CH_2)_rCH$=NOCH(CH$_3$)CONR21R22, —$(CH_2)_r$CH=NOC(CH$_3$)$_2$CONR21R22, $(CH_2)_rCH$=N—NHCO—R23, $(CH_2)_rCH$=N—NHC(O)NH—R23, $(CH_2)_rCH$=N—NHC(S)NH—R23, $(CH_2)_rCH$=N—NHC(NH)NH—R23, $(CH_2)_rCH$=N—NHC(NH)—R23, $(CH_2)_1CH$=N—NHCO—CH$_2$NHCOR21, $(CH_2)_rCH$=N—O—CH$_2$NHCOR21, $(CH_2)_rCH$=N—NHCS—R23, $(CH_2)_rCH$=CR24R25 (trans or cis), $(CH_2)_rCOOH$, $(CH_2)_rCOOR21$, $(CH_2)_r$CONR21R22, —$(CH_2)_rCH$=NR21, $(CH_2)_rCH$=N—NR21R22,

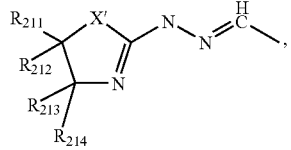

and the $(CH_2)_r$-chain elongated residue $(CH_2)_rCH$=N—N—(C$_3$NX'R211R212R213R214) (with X'=NR215, O, S, and R211, R212, R213, R214, R215 being independently H or $C_1$-$C_6$ alkyl), —$(CH_2)_rCH$=N—NHSO$_2$ aryl, —$(CH_2)_r$CH=N—NHSO$_2$ heteroaryl, with r=0, 1, 2, 3, 4, 5, preferably 0, R21, R22 are independently H, $C_1$-$C_{14}$ alkyl, $C_1$-$C_{14}$ alkanoyl, $C_1$-$C_6$ alkylhydroxy, $C_1$-$C_6$ alkoxy, $C_1$-$C_6$ alkylamino, $C_1$-$C_6$ alkylamino-$C_1$-$C_6$ alkyl, $C_1$-$C_6$ alkylamino-di-$C_1$-$C_6$ alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, mono- and di-sugar residues linked through a C atom which would carry an OH residue in the sugar, wherein the sugars are independently selected from the group consisting of glucuronic acid and its stereo isomers at all optical atoms, aldopentoses, aldohexoses, including their desoxy compounds (as e.g. glucose, desoxyglucose, ribose, desoxyribose), or R21 and R22, together with the N, form a ring with 4, 5, 6, 7, or 8 members, which may optionally contain still another heteroatom selected from the group N, O, S, R23 independently of R21, has the same meanings as R21, or CH$_2$-pyridinium salts, CH$_2$-tri-$C_1$-$C_6$ alkylammonium salts, CONH$_2$, CSNH$_2$, CN, CH$_2$CN, R24 independently of R21, has the same meanings as R21, or H, CN, COCH$_3$, COOH, COOR21, CONR21R22, NH$_2$, NHCOR21, R25 independently of R21, has the same meanings as R21, or H, CN, COCH$_3$, COOH, COOR21, CONR21R22, NH$_2$, NHCOR21, R24, R25 together with the N, form a ring with 4, 5, 6, 7, or 8 members, which may optionally contain still another heteroatom selected from the group N, O, S, R3 means H, F, Cl, Br, I, OH, OR31, NO$_2$, NH$_2$, NHR31, NR31R32, NHCHO, NHCOR31, NHCOCF$_3$, CH$_{3-m}$hal$_m$ (with hal=Cl, F, particularly F, and m=1, 2, 3), OCOR31, R31, R32 are independently C$_1$-C$_6$ alkyl, or R31 and R32, together with the N, form a ring with 4, 5, 6, 7, or 8 members, which may optionally contain still another heteroatom selected from the group N, O, S, R5 means H, C$_1$-C$_{20}$ alkyl, cycloalkyl, C$_2$-C$_{20}$ alkenyl, C$_2$-C$_{10}$ alkinyl, C$_1$-C$_4$ alkyl cycloalkyl, heterocycloalkyl, C$_1$-C$_4$ alkyl heterocycloalkyl, aryl, C$_1$-C$_4$ alkylaryl, heteroaryl, C$_1$-C$_4$ alkylheteroaryl, C$_m$H$_{2m+o-p}$Y'$_p$ (with m=1 to 6, for o=1, p=1 to 2m+o; for m=2 to 6, o=−1, p=1 to 2m+o; for m=4 to 6, o=−2, p=1 to 2m+o; Y'=independently selected from the group consisting of halogen, OH, OR51, NH$_2$, NHR51, NR51R52, SH, SR21), (CH$_2$)$_r$CH$_2$NHCOR51, (CH$_2$)$_r$CH$_2$NHCSR51, (CH$_2$)$_r$CH$_2$S(O)$_n$R51, with n=0, 1, 2, (CH$_2$)$_r$CH$_2$SCOR51, (CH$_2$)$_r$CH$_2$OCOR51, (CH$_2$)$_r$CH$_2$OSO$_2$—R51, (CH$_2$)$_r$CH(OH)R51, (CH$_2$)$_r$COOH, (CH$_2$)$_r$COOR51, (CH$_2$)$_r$CONR51R52, with s=0, 1, 2, 3, 4, 5, preferably 0, mono- and di-sugar residues linked through a C atom which would carry an OH residue in the sugar, wherein the sugars are independently selected from the group consisting of glucuronic acid and its stereo isomers at all optical atoms, aldopentoses, aldohexoses, including their desoxy compounds (as e.g. glucose, desoxyglucose, ribose, desoxyribose), with the mono-sugar residues such as aldopentoses, aldohexoses, including their desoxy compounds (as e.g. glucose, desoxyglucose, ribose, desoxyribose) being preferred, with R51, R52 which are capable of independently adopting the meaning of R21, R22, R4, R6, R7 independently mean H, C$_1$-C$_6$ alkyl, CO—R41, R41 independently from R21, has the same meanings as R21, X means O, S, NH, N—R8, wherein R8 independently from R5 may adopt the same meaning as R5, or R5 and R8, together with the N, form a ring with 4, 5, 6, 7, or 8 members, which may optionally contain still another heteroatom selected from the group N, O, S, or X—R5 may together be H, Y means O, S, NR9, wherein R9 may be H or C$_1$-C$_6$ alkyl, as well their stereoisomers, tautomers, and their physiologically tolerable salts or inclusion compounds, wherein the residues for Formula Ia may not concomitantly adopt the following meaning, except in case of cyclodextrin inclusion compounds: R1: H, C$_1$-C$_6$ alkyl, R2: C$_1$-C$_6$ alkyl, C$_2$-C$_6$ alkenyl, R3: H, R4 and R6 identical, and independently H, C$_1$-C$_6$ alkyl, CO—R41, with R41 being C$_1$-C$_6$ alkyl, aryl, and R7 being H, C$_1$-C$_6$ alkyl, Y: 0, and for Formula Ib: R1: H, R2: pentyl, 1-pentenyl, 3-pentenyl, 1,3-pentdienyl, R3: H, R4 and R6 being H, and X—R5 being methoxy, Y: O. Preferably, the substituents do not concomitantly adopt the following meaning: R1, R3: H, R2: H, alkyl, hydroxyalkyl, particularly monohydroxyalkyl, alkoxyalkyl, CF$_3$, (CH$_2$)$_r$COOH, CHO, CONH$_2$, (CH$_2$)$_r$CH$_2$NHCO alkyl, (CH$_2$)$_r$CH$_2$OCO alkyl, (CH$_2$)$_r$CH$_2$NHCS alkyl, CH=NOH, CH=NO alkyl, aryl, alkylaryl, alkylheteroaryl, alkenyl, hydroxyalkenyl, particularly monohydroxyalkenyl, R4, R6, R7: H, alkyl, X—R5: H, R5: H, alkyl, aryl.

Preferred are compounds of Formula IIa or IIb

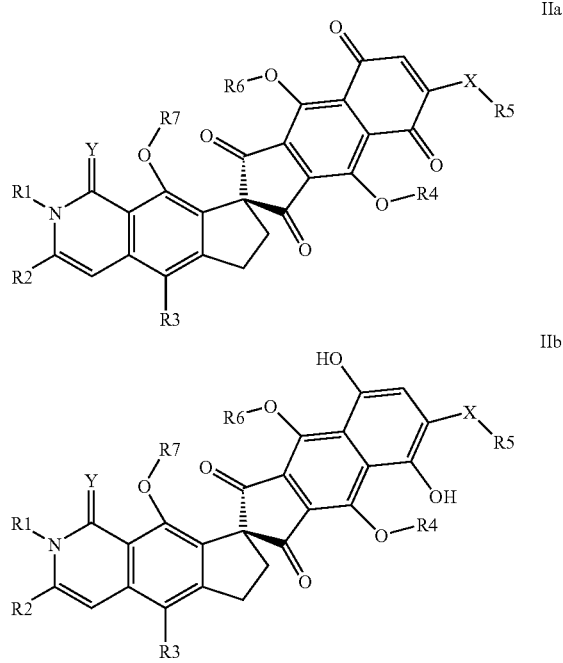

wherein the meaning of the residues R1-R41, X is as described above, their tautomers and their physiologically tolerable salts or inclusion compounds, wherein the residues for Formula Ia may not concomitantly adopt the following meaning, except in the case of cyclodextrin inclusion compounds: R1: H, C$_1$-C$_6$ alkyl, R2: C$_1$-C$_6$ alkyl, C$_2$-C$_6$ alkenyl, R3: H, R4 and R6 identical, and independently H, C$_1$-C$_6$ alkyl, CO—R41, with R41 being C$_1$-C$_6$ alkyl, aryl, and R7 being H, C$_1$-C$_6$ alkyl, Y: O, and for Formula Ib: R1: H, R2: pentyl, 1-pentenyl, 3-pentenyl, 1,3-pentdienyl, R3: H, R4 and R6 being H, and X—R5 being methoxy, Y: O.

The invention further relates to compounds of Formula Ia, Ib, IIa or IIb, in which the residues R, except for R2, have the above described meanings, and the water solubility of R2 is at least two times higher, preferably at least five timer higher, more preferred at least ten times higher, especially preferred at least fifty time higher, particularly one hundred times higher, or even five hundred times higher than of R2 being CH=CH—CH=CH—CH$_3$, when all other residues are maintained. The increase in the water solubility is achieved e.g. by introduction of groups which can form additional hydrogen bonds, and/or are polar, and/or are ionic. A key intermediate are compounds with an aldehyde function in R2.

For R2 preferred is also the group of the residues C$_m$H$_{2m+o-p}$Y'$_p$ (with m=1 to 6, for o=1, p=1 to 2m+o; for m=2 to 6, o=−1, p=1 to 2m+o; for m=4 to 6, o=−2, p=1 to 2m+o; Y'=independently selected from the group of halogen, OH, OR21, NH$_2$, NHR21, NR21R22, SH, SR21), (CH$_2$)$_r$CH$_2$NHCOR21, (CH$_2$)$_r$CH$_2$OCOR21, (CH$_2$)$_r$CH$_2$NHCSR21, (CH$_2$)$_r$CH$_2$S(O)$_n$R21, with n=0, 1, 2, (CH$_2$)$_r$CH$_2$SCOR21, (CH$_2$)$_r$CH$_2$OSO$_2$—R21, (CH$_2$)$_r$CH(OH)R21, (CH$_2$)$_r$COOH, (CH$_2$)$_r$COOR21, (CH$_2$)$_r$CONR21R22. Still particularly preferred is the group of the aldehyde-derived residues (CH$_2$)$_r$CHO, (CH$_2$)$_r$CH=NOH, —(CH$_2$)$_r$CH=NOR21, (CH$_2$)$_r$CH=NOCOR21, (CH$_2$)$_r$CH=NOCH$_2$CONR21R22, (CH$_2$)$_r$CH=N—NHCO—R23, (CH$_2$)$_r$CH=N—NHC(O)NH—R23, (CH$_2$)$_1$CH=N—

NHC(S)NH—R23, $(CH_2)_rCH=N$—NHC(NH)NH—R23, $(CH_2)_rCH=N$—NHC(NH)—R23, $(CH_2)_rCH=N$—NHCO—$CH_2NHCOR21$, $(CH_2)_rCH=N$—O—$CH_2NHCOR21$, $(CH_2)_rCH=N$—NHCS—R23, $(CH_2)_rCH=CR24R25$ (trans or cis), $(CH_2)_rCH=NR21$, $(CH_2)_rCH=N$—NR21R22,

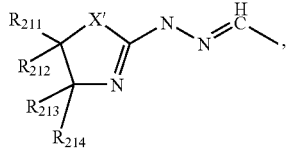

and the $(CH_2)_r$-chain elongated residue $(CH_2)_rCH=N$—N—$(C_3NX'R211R212R213R214)$ (with X'=NR215, O, S, and R211, R212, R213, R214, R215 being independently H or $C_1$-$C_6$ alkyl), —$(CH_2)_rCH=N$—$NHSO_2$ aryl, $(CH_2)_rCH=N$—$NHSO_2$ heteroaryl, $(CH_2)_rCH=CH$ heteroaryl, with r=0, 1, 2, 3, 4, 5, preferably 0.

From the aldehydes and thereof derived compounds, such are preferred in which at least R1 or R3 are not H, if R4 to R7 are H or alkyl.

Preferred residues in R2 are further heteroaryl, cycloaryl, alkylcycloalkyl, heterocycloalkyl, $C_1$-$C_4$ alkyl heterocycloalkyl, $C_mH_{2m+o-p}Y'_p$ (with m=1 to 6, for o=1, p=1 to 2m+o; for m=2 to 6, o=−1, p=1 to 2m+o; for m=4 to 6, o=−2, p=1 to 2m+o; Y'=independently selected from the group of halogen, OH, OR21, $NH_2$, NHR21, NR21R22, SH, SR21), $CH_2NHCOR21$, $CH_2NHCSR21$, $CH_2S(O)_nR21$, with n=0, 1, 2, $CH_2SCOR21$, $CH_2OSO_2$—R21, CH(OH)R21, CH=NOCOR21, —CH=NOCH$_2$CONR21R22, —CH=NOCH(CH$_3$)—CONR21R22, CH=NOC(CH$_3$)$_2$CONR11R22, CH=N—NHCO—R23, —CH=N—NHCO—$CH_2NHCOR21$, CH=N—O—$CH_2NHCOR21$, —CH=N—NHCS—R23, CH=CR24R25 (trans or cis), CONR21R22, —CH=NR21, —CH=N—NR21R22,

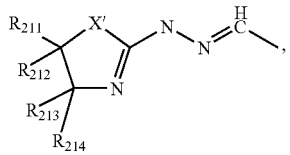

(with X'=NR215, O, S, and R211, R212, R213, R214, R215 being independently H or $C_1$-$C_6$ alkyl), CH=N—$NHSO_2$ aryl, H=N—$NHSO_2$ heteroaryl.

Furthermore, compounds as described above are preferred, in which R3 means F, Cl, Br, I, OH, OR31, $NO_2$, $NH_2$, NHR31, NR31R32, NHCHO, NHCOR31, NHCOCF$_3$, $CH_{3-m}hal_m$ (with hal=Cl, F, particularly F, and m=1, 2, 3), OCOR31, with the above described meanings for R31, R32.

Also preferred are compounds as described above, in which X means N or S, especially when R3 is H or halogen, and/or R2 is alkenyl, particularly butadienyl or 1,3-pentdienyl.

Also preferred are compounds as described above, in which X—R5 is OH, and particularly their salts, and preferred in compounds of Formula Ia or Ia, since this acidic OH group may easily be deprotonized, which increases the water solubility and/or the biological efficacy.

Furthermore preferred are still compounds as described above, wherein the residues R preferably independently adopt one or more of the following meanings:
R1 means H, $C_1$-$C_5$ alkyl, cycloalkyl, especially H,
R2 means $C_1$-$C_5$ alkyl, $C_1$-$C_4$ alkylaryl, $C_2$-$C_5$ alkenyl, heteroaryl, $C_1$-$C_4$ alkylheteroaryl, $C_2$-$C_4$ alkenylheteraryl, CHF$_2$, CF$_3$, polyol side chain, particularly CHOH—CHOH—CHOH—CHOH—CH$_3$, CHOH—CHOH—CH=CH—CH$_3$, CH=CH—CHOH—CHOH—CH$_3$, $CH_2Y'$ (Y'=F, Cl, Br, I), $CH_2NH_2$, $CH_2NR21R22$, $CH_2NHCOR23$, $CH_2NHCSR23$, $CH_2SH$, $CH_2S(O)nR21$, with n=0, 1, 2, $CH_2SCOR21$, particularly $CH_2OH$, $CH_2OR21$, $CH_2OSO_2$—R21, particularly CHO, CH(OR21)$_2$, CH(SR21)$_2$, CN, CH=NOH, CH=NOR21, CH=NOCOR21, CH=N—NHCO—R32, CH=CR24, R25 (trans or cis), particularly COOH (particularly their physiologically tolerable salts), COOR21, CONR21R22, —CH=NR21, —CH=N—NR21R22,

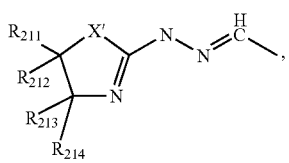

(with X'=NR215, O, S, and R211, R212, R213, R214, R215 being independently H or $C_1$-$C_6$ alkyl), —CH=N—$NHSO_2$ aryl, —CH=N—$NHSO_2$ heteroaryl, CH=N—NHCO—R23, R21, R22 independently mean $C_1$-$C_6$ alkyl, cycloalkyl, aryl, $C_1$-$C_4$ alkylaryl, heteroaryl, $C_1$-$C_4$ alkylheteroaryl, R23 independently of R21, has the same meanings as R21, or $CH_2$-pyridinium salts, $CH_2$-tri-$C_1$-$C_6$ alkylammonium salts, R24 independently of R21, has the same meanings as R21, or H, CN, COCH$_3$, COOH, COOR21, CONR21R22, $NH_2$, NHCOR21, R25 independently of R21, has the same meanings as R21, or H, CN, COCH$_3$, COOH, COOR21, CONR21R22, $NH_2$, NHCOR21, R24, R25 together mean $C_4$-$C_8$ cycloalkyl,
R3 means F, Cl, Br, I, $NO_2$, $NH_2$, NHCOR31,
R31 independently means $C_1$-$C_6$ alkyl,
R5 means H, $C_1$-$C_6$ alkyl, particularly $C_1$-$C_3$ alkyl, $C_3$-$C_8$ cycloalkyl, $C_3$-$C_8$ cycloalkenyl, $C_1$-$C_6$ alkenyl, $C_1$-$C_6$ alkinyls, $C_1$-$C_4$ alkylcycloalkyl, heterocycloalkyl, $C_1$-$C_4$ alkylheterocycloalkyl, aryl, $C_1$-$C_4$ alkylaryl, heteroaryl, $C_1$-$C_4$ alkylheteroaryl, $C_mH_{2m+o-p}Y'_p$ (with m=1 to 6, for o=1, p=1 to 2m+o; for m=2 to 6, o=−1, p=1 to 2m+o; for m=4 to 6, o=−2, p=1 to 2m+o; Y'=independently selected from the group consisting of halogen, OH, OR21, $NH_2$, NHR21, NR21R22, SH, SR21), particularly preferred is hydroxyalkyl with one or more OH groups,
R4, R6, R7 independently means H, $C_1$-$C_5$ alkyl, CO—R41,
R41 independently from R21, has the same meanings as R21,
X means O, S, NH, N—R8,
Y means O, S, NH,
as well their stereoisomers, tautomers, and their physiologically tolerable salts or inclusion compounds, wherein the residues for Formula Ia may not concomitantly adopt the following meaning, except in case of cyclodextrin inclusion compounds: R1: H, $C_1$-$C_6$ alkyl, R2: $C_1$-$C_6$ alkyl, $C_2$-$C_6$ alkenyl, R3: H, R4 and R6 are identical, and independently are H, $C_1$-$C_6$ alkyl, CO—R41, with R41 being $C_1$-$C_6$ alkyl, aryl, and R7 being H, $C_1$-$C_6$ alkyl, and for Formula Ib: R1: H, R2: pentyl, 1-pentenyl, 3-pentenyl, 1,3-pentdienyl, R3: H, R4 and R6 being H, and X—R5 being methoxy.

O, S, particularly O, are preferred for Y.
O, NH, N—R8 are preferred for X.

H, methyl, ethyl, propyl, particularly methyl, are preferred for R5.

H, methyl, ethyl, propyl, particularly methyl, are preferred for R8.

OCH$_3$, NH$_2$, N(CH$_3$)$_2$ are preferred for XR5.

For R2 also preferred is the residue —CHOHCHOHCHOHCHOHCH$_3$.

Furthermore, the following residues are preferred for R2: —CHCH-2-methyl-4-thiazyl, particularly

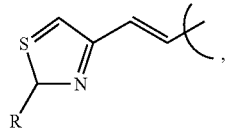

wherein R" particularly is alkyl or NHCO alkyl, CH=NOR21, with R21 being methyl, ethyl, n-propyl, isopropyl, n-butyl, n-hexyl, benzyl, halogen benzyl, particularly fluorobenzyl and chlorobenzyl, —CH$_2$CH$_2$ morpholinyl.

Especially preferred are the compounds, the stereo isomers, tautomers, and physiologically tolerable salts or inclusion compounds of which, selected from the group consisting of the compounds of the examples and the compounds, demonstrate combinations of the various substituents of the examples.

Particularly preferred for R3 is H, F, Cl, Br, J, particularly F, Cl, Br, J.

Particularly preferred for R2 is C$_1$-C$_8$ alkyl, C$_2$-C$_8$ alkenyl, CH=NOR1, with R21 being C$_1$-C$_8$ alkyl, C$_1$-C$_8$ alkenyl, aryl or heteroaryl, C$_1$-C$_2$ alkylaryl, particularly benzyl, C$_1$-C$_2$ alkylheteroaryl, wherein aryl or heteroaryl in particular have only one ring system which may be substituted once or twice with a substituent such as halogen, methyl, CF$_3$, OH, OMe.

Particularly preferred are derivatives of fredericamycin A in which only the above indicated, particularly preferred meanings of R2 and/or R3 are realized.

The invention furthermore relates to drugs containing the above compounds of Formula I or II together with the usual carriers and adjuvants.

Also preferred are the above mentioned drugs in combination with other agents for cancer treatment.

These compounds according to the invention are used for preparation of drugs for treatment of cancers, particularly such that may be treated by inhibition of the topoisomerases I and/or II. Cancers that can be treated with the substances according to the invention are e.g. leukemia, lung cancer, melanomas, uterus tumors, prostate tumors and colon tumors.

Also, fredericamycin A and its derivatives act against an unknown target in the cell cycle leading to apoptosis in tumor cells. Furthermore, the compounds according to the invention, and compounds which have concomitantly adopted the following meanings in Formula Ia: R1: H, C$_1$-C$_6$ alkyl, R2: C$_1$-C$_6$ alkyl, C$_2$-C$_6$ alkenyl, R3: H, R4 and R6 identically and independently H, C$_1$-C$_6$ alkyl, CO—R41, with R41 being C$_1$-C$_6$ alkyl, aryl, and R7 being H, C$_1$-C$_6$ alkyl, and in Formula Ib: R1: H, R2: pentyl, 1-pentenyl, 3-pentenyl, 1,3-pentdienyl, R3: H, R4 and R6 being H and X—R5 being methoxy, are used for preparation of drugs for treatment of neurodermitis, parasites and for immunosuppression.

The invention also relates to a method for preparation of fredericamycin derivatives in which R2 as intermediate is —CHOHCHOHCHOHCHOHCH$_3$. These compounds are preferably transformed into aldehydes for further derivatization.

In the description and the claims, the substituents are described by the following definitions:

The term "alkyl" by itself or as part of another substituent means a linear or branched alkyl chain radical of the respectively indicated length, in which optionally a CH$_2$ group may be substituted by a carbonyl function. Thus, C$_{1-4}$ alkyl may be methyl, ethyl, 1-propyl, 2-propyl, 2-methyl-2-propyl, 2-methyl-1-propyl, 1-butyl, 2-butyl, C$_{1-6}$ alkyl, e.g. C$_{1-4}$ alkyl, pentyl, 1-pentyl, 2-pentyl, 3-pentyl, 1-hexyl, 2-hexyl, 3-hexyl, 4-methyl-1-pentyl, or 3,3-dimethylbutyl.

The term "C$_1$-C$_6$ alkylhydroxy" by itself or as part of another substituent means a linear or branched alkyl chain radical of the respectively indicated length which may be saturated or unsaturated, and which carries an OH group, e.g. hydroxymethyl, hydroxymethyl, 1-hydroxypropyl, 2-hydroxypropyl.

The term "alkenyl" by itself or as part of another substituent means a linear or branched alkyl chain radical with one or more C=C double bonds of the respectively indicated length, several double bonds being preferably conjugated. Thus, C$_{2-6}$ alkenyl may for example be ethenyl, 1-propenyl, 2-propenyl, 2-methyl-2-propenyl, 2-methyl-1-propenyl, 1-butenyl, 2-butenyl, 1,3-butdienyl, 2,4-butdienyl, 1-pentenyl, 2-pentenyl, 3-pentenyl, 1,3-pentdienyl, 2,4-pentdienyl, 1,4-pentdienyl, 1-hexenyl, 2-hexenyl, 1,3-hediexyl, 4-methyl-1-pentenyl, or 3,3-dimethylbutenyl.

The term "alkinyl" by itself or as part of another substituent means a linear or branched alkyl chain radical with one or more C—C triple bonds of the respectively indicated length. Thus, C$_{2-6}$ alkinyl may for example be ethinyl, 1-propinyl, 2-propinyl, 2-methyl-2-propinyl, 2-methyl-1-propinyl, 1-butinyl, 2-butinyl, 1,3-butdiinyl, 2,4-butdiinyl, 1-pentinyl, 2-pentinyl, 3-pentinyl, 1-hexinyl, 2-hexinyl, 4-methyl-1-pentinyl, or 3,3-dimethylbutinyl.

The term "halogen" stands for fluorine, chlorine, bromine, iodine, preferably bromine and chlorine.

The term "NR21R22" preferably stands for a dialkylamino group, wherein the two alkyl groups together with the N can form a ring with 5 or 6 members with optionally one more heteroatom N or O.

The term "cycloalkyl" by itself or as part of another Substituent comprises unsaturated (mono or poly, preferably mono) or saturated, cyclic hydrocarbon groups with 3 to 10 C atoms, preferably 3 to 8 C atoms, such as e.g. cyclopropyl, cyclobutyl, cyclopentyl, cyclohexyl, cyclohex-2-enyl, cyclohex-3-enyl, cyclohex-2,4-dienyl, 4-methylcyclohexyl, 3-methylcyclohexyl, cycloheptyl or cyclooctyl. Saturated cycloalkyls are preferred. The cycloalkyls may be substituted with up to 3 substituents, preferably with up to 1 substituent, wherein the substituents independently can have the meaning C$_1$-C$_6$ alkyl, OH, NO$_2$, CN, CF$_3$, OR11, SH, SR11, C$_1$-C$_6$ alkylhydroxy, C$_1$-C$_6$ alkyl-OR11, COOH, COOR11, NH$_2$, NHR11, NR11R12, halogen, aryl, C$_1$-C$_4$ alkylaryl, heteroaryl, C$_1$-C$_4$ heteroalkylaryl, wherein the residues R11 and R12 independently can mean C$_1$-C$_{10}$ alkyl, cycloalkyl, C$_1$-C$_4$ alkylcycloalkyl.

The term "heterocycloalkyl" by itself or as part of another substituent includes cycloalkyl groups, wherein up to two CH$_2$ groups may be substituted by oxygen, sulfur or nitrogen atoms, and one or two other CH$_2$ groups may be substituted by one or two carbonyl function(s), carbothionyl function(s), or a carbonyl function and a carbothionyl function, for example pyrrolidine, piperidine, morpholine or

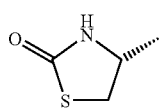 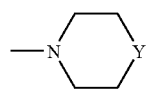

Y = CH$_2$, S, O NH, NC$_1$–C$_6$ alkyl

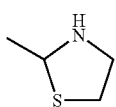

The heterocycloalkyls may be substituted as with the cycloalkyls.

The term "aryl" by itself or as part of another substituent includes aromatic ring systems with up to 3 rings, in which at least 1 ring system is aromatic, and those with up to 3 substituents, preferably up to 1 substituent, wherein the substituents independently can have the meaning $C_1$-$C_6$ alkyl, OH, $NO_2$, CN, $CF_3$, OR11, SH, SR11, $C_1$-$C_6$ alkylhydroxy, $C_1$-$C_6$ alkyl-OR11, COOH, COOR11, $NH_2$, NHR11, NR11R12, halogen, wherein the residues R11 and R12 independently can mean $C_1$-$C_{10}$ alkyl, cycloalkyl, $C_1$-$C_4$ alkylcycloalkyl, or R11 and R12, together with the N, form a ring with 4, 5, 6, 7 or 8 members optionally containing still another heteroatom selected from the group N, O, S.

Apart from phenyl and 1-naphthyl and 2-naphthyl, preferred aryls are:

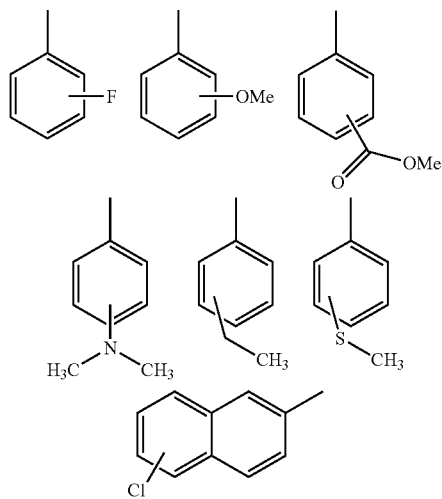

The term "heteroaryl" by itself or as part of another substituent includes aromatic ring systems with up to 3 rings and with up to 3 identical or different heteroatoms N, S, O, in which at least 1 ring system is aromatic, and those with up to 3 substituents, preferably up to 1 substituent, wherein the substituents independently can have the meaning $C_1$-$C_6$ alkyl, OH, $NO_2$, CN, $CF_3$, OR11, SH, SR11, $C_1$-$C_6$ alkylhydroxy, $C_1$-$C_6$ alkyl-OR11, COOH, COOR11, $NH_2$, NHCOR11, NHR11, NR11R12, halogen, or phenyl, wherein the residues R11 and R12 independently can have the above indicated meanings.

Preferred heteroaryls are:

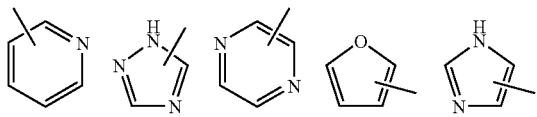

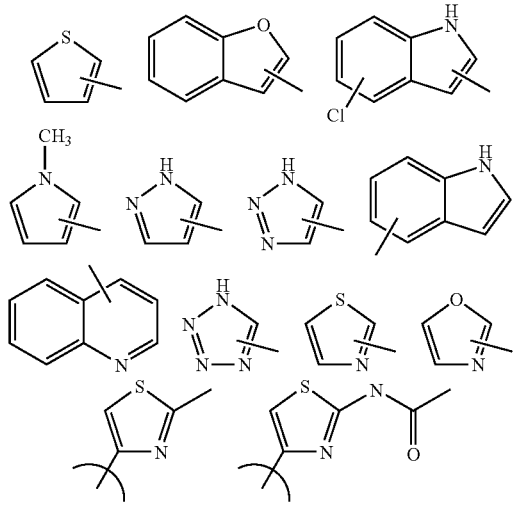

The term "ring system" generally refers to rings with 3, 4, 5, 6, 7, 8, 9, or 10 members. Preferred are rings with 5 and 6 members. Furthermore, ring systems with one or 2 annealed rings are preferred.

The compounds of Formula I may be present as such, or, if they contain acidic or basic groups, in the form of their salts with physiologically tolerable bases or acids. Examples for such acids are: hydrochloric acid, citric acid, trifluoracetic acid, tartaric acid, lactic acid, phosphoric acid, methane sulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid, and acetylglycine. Examples for bases are alkali ions, preferably Na, K, particularly preferred the tri-potassium and tri-sodium salts, alkaline earth ions, preferably C, Mg, ammonium ions.

The compounds according to the invention may be administered orally in the usual way. The application may also be i.v., i.m., with vapors, or sprays through the nasopharynx.

The dosage depends on age, condition and weight of the patient as well as on the type of application. Usually, the daily dose of the active ingredient per person is between 0.1 μg/kg and 1 g/kg orally. This dosage may be given as 2 to 4 split dosages, or once per day as a slow release form.

The novel compounds may be used in the usual solid or liquid pharmaceutical application forms, e.g. as tablets, film tablets, capsules, powder, granules, coated tablets, solutions, or sprays. These are produced in the usual way. The agents can be processed with the usual pharmaceutical adjuvants such as tablet binders, fillers, preservatives, disintegrants, flow regulators, plasticizers, wetting agents, dispersants, emulsifiers, solvents, retardation agents, antioxidants, and/or propellants (see H. Sucker et al.: Pharmazeutische Technologie, Thieme-Verlag, Stuttgart, 1978). Usually, the so obtained application forms contain the active ingredient in amounts of 0.1 to 99 percent per weight.

Experimental Part

Fredericamycin A can be prepared by fermentation or fully synthetically according to the known methods. The reduced forms of the Formulas Ib and IIb can be obtained from the appropriate compounds of Formulas Ia and Ia using mild reducing agents.

Preparation of the Substances

For synthesis of water soluble fredericamycin derivatives, fredericamycin (1) was first hydroxylized with osmium(IV) oxide at the diene side chain. The resulting compound (2) shows significantly higher water solubility compared to the original compound fredericamycin (1). In order to further increase the water solubility, (2) was transformed into the tri-potassium salt (3) (see diagram 1).

Diagram 1

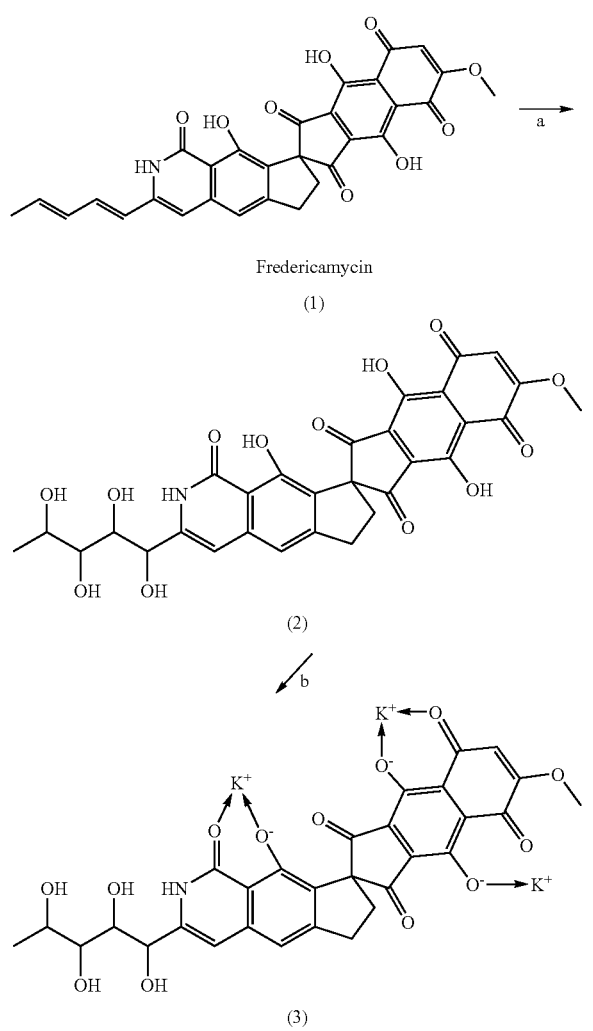

Fredericamycin
(1)

(2)

(3)

a) OsO₄, N-methylmorpholine-N-oxide, CH₂, Cl₂, CH₃OH, H₂O
b) KOH pyridine

The fredericamycin tetrol (2) serves, among others, as an important intermediate for the synthesis of other fredericamycin derivatives with increased solubility and/or better action profile. By iodate cleavage with sodium periodate or carrier-bound periodate, the tetrol side chain may be degraded with very high yields to fredericamycin aldehyde (4) (see diagram 2).

Diagram 2

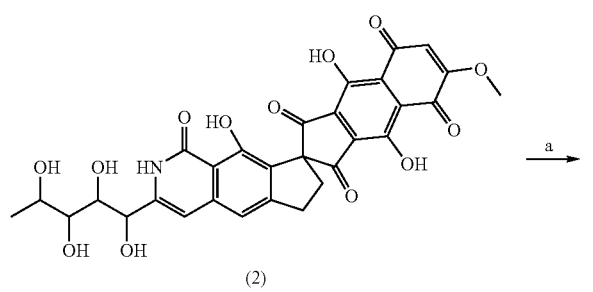

(2)

-continued (4)

a) NaIO₄ — H₂O — DMF or carrier bound — IO₄ — H₂O — DMF

The fredericamycin aldehyde (4) can be reacted with acyl-hydrazones, hydroxylamine, and O-alkylhydroxylamine to the appropriate hydrazone (see diagram 3), or oxime and oximether (see diagram 4). The reaction can be performed at room temperature in solvents such as DMF or pyridine, and is finished after a few minutes to hours.

Synthesis of Hydrazones

Diagram 3

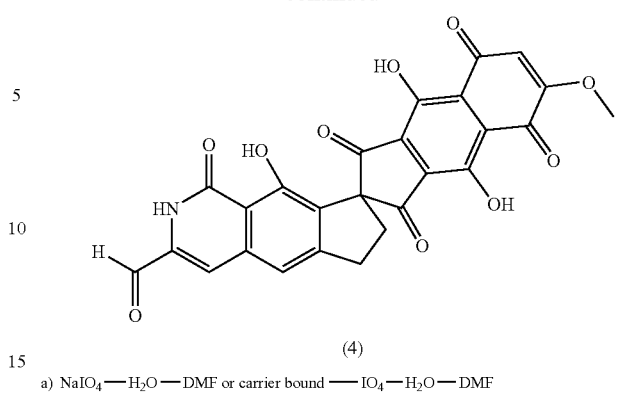

(4)

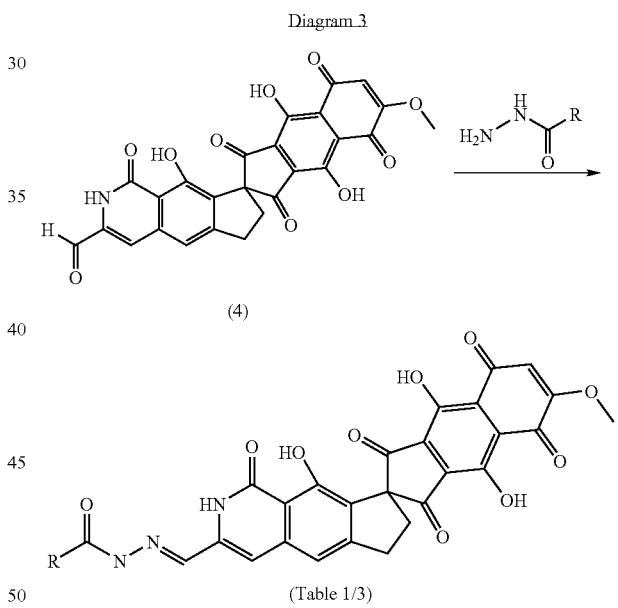

(Table 1/3)

TABLE 1

| Example/compound | R | m/e | $\lambda_{max}$(nm) |
|---|---|---|---|
| 5/118 | ![structure with CF3COO-] | 601.3 | 504.0 |
| 6/119 | ![pyridinium Cl-] | 635.2 | 486.0 |

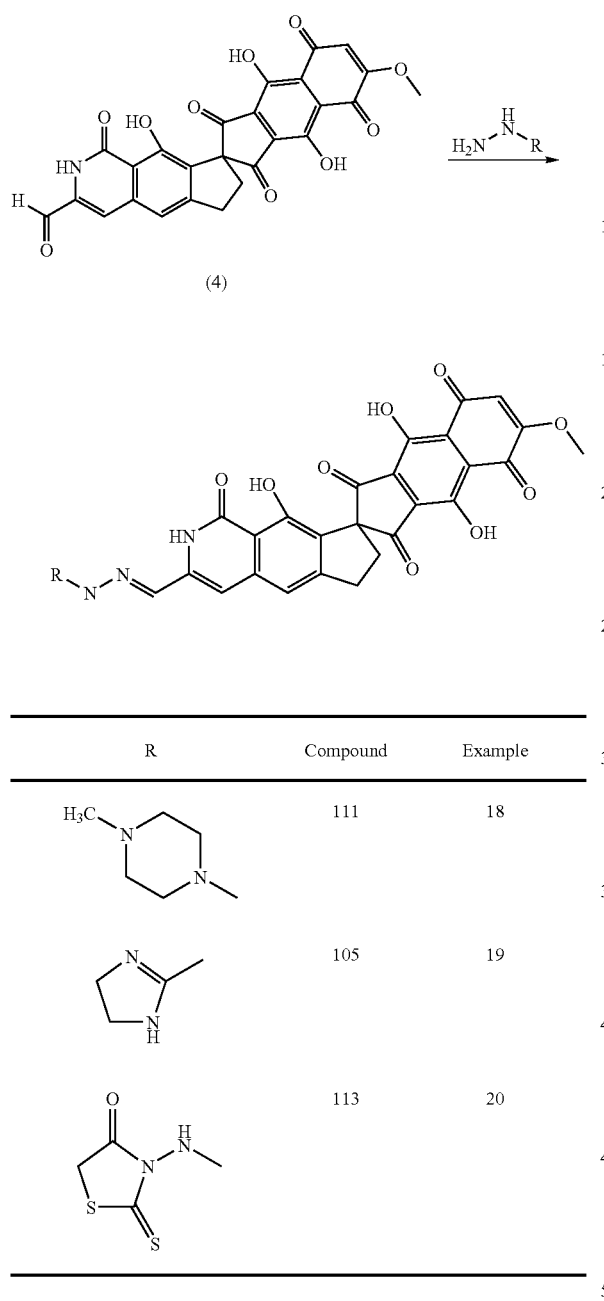

Synthesis of Oximether

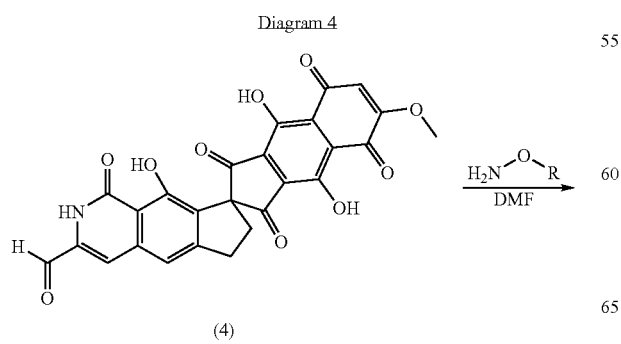

Diagram 4

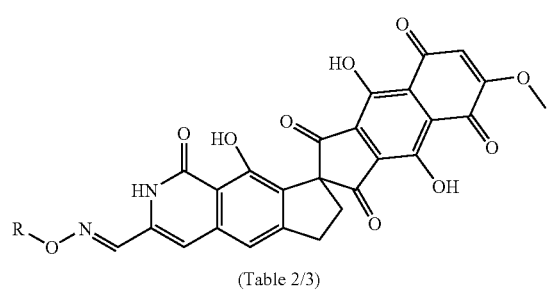

(Table 2/3)

TABLE 2

| Example/compound | R' | m/e | $\lambda_{max}$(nm) |
|---|---|---|---|
| 7/122 | —H | 516.1 | 500.0 |
| 8/120 | —CH₃ | 531.2 | 500.0 |
| 9/121 | benzyl (–CH₂–C₆H₅) | 607.2 | 504.0 |
| 10/123 | deoxy sugar | 678.1 | 504.0 |
| 21/116 | –CH₂CH₂–(tetrahydropyran-4-yl) | 630.1 | 504.0 |

Analogously, the compounds 100-242 can be generated according to the instructions below (table 3). The hereby used hydrazines, hydrazones and hydroxylamines are available commercially, or have been produced according to instructions known from the literature.

Diagram 5
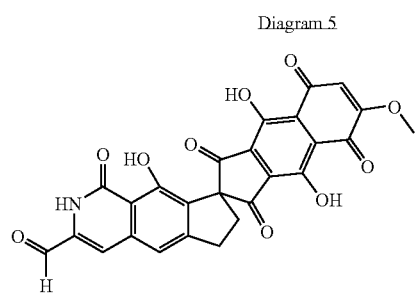
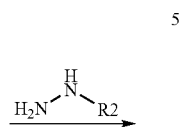
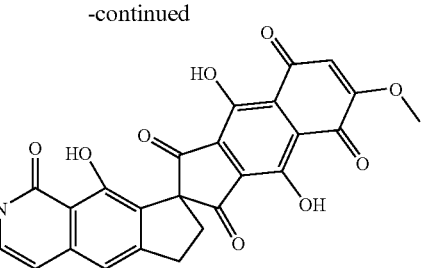
(R1 = Halogen, I, Br, Cl)
TABLE 3
Formula for table 3:
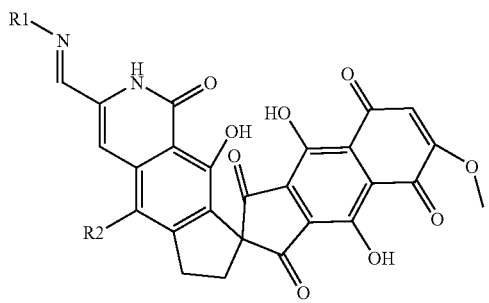
| Example/Compound | R2' | R3 | Calculated mass | Actual mass | UV$_{max}$ | Yield |
|---|---|---|---|---|---|---|
| 100 | (2-pyridyl-NH-C(Me)(Et)(propyl)-) C$_5$H$_5$N$_2$ | 3-pentyl H | 592.1230 | 593.10 | 500 | 95 |
| 101 | (4-CF$_3$-pyrimidin-2-yl-NH-C(Me)(Et)(propyl)-) C$_5$H$_3$F$_3$N$_3$ | 3-pentyl H | 661,1056 | 662,11 | 500 | 95 |
| 102 | (nicotinamido-C(Me)(Et)(propyl)-) C$_6$H$_5$N$_2$O | 3-pentyl H | 620,1179 | 621,11 | 492 | 95 |

TABLE 3-continued

Formula for table 3:

| Example/Compound | R2' | R3 | Calculated mass | Actual mass | UV$_{max}$ | Yield |
|---|---|---|---|---|---|---|
| 103 | (pyridine-carboxamide substituent) C$_6$H$_5$N$_2$O | H | 620,1179 | 621,11 | 500 | 95 |
| 104 | (triazolyl substituent) C$_2$H$_2$N$_3$ | H | 567,1026 | 568,11 | 500 | 80 |
| 105 (19) | (imidazol-2-ylamino substituent) C$_3$H$_6$N$_3$ | H | 583,1339 | 584,10 | 492 | 95 |
| 106 | (furan-2-carboxamide substituent) C$_5$H$_4$NO$_2$ | H | 609,1019 | 610,09 | 492 | 95 |
| 107 | (4-aminobenzamide substituent) C$_7$H$_7$N$_2$O | H | 634,1335 | 635,13 | 492 | 95 |

TABLE 3-continued
Formula for table 3:
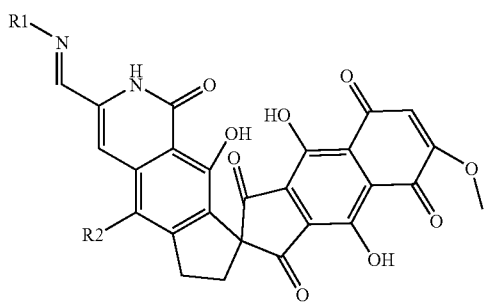
| Example/Compound | R2' | R3 | Calculated mass | Actual mass | UV$_{max}$ | Yield |
|---|---|---|---|---|---|---|
| 108 | H$_2$N-NH-C(=S) (NHCSNH$_2$) | H | 574,0794 | 558,05 | 492 | 95 |
| 109 | thiophene-2-carboxamide (C$_5$H$_4$NOS) | H | 625,0791 | 626,08 | 492 | 95 |
| 110 | indol-3-yl-acetamide (C$_{10}$H$_9$N$_2$O) | H | 672,1492 | 673,15 | 492 | 95 |
| 111 | 4-methylpiperazinyl (C$_5$H$_{11}$N$_2$) | H | 598,1699 | 599,14 | 492 | 95 |
| 112 | H$_2$N-C(=O)-C(=O)-NH (C$_2$H$_3$N$_2$O$_2$) | H | 586,0971 | 587,10 | 492 | 95 |

TABLE 3-continued
Formula for table 3:
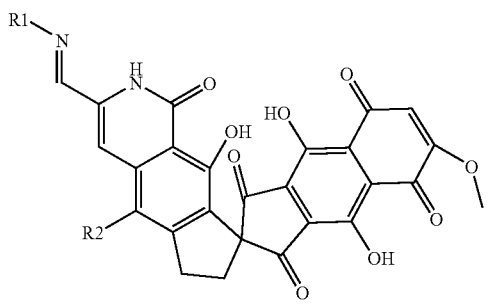
| Example/Compound | R2' | R3 | Calculated mass | Actual mass | $UV_{max}$ | Yield |
|---|---|---|---|---|---|---|
| 113 (20) | (thiazolidinone-thione structure) $C_3H_2NOS_2$ | H | 631,0,55 | 632,05 | 500 | 95 |
| 114 | (cyanoacetamide structure) $C_3H_3N_2O$ | H | 582,1022 | 583,13 | 492 | 95 |
| 115 | (anthranilamide structure) $C_7H_7N_2O$ | H | 634,1335 | 635,16 | 492 | 70 |
| 116 | (morpholinoethoxy structure) $C_6H_{12}NO_2$ | H | 629,1645 | 630,14 | 492 | 85 |
| 117 | (guanidine structure) $CH_4N_3$ | H | 557,1182 | 558,11 | 500 | 95 |

TABLE 3-continued
Formula for table 3:
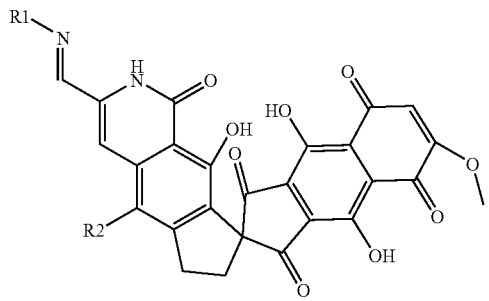
| Example/Compound | R2' | R3 | Calculated mass | Actual mass | UV$_{max}$ | Yield |
|---|---|---|---|---|---|---|
| 118 | C$_4$H$_9$N$_2$O | H | 600,1492 | 601,16 | 492 | 85 |
| 119 | C$_7$H$_8$N$_2$O | H | 635,1414 | 635,13 | 495 | 85 |
| 120 (8) | OMe | H | 530,0961 | 531,12 | 492 | 90 |
| 121 (9) | OCH$_2$Ph | H | 606,1274 | 607,16 | 492 | 95 |
| 122 | OH | H | 516,0804 | 517,11 | 482 | 95 |

TABLE 3-continued

Formula for table 3:

| Example/Compound | R2' | R3 | Calculated mass | Actual mass | UV$_{max}$ | Yield |
|---|---|---|---|---|---|---|
| 123 (10) | (sugar) C$_6$H$_{11}$O$_6$ | H | 678,1332 | 679,14 | 500 | 95 |
| 124 | (phenylurea) C$_7$H$_7$N$_2$O | H | 634,1335 | 635,15 | 492 | 95 |
| 125 | NHCONH$_2$ | H | 558,1022 | 559,12 | 492 | 95 |
| 126 | (piperidinyl acetamide) C$_7$H$_{13}$N$_2$O | H | 640,1805 | 614,13 | 492 | 95 |
| 127 | (3-chlorobenzyloxy) C$_7$H$_6$ClO | H | 640,0884 | 641,10 | 492 | 95 |

TABLE 3-continued
Formula for table 3:
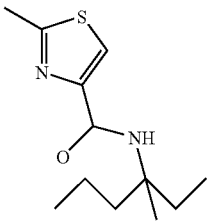
| Example/Compound | R2' | R3 | Calculated mass | Actual mass | $UV_{max}$ | Yield |
|---|---|---|---|---|---|---|
| 128 | 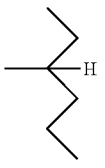<br>$C_5H_5N_2OS$ | 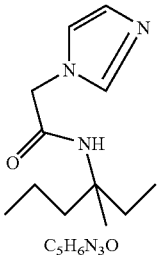<br>H | 640,0900 | 641,10 | 492 | 95 |
| 129 | 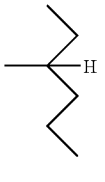<br>$C_5H_6N_3O$ | 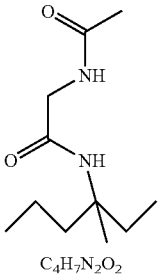<br>H | 623,1288 | 624,13 | 500 | 90 |
| 130 | 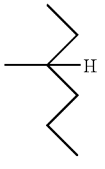<br>$C_4H_7N_2O_2$ | 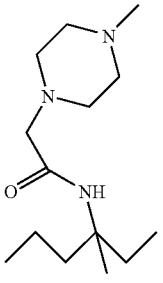<br>H | 614,1284 | 615,13 | 492 | 95 |
| 131 | 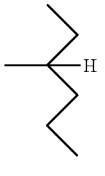<br>$C_7H_{14}N_3O$ | H | 655,1914 | 656,19 | 492 | 50 |

TABLE 3-continued
Formula for table 3:
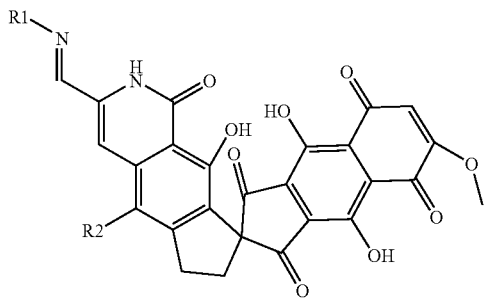
| Example/Compound | R2' | R3 | Calculated mass | Actual mass | $UV_{max}$ | Yield |
|---|---|---|---|---|---|---|
| 132 | (morpholine-acetamide group) $C_6H_{11}N_2O_2$ | H | 642,1597 | 643,17 | 492 | 60 |
| 133 | $C_3H_7N_2O$ | H | 586,1335 | 587,15 | 492 | 70 |
| 134 | $C_6H_{13}N_2O$ | H | 628,1805 | 629,17 | 492 | 70 |
| 135 | $C_4H_{10}NO$ | H | 587,1539 | 588,14 | 492 | 90 |

TABLE 3-continued
Formula for table 3:
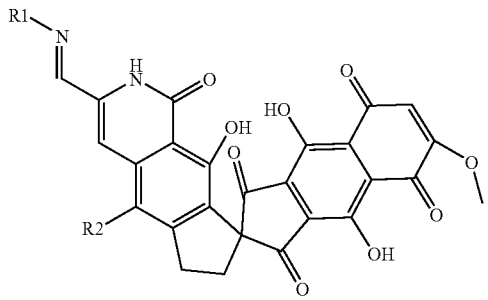
| Example/Compound | R2' | R3 | Calculated mass | Actual mass | UV$_{max}$ | Yield |
|---|---|---|---|---|---|---|
| 136 | 3-chlorophenyl-piperazine-propoxy-tert-alkyl group<br>C$_{13}$H$_{18}$ClN$_2$O | hexan-3-yl, H | 752,1885 | 753,19 | 492 | 85 |
| 137 | dimethylamino-propoxy-tert-alkyl group<br>C$_5$H$_{12}$NO | hexan-3-yl, H | 601,1696 | 602,19 | 492 | 70 |
| 138 | 2-(pyridin-2-ylamino)-alkyl group<br>C$_5$H$_5$N$_2$ | chloro-tert-alkyl, Cl | 626,0840 | 627,07 | 500 | 95 |

TABLE 3-continued
Formula for table 3:
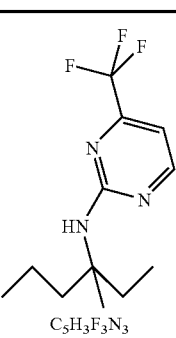
| Example/Compound | R2' | R3 | Calculated mass | Actual mass | UV$_{max}$ | Yield |
|---|---|---|---|---|---|---|
| 139 | 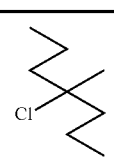<br>C$_5$H$_3$F$_3$N$_3$ | 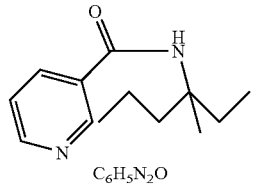 | 695,0666 | 696,06 | 500 | 95 |
| 140 | 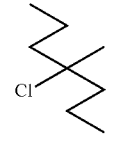<br>C$_6$H$_5$N$_2$O | 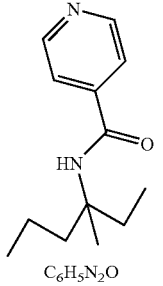 | 654,0789 | 655,07 | 500 | 95 |
| 141 | 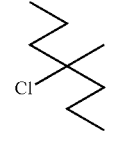<br>C$_6$H$_5$N$_2$O | 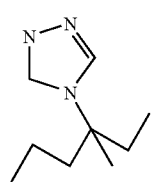 | 654,0789 | 655,07 | 500 | 95 |
| 142 | 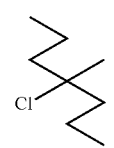<br>C$_2$H$_2$N$_3$ | 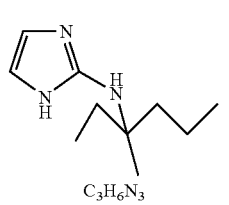 | 601,0636 | 602,06 | 500 | 90 |
| 143 | 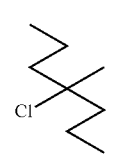<br>C$_3$H$_6$N$_3$ | | 617,0949 | 618,08 | 500 | 95 |

TABLE 3-continued
Formula for table 3:
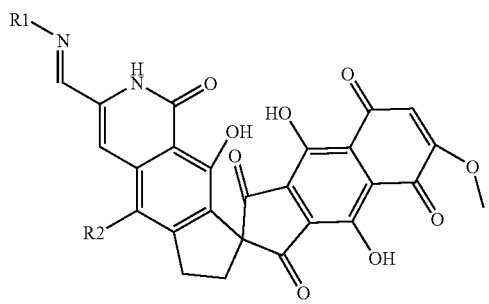
| Example/Compound | R2' | R3 | Calculated mass | Actual mass | UV$_{max}$ | Yield |
|---|---|---|---|---|---|---|
| 144 | C$_5$H$_4$NO$_2$ | Cl | 643,0629 | 644,05 | 500 | 95 |
| 145 | C$_7$H$_7$N$_2$O | Cl | 668,0946 | 669,07 | 500 | 95 |
| 146 | NHCSNH$_2$ | Cl | 608,0404 | 609,07 | 500 | 95 |
| 147 | C$_5$H$_4$NOS | Cl | 659,0401 | 660,07 | 500 | 95 |
| 148 | C$_{10}$H$_9$N$_2$O | Cl | 706,1102 | 707,16 | 500 | 95 |

TABLE 3-continued
Formula for table 3:
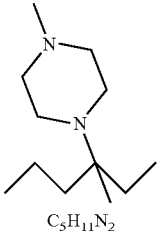
| Example/Compound | R2' | R3 | Calculated mass | Actual mass | UV$_{max}$ | Yield |
|---|---|---|---|---|---|---|
| 149 | 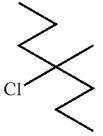<br>C$_5$H$_{11}$N$_2$ | 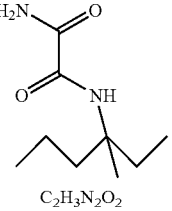<br>Cl | 632,1309 | 633,16 | 500 | 95 |
| 150 | 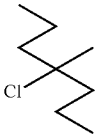<br>C$_2$H$_3$N$_2$O$_2$ | 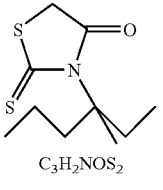<br>Cl | 620,0582 | 621,09 | 500 | 95 |
| 151 | <br>C$_3$H$_2$NOS$_2$ | 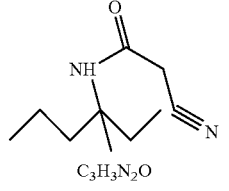<br>Cl | 664,9965 | 645,31 | 500 | 95 |
| 152 | 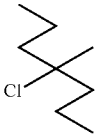<br>C$_3$H$_3$N$_2$O | 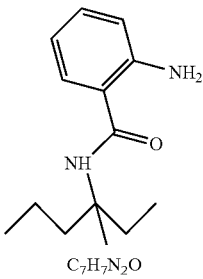<br>Cl | 616,0633 | 617,10 | 500 | 95 |
| 153 | 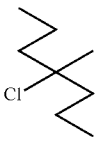<br>C$_7$H$_7$N$_2$O | 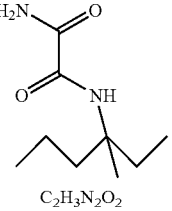<br>Cl | 668,0946 | 669,13 | 500 | 95 |

TABLE 3-continued
Formula for table 3:
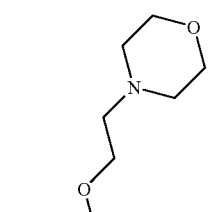
| Example/Compound | R2' | R3 | Calculated mass | Actual mass | $UV_{max}$ | Yield |
|---|---|---|---|---|---|---|
| 154 | 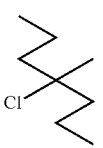<br>$C_6H_{12}NO_2$ | 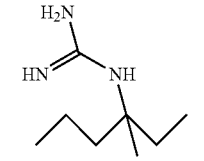<br>Cl | 663,1255 | 664,16 | 500 | 95 |
| 155 | 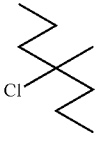 | 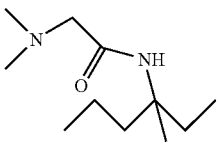 | 591,0792 | 592,11 | 500 | 95 |
| 156 | 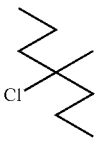<br>$C_4H_9N_2O$ | 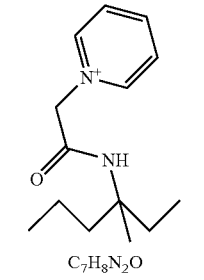<br>Cl | 634,1102 | 635,14 | 500 | 95 |
| 157 | 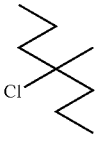<br>$C_7H_8N_2O$ | 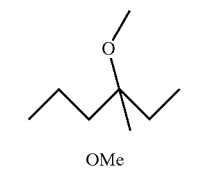<br>Cl | 669,1024 | 669,12 | 500 | 95 |
| 158 | 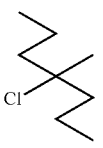<br>OMe | Cl<br>Cl | 564,0571 | 565,09 | 500 | 95 |

TABLE 3-continued
Formula for table 3:
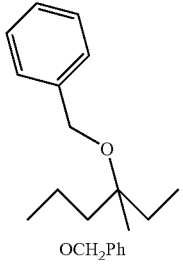
| Example/Compound | R2' | R3 | Calculated mass | Actual mass | UV$_{max}$ | Yield |
|---|---|---|---|---|---|---|
| 159 | 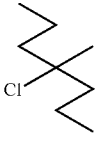<br>OCH$_2$Ph | 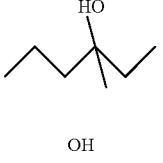<br>Cl | 640,0884 | 641,12 | 500 | 95 |
| 160 | 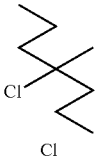<br>OH | 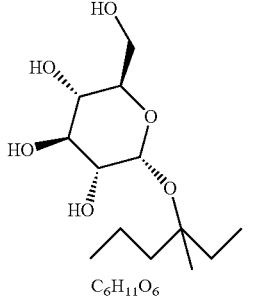<br>Cl | 550,0415 | 551,06 | 500 | 95 |
| 161 | 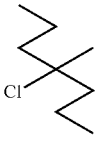<br>C$_6$H$_{11}$O$_6$ | 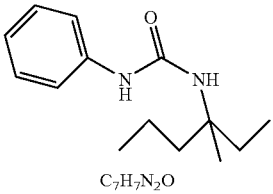<br>Cl | 712,0943 | 713,10 | 500 | 95 |
| 162 | 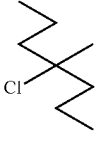<br>C$_7$H$_7$N$_2$O | 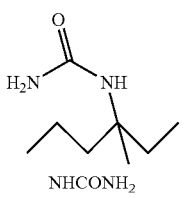<br>Cl | 668,0946 | 669,09 | 500 | 95 |
| 163 | <br>NHCONH$_2$ | Cl | 592,0633 | 593,07 | 500 | 90 |

TABLE 3-continued
Formula for table 3:
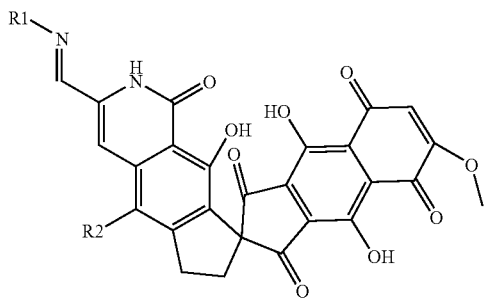
| Example/Compound | R2' | R3 | Calculated mass | Actual mass | UV$_{max}$ | Yield |
|---|---|---|---|---|---|---|
| 164 | piperidinyl-CH$_2$-C(=O)-NH- (C$_7$H$_{13}$N$_2$O) | Cl, Cl (alkyl) | 674,1415 | 675,11 | 500 | 95 |
| 165 | 3-Cl-C$_6$H$_4$-CH$_2$-O- (C$_7$H$_6$ClO) | Cl, Cl (alkyl) | 674,0494 | 675,03 | 500 | 90 |
| 166 | 2-methylthiazol-4-yl-C(=O)-NH- (C$_5$H$_5$N$_2$OS) | Cl, Cl (alkyl) | 674,0510 | 675,02 | 500 | 95 |
| 167 | imidazol-1-yl-CH$_2$-C(=O)-NH- (C$_5$H$_6$N$_3$O) | Cl, Cl (alkyl) | 657,0898 | 658,06 | 500 | 95 |

TABLE 3-continued
Formula for table 3:
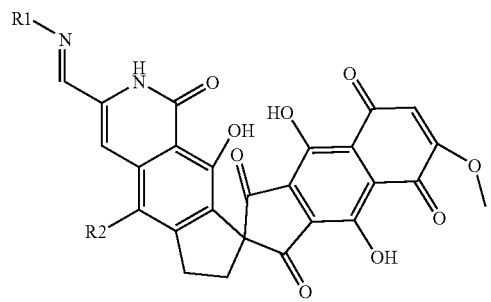
| Example/Compound | R2' | R3 | Calculated mass | Actual mass | UV$_{max}$ | Yield |
|---|---|---|---|---|---|---|
| 168 | (structure) C$_4$H$_7$N$_2$O$_2$ | Cl | 648,0895 | 649,07 | 500 | 95 |
| 169 | (structure) C$_7$H$_{14}$N$_3$O | Cl | 689,1524 | 690,15 | 500 | 60 |
| 170 | (structure) C$_6$H$_{11}$N$_2$O$_2$ | Cl | 676,1208 | 677,13 | 500 | 60 |
| 171 | (structure) C$_3$H$_7$N$_2$O | Cl | 620,0946 | 621,11 | 500 | 70 |

TABLE 3-continued
Formula for table 3:
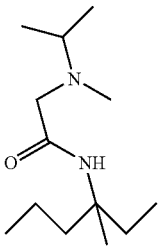
| Example/Compound | R2' | R3 | Calculated mass | Actual mass | $UV_{max}$ | Yield |
|---|---|---|---|---|---|---|
| 172 | 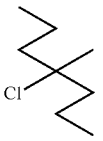<br>$C_6H_{13}N_2O$ | 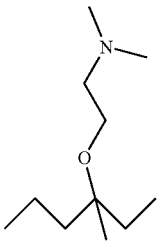<br>Cl | 662,1415 | 663,12 | 500 | 70 |
| 173 | 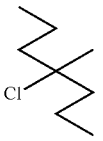<br>$C_4H_{10}NO$ | 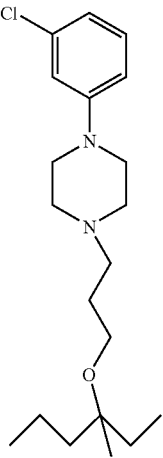<br>Cl | 621,1150 | 622,10 | 500 | 60 |
| 174 | 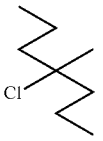<br>$C_{13}H_{18}ClN_2O$ | 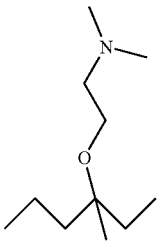<br>Cl | 786,1495 | 787,16 | 500 | 90 |

TABLE 3-continued
Formula for table 3:
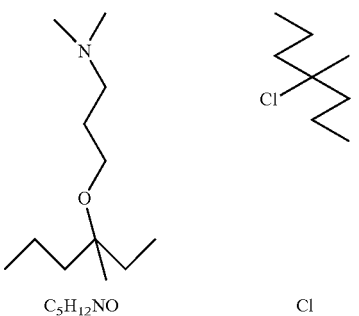
| Example/Compound | R2' | R3 | Calculated mass | Actual mass | UV$_{max}$ | Yield |
|---|---|---|---|---|---|---|
| 175 | <br>C$_5$H$_{12}$NO | 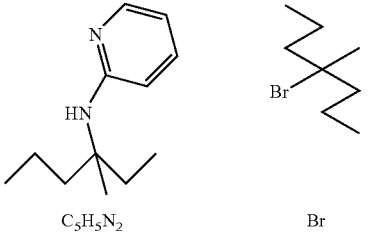<br>Cl | 635,1306 | 636,10 | 500 | 75 |
| 176 | 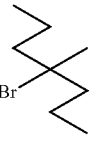<br>C$_5$H$_5$N$_2$ | 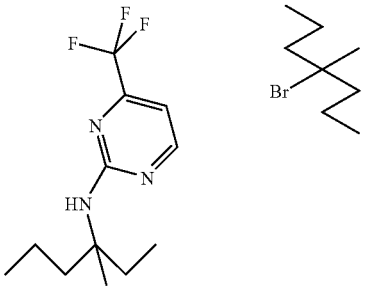<br>Br | 670,0334 | 670,99 | 500 | 95 |
| 177 | 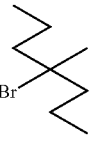 | 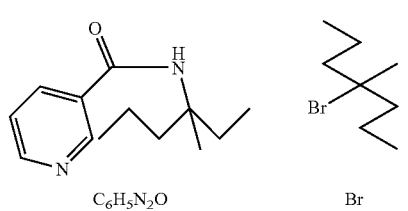 | 739,0161 | 739,99 | 500 | 95 |
| 178 | 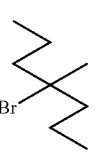<br>C$_6$H$_5$N$_2$O | Br | 698,0284 | 699,00 | 500 | 90 |

TABLE 3-continued
Formula for table 3:
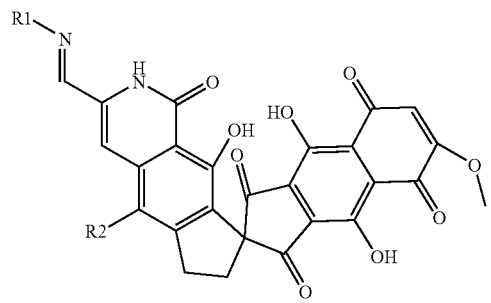
| Example/Compound | R2' | R3 | Calculated mass | Actual mass | UV$_{max}$ | Yield |
|---|---|---|---|---|---|---|
| 179 | (pyridine-C(O)NH-C(CH3)(Et)(Pr)) C$_6$H$_5$N$_2$O | Br-C(CH3)2-C(CH3)2- Br | 698,0284 | 699,00 | 500 | 90 |
| 180 | (1,2,4-triazol-4-yl)-C(CH3)(Et)(Pr) C$_2$H$_2$N$_3$ | Br-C(CH3)2-C(CH3)2- Br | 645,0130 | 645,99 | 492 | 70 |
| 181 | (imidazol-2-yl-NH)-CH(CH3)(Pr) C$_3$H$_6$N$_3$ | Br-C(CH3)2-C(CH3)2- Br | 661,0443 | 662,01 | 492 | 95 |
| 182 | (furan-2-C(O)NH)-C(CH3)(Et)(Pr) C$_5$H$_4$NO$_2$ | Br-C(CH3)2-C(CH3)2- Br | 687,0124 | 688,99 | 492 | 95 |
| 183 | (4-H2N-C6H4-C(O)NH)-C(CH3)(Et)(Pr) C$_7$H$_7$N$_2$O | Br-C(CH3)2-C(CH3)2- Br | 712,0440 | 713,03 | 500 | 95 |

TABLE 3-continued
Formula for table 3:
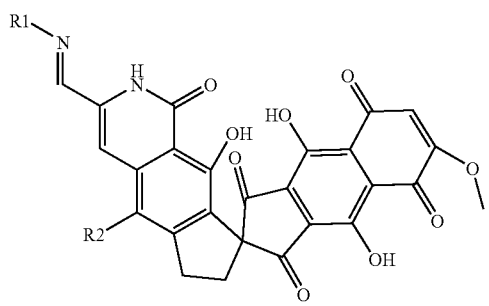
| Example/Compound | R2' | R3 | Calculated mass | Actual mass | $UV_{max}$ | Yield |
|---|---|---|---|---|---|---|
| 184 | H₂N–C(=S)–NH–C(Et)(Pr)– NHCSNH₂ | Br, Br (t-substituted) | 651,9899 | 653,04 | 500 | 95 |
| 185 | thiophene-2-C(=O)–NH–C(Et)(Pr)– C₅H₄NOS | Br, Br | 702,9895 | 704,02 | 492 | 95 |
| 186 | indol-3-yl-CH₂–C(=O)–NH–C(Et)(Pr)– C₁₀H₉N₂O | Br, Br | 750,0597 | 751,10 | 500 | 95 |
| 187 | 4-methylpiperazin-1-yl–C(Et)(Pr)– C₅H₁₁N₂ | Br, Br | 676,0804 | 677,10 | 492 | 95 |
| 188 | H₂N–C(=O)–C(=O)–NH–C(Et)(Pr)– C₂H₃N₂O₂ | Br, Br | 664,0076 | 665,05 | 500 | 95 |

TABLE 3-continued
Formula for table 3:
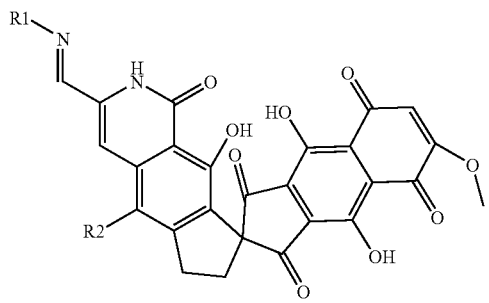
| Example/Compound | R2' | R3 | Calculated mass | Actual mass | UV$_{max}$ | Yield |
|---|---|---|---|---|---|---|
| 189 | (thiazolidinone-thione group) C$_3$H$_2$NOS$_2$ | Br, Br | 708,9460 | 709,99 | 492 | 95 |
| 190 | (cyanoacetamide group) C$_3$H$_3$N$_2$O | Br, Br | 660,0127 | 661,05 | 492 | 95 |
| 191 | (2-aminobenzamide group) C$_7$H$_7$N$_2$O | Br, Br | 712,0440 | 713,08 | 492 | 70 |
| 192 | (morpholinoethoxy group) C$_6$H$_{12}$NO$_2$ | Br, Br | 707,0750 | 708,06 | 500 | 95 |
| 193 | (guanidino group) CH$_4$N$_3$ | Br, Br | 635,0287 | 636,02 | 500 | 95 |

TABLE 3-continued
Formula for table 3:
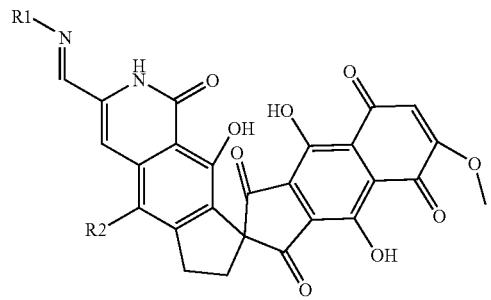
| Example/Compound | R2' | R3 | Calculated mass | Actual mass | UV$_{max}$ | Yield |
|---|---|---|---|---|---|---|
| 194 | C$_4$H$_9$N$_2$O | Br Br | 678,0597 | 679,06 | 500 | 95 |
| 195 | C$_7$H$_8$N$_2$O | Br Br | 713,0518 | 713,03 | 500 | 95 |
| 196 | OMe | Br Br | 608,0066 | 609,03 | 492 | 95 |
| 197 | OCH$_2$Ph | Br Br | 684,0379 | 685,05 | 492 | 95 |
| 198 | OH | Br Br | 593,9909 | 595,01 | 492 | 95 |

TABLE 3-continued

Formula for table 3:

| Example/Compound | R2' | R3 | Calculated mass | Actual mass | UV$_{max}$ | Yield |
|---|---|---|---|---|---|---|
| 199 | (HO-sugar, C$_6$H$_{11}$O$_6$) | Br | 756,0437 | 757,00 | 500 | 90 |
| 200 | (PhNHC(O)NH−, C$_7$H$_7$N$_2$O) | Br | 712,0440 | 713,00 | 500 | 90 |
| 201 | NHCONH$_2$ | Br | 636,0127 | 637,00 | 492 | 90 |
| 202 | (piperidinyl-CH$_2$C(O)NH−, C$_7$H$_{13}$N$_2$O) | Br | 718,0910 | 719,00 | 500 | 90 |
| 203 | (3-Cl-C$_6$H$_4$-CH$_2$-O−, C$_7$H$_6$ClO) | Br | 717,9989 | 718,00 | 492 | 95 |

TABLE 3-continued

Formula for table 3:

| Example/Compound | R2' | R3 | Calculated mass | Actual mass | UV$_{max}$ | Yield |
|---|---|---|---|---|---|---|
| 204 | (2-methylthiazol-4-yl)-C(O)NH-C(CH$_3$)(Et)(propyl)<br>C$_5$H$_5$N$_2$OS | Br-C(CH$_3$)(Et)(propyl) — Br | 718,0004 | 718,97 | 492 | 95 |
| 205 | (imidazol-1-yl)CH$_2$-C(O)NH-C(CH$_3$)(Et)(propyl)<br>C$_5$H$_6$N$_3$O | Br-C(CH$_3$)(Et)(propyl) — Br | 701,0392 | 702,01 | 500 | 95 |
| 206 | CH$_3$C(O)NH-CH$_2$-C(O)NH-C(CH$_3$)(Et)(propyl)<br>C$_4$H$_7$N$_2$O$_2$ | Br-C(CH$_3$)(Et)(propyl) — Br | 692,0389 | 693,03 | 492 | 95 |
| 207 | (4-methylpiperazin-1-yl)CH$_2$-C(O)NH-C(CH$_3$)(Et)(propyl)<br>C$_7$H$_{14}$N$_3$O | Br-C(CH$_3$)(Et)(propyl) — Br | 733,1018 | 734,10 | 500 | 90 |

TABLE 3-continued
Formula for table 3:
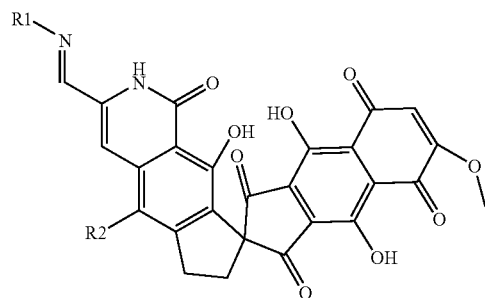
| Example/Compound | R2' | R3 | Calculated mass | Actual mass | $UV_{max}$ | Yield |
|---|---|---|---|---|---|---|
| 208 | (morpholine-acetamide-neopentyl)<br>$C_6H_{11}N_2O_2$ | Br-C(CH3)(C2H5)2<br>Br | 720,0702 | 721,10 | 500 | 95 |
| 209 | (methylamino-acetamide-neopentyl)<br>$C_3H_7N_2O$ | Br-C(CH3)(C2H5)2<br>Br | 664,0440 | 665,08 | 500 | 95 |
| 210 | (N-methyl-N-isopropylamino-acetamide-neopentyl)<br>$C_6H_{13}N_2O$ | Br-C(CH3)(C2H5)2<br>Br | 706,0910 | 707,09 | 500 | 90 |
| 211 | (dimethylaminoethoxy-neopentyl)<br>$C_4H_{10}NO$ | Br-C(CH3)(C2H5)2<br>Br | 665,0644 | 666,08 | 500 | 95 |

TABLE 3-continued
Formula for table 3:
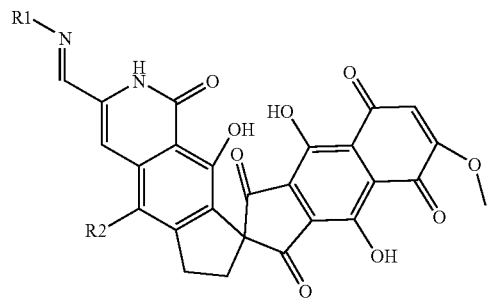
| Example/Compound | R2' | R3 | Calculated mass | Actual mass | $UV_{max}$ | Yield |
|---|---|---|---|---|---|---|
| 212 | 3-Cl-phenyl-piperazine-propyl-O-C(Et)(Me)(Bu) ; $C_{13}H_{18}ClN_2O$ | CMe(Et)(Bu), Br | 830,0989 | 831,11 | 500 | 95 |
| 213 | NMe2-propyl-O-C(Et)(Me)(Bu) ; $C_5H_{12}NO$ | CMe(Et)(Bu), Br | 679,0801 | 680,09 | 492 | 95 |
| 214 | Oi—Pr on C(Et)(Me)(Bu) | CH(Me)(Bu), H | 558,1274 | 559,21 | 500 | 99 |

TABLE 3-continued
Formula for table 3:
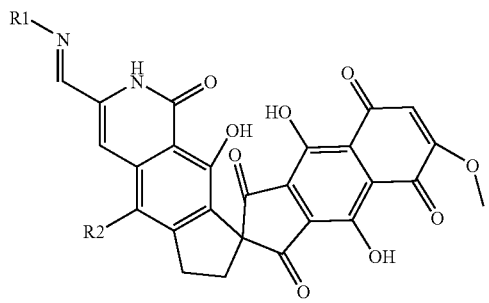
| Example/Compound | R2' | R3 | Calculated mass | Actual mass | $UV_{max}$ | Yield |
|---|---|---|---|---|---|---|
| 215 | O-n-hex | H | 600,1743 | 601,30 | 500 | 99 |
| 216 | $C_7H_6FO$ | H | 624,1180 | 625,28 | 500 | 99 |
| 217 | $C_7H_6ClO$ | H | 640,0884 | 641,27 | 500 | 99 |
| 218 | $C_7H_6FO$ | H | 624,1180 | 625,31 | 500 | 99 |

TABLE 3-continued
Formula for table 3:
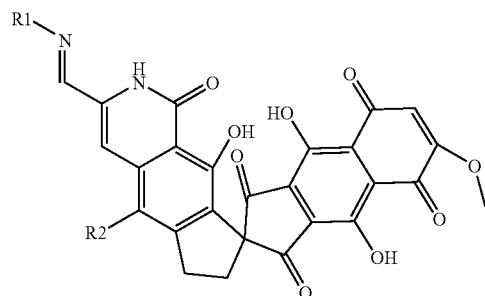
| Example/Compound | R2' | R3 | Calculated mass | Actual mass | $UV_{max}$ | Yield |
|---|---|---|---|---|---|---|
| 219 | Oi—Pr | Cl | 592,0884 | 593,28 | 500 | 80 |
| 220 | O-n-hex | Cl | 634,1354 | 635,36 | 500 | 90 |
| 221 | $C_7H_6FO$ | Cl | 658,0790 | 659,32 | 500 | 85 |
| 222 | $C_7H_6ClO$ | Cl | 674,0494 | 675,31 | 500 | 80 |

TABLE 3-continued
Formula for table 3:
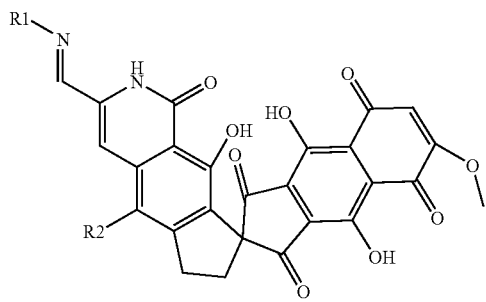
| Example/Compound | R2' | R3 | Calculated mass | Actual mass | UV$_{max}$ | Yield |
|---|---|---|---|---|---|---|
| 223 | C$_7$H$_6$FO | Cl | 658,0790 | 659,34 | 500 | 80 |
| 224 | Oi—Pr | Br | 636,0379 | 639,30 | 492 | 90 |
| 225 | O-n-hex | Br | 678,0848 | 679,37 | 492 | 95 |
| 226 | C$_7$H$_6$FO | Br | 702,0284 | 703,34 | 492 | 95 |

TABLE 3-continued
Formula for table 3:
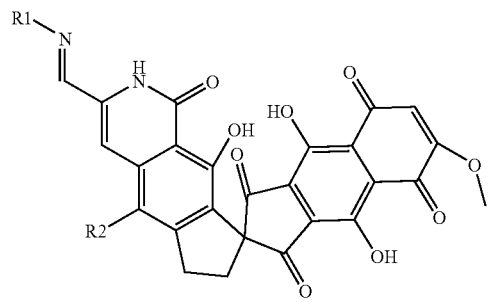
| Example/Compound | R2' | R3 | Calculated mass | Actual mass | $UV_{max}$ | Yield |
|---|---|---|---|---|---|---|
| 227 | 4-Cl-C6H4-CH2-O- (C7H6ClO) | Br-CH2-C(CH3)2-CH2CH3 (Br) | 717.9989 | 719.34 | 492 | 95 |
| 228 | 3-F-C6H4-CH2-O- (C7H6FO) | Br-CH2-C(CH3)2-CH2CH3 (Br) | 702.0284 | 705.35 | 492 | 95 |
| 229 | Oi—Pr | I | 684.0200 | 685.30 | 500 | 99 |
| 230 | O-n-hex | I | 726.0669 | 727.41 | 500 | 99 |

TABLE 3-continued
Formula for table 3:
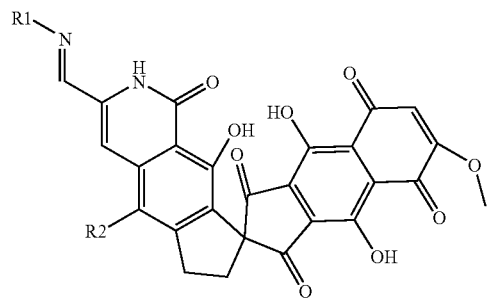
| Example/Compound | R2' | R3 | Calculated mass | Actual mass | $UV_{max}$ | Yield |
|---|---|---|---|---|---|---|
| 231 | C₇H₆FO | I | 750,0105 | 751,38 | 500 | 99 |
| 232 | C₇H₆ClO | I | 765,9810 | 767,36 | 500 | 99 |
| 233 | C₇H₆FO | I | 750,0105 | 751,38 | 500 | 99 |
| 234 | OCH₂Ph | I | 732,0200 | 733,38 | 500 | 99 |

TABLE 3-continued
Formula for table 3:
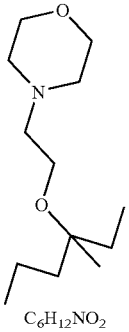
| Example/Compound | R2' | R3 | Calculated mass | Actual mass | UV$_{max}$ | Yield |
|---|---|---|---|---|---|---|
| 235 | 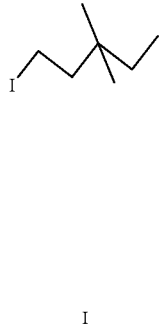<br>C$_6$H$_{12}$NO$_2$ | 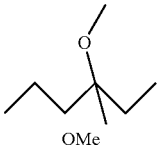<br>I | 755,0571 | 756,33 | 500 | 99 |
| 236 | 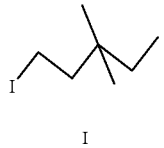<br>OMe | 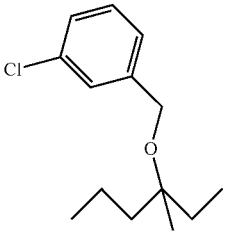<br>I | 655,9887 | 657,32 | 492 | 95 |
| 237 | <br>C$_7$H$_6$ClO | 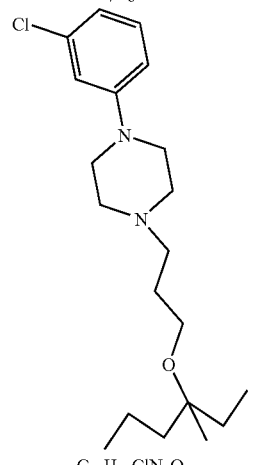<br>I | 765,9810 | 767,38 | 492 | 99 |
| 238 | <br>C$_{13}$H$_{18}$ClN$_2$O | I | 878,0810 | 879,45 | 500 | 99 |

TABLE 3-continued

Formula for table 3:

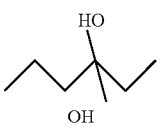

| Example/Compound | R2' | R3 | Calculated mass | Actual mass | UV$_{max}$ | Yield |
|---|---|---|---|---|---|---|
| 239 | 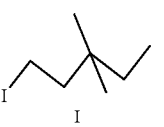 | 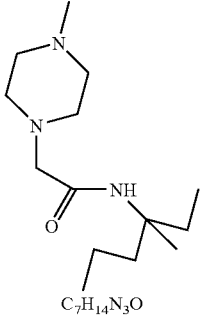 | 641,9730 | 643,31 | 492 | 99 |
| 240 | 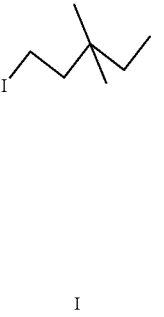  C$_7$H$_{14}$N$_3$O | 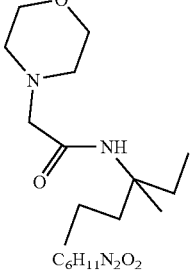  I | 781,0840 | 782,39 | 500 | 99 |
| 241 |   C$_6$H$_{11}$N$_2$O$_2$ | 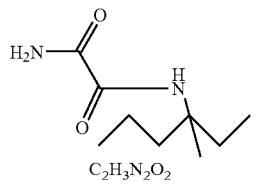  I | 768,0523 | 769,38 | 500 | 99 |
| 242 |   C$_2$H$_3$N$_2$O$_2$ | I | 711.9897 | 713.37 | 500 | 99 |

Reduction and Oxidation of Fredericamycin Aldehyde (4)

Fredericamycin aldehyde (4) can be reacted with a common reducing agent such as sodium borohydrid in a solvent such as DMF or pyridine to hydroxymethyl fredericamycin (11). The reaction can be summarized as a single pot reaction (iodate cleavage of fredericamycin tetrol (2) to fredericamycin aldehyde (4) (see diagram 2) and reduction without isolation of the intermediates to fredericamycin alcohol (11)).

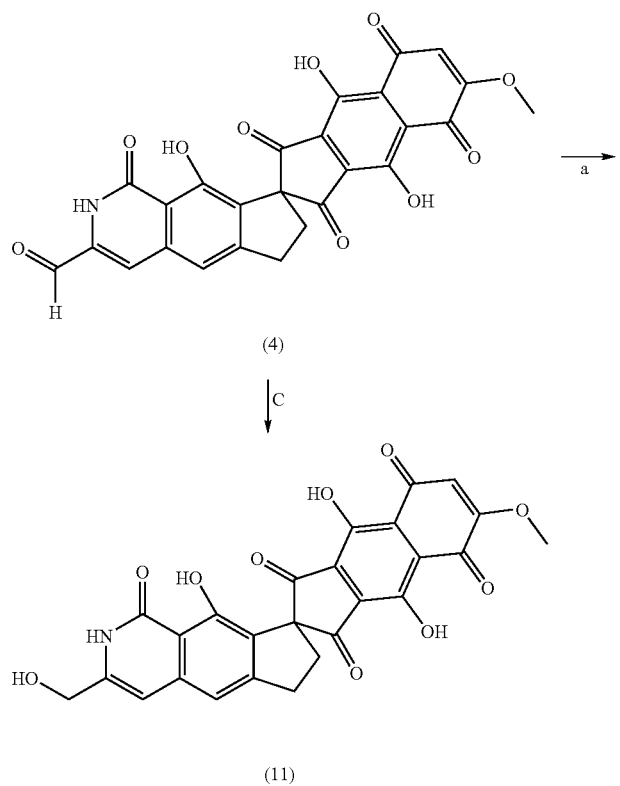
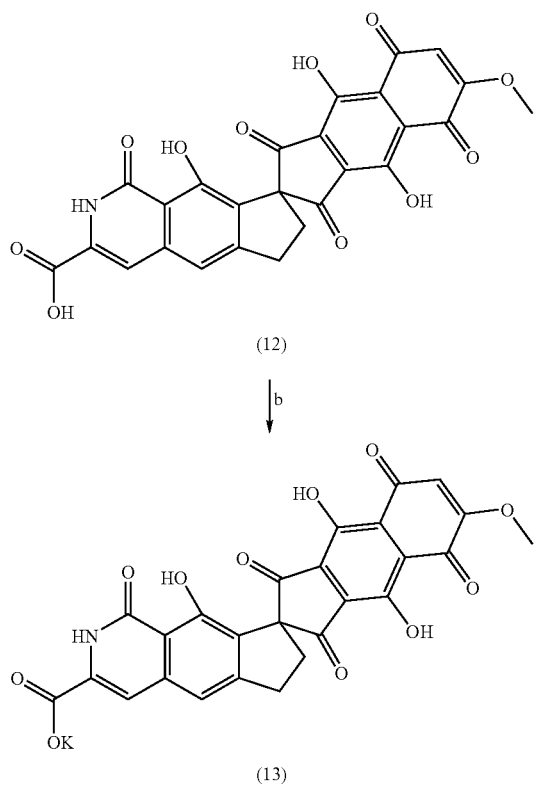

a) NaClO₂, NaH₂, PO₄, 2,3-dimethylbutene-2
b) KOH —— H₂O, DMF
c) NaBH₄

Fredericamycin aldehyde (4) can be oxidized with the oxidizing agent sodium chlorite (NaClO₂), a buffer such as sodium dihydrogenphosphate in presence of an alkene such as 2,3-dimethylbutene with very good yields to fredericamycin carboxylic acid (12). The usually employed oxidation methods such as those being used in preparative chemistry for the oxidation of aldehydes to carboxylic acids (oxidation with chromium(VI) compounds, manganese(VII) compounds as well as peroxo acid) did not lead to success. Only the use of the above described oxidation method provided the desired product. The literature describes oxidations of 2-pyridone-6-aldehydes with silver ions and potassium permanganate in an alkaline medium. This method, however, is not suited for fredericamycin and its derivatives since fredericamycin (1) contains base-labile (-reactive) groups (OH groups) causing undesired side reactions.

The potassium salt of the fredericamycin acid (13) was obtained according to a common method by stoichiometric neutralization.

Substitution in the B Ring

Fredericamycin (1) can be reacted with halogenation agents such as N-bromosuccinimide (NBS) and N-iodosuccinimide (NIS) with good yields to the substituted 5-bromo or 5-iodo fredericamycin derivatives (14) and (15) (diagram 6). The fredericamycin aldehyde (4) and (36) can be transformed with elemental bromine, NBS, BrI, NIS, and NCS to the appropriate halogen-substituted fredericamycin aldehyde (37), (38) and (39).

The appropriate fluorine compound is accessible, too.

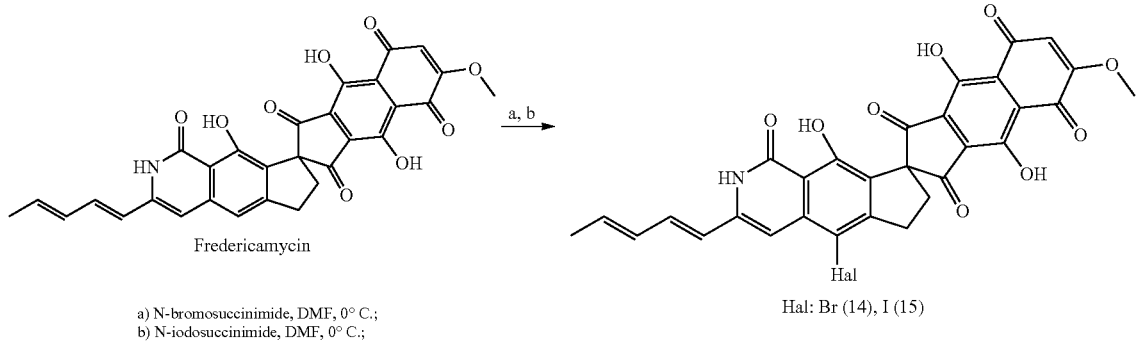

Fredericamycin a) N-bromosuccinimide, DMF, 0° C.;
b) N-iodosuccinimide, DMF, 0° C.;

Hal: Br (14), I (15)

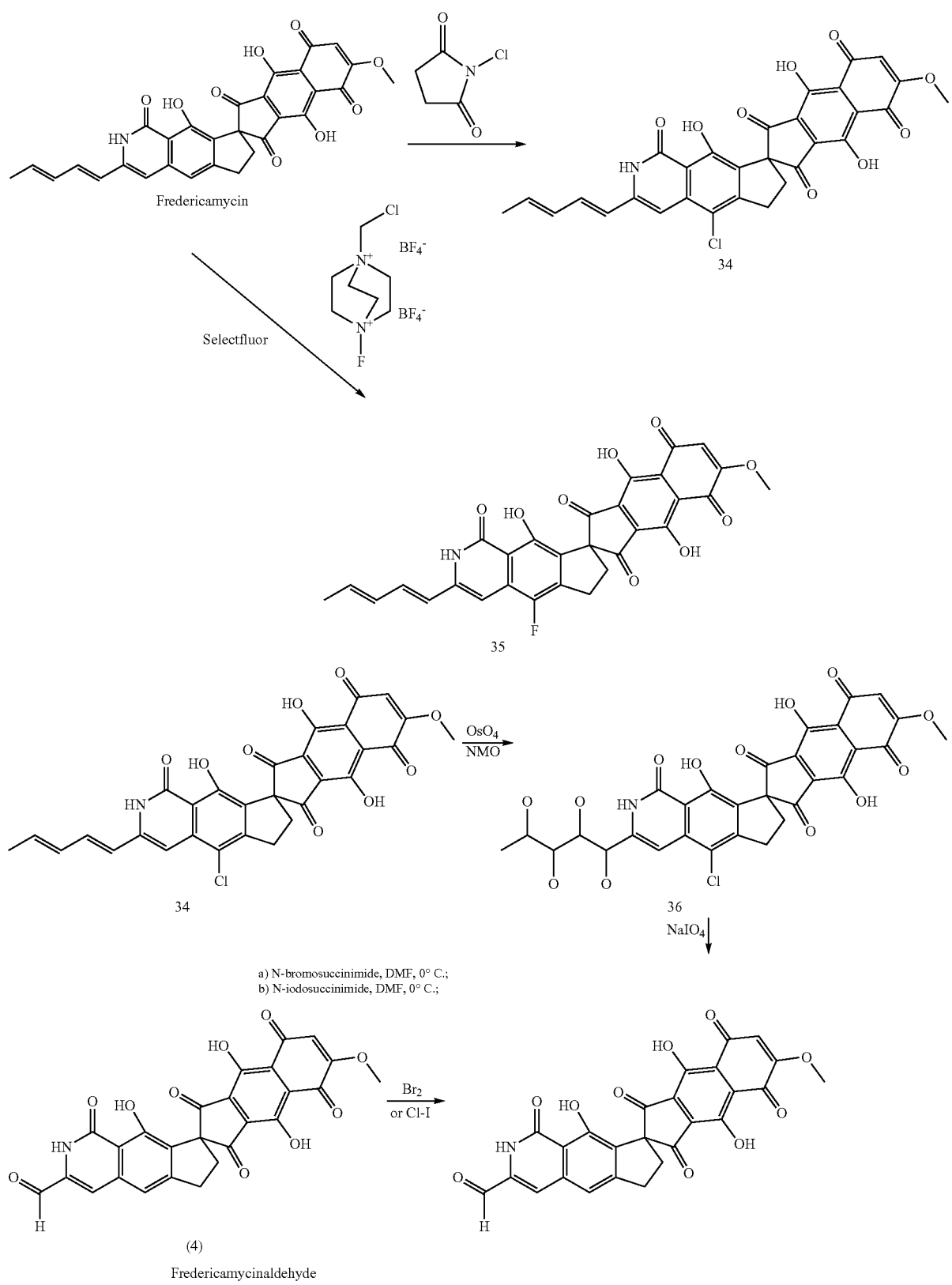
a) N-bromosuccinimide, DMF, 0° C.;
b) N-iodosuccinimide, DMF, 0° C.;
Br: (37)
I: (38)
Cl: (39)

Both of the two following fredericamycin compounds (23) and (24) are also precursors. (23) is the precursor for an amino acid-linked fredericamycin derivative.

The preparation of (23) may be recognized as proof that the aldehyde (4) may be reacted with phosphorylides according to Wittig or Wittig-Horner (see diagram 7).

Diagram 7

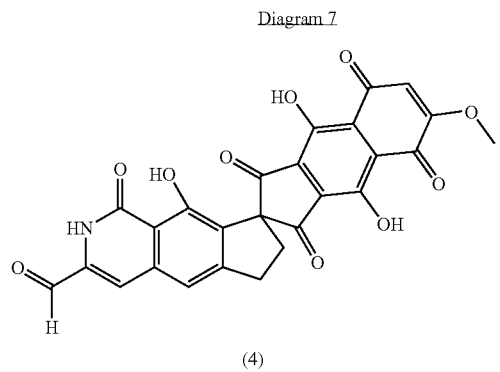

(4)

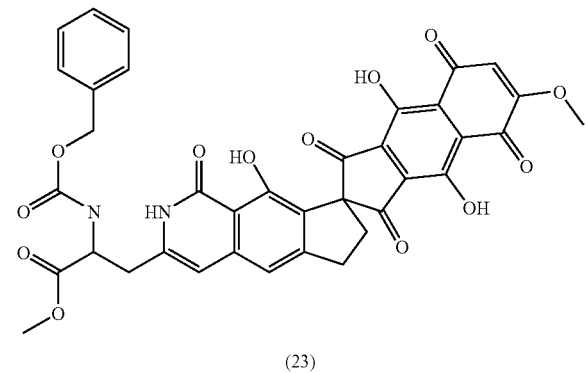

(23)

(a)

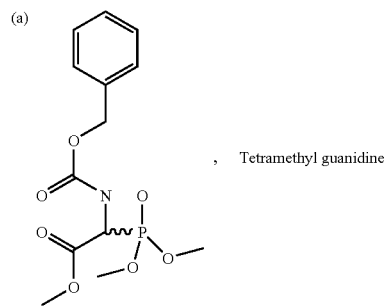

, Tetramethyl guanidine

The compound (24) is the precursor of an N-methylated fredericamycin derivative (diagram 8).

Diagram 8

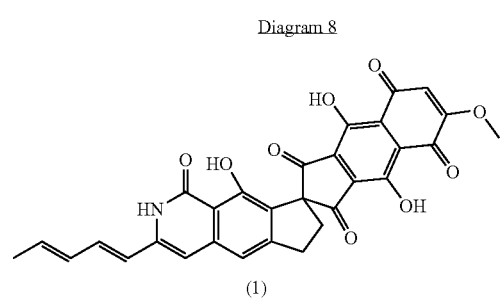

(1)

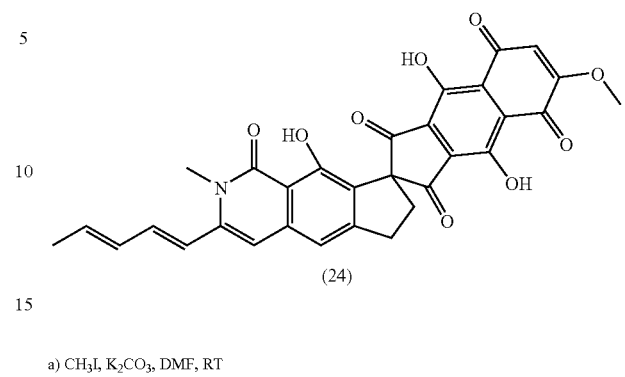

(24)

a) CH₃I, K₂CO₃, DMF, RT

Fredericamycin may be transformed by palladium/hydrogen almost quantatively to tetrahydro fredericamycin (25), and may be halogenated in the nucleus according to the above described methods, e.g. to the bromine compound (26) (diagram 9):

Diagram 9

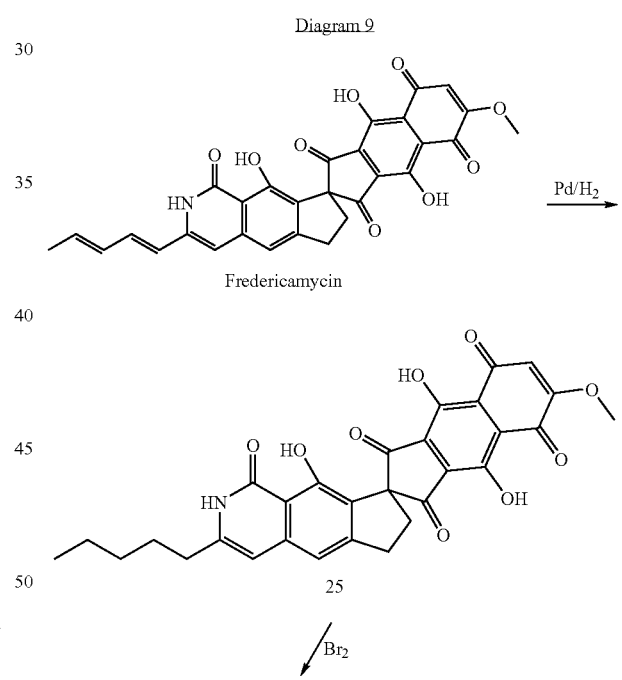

25

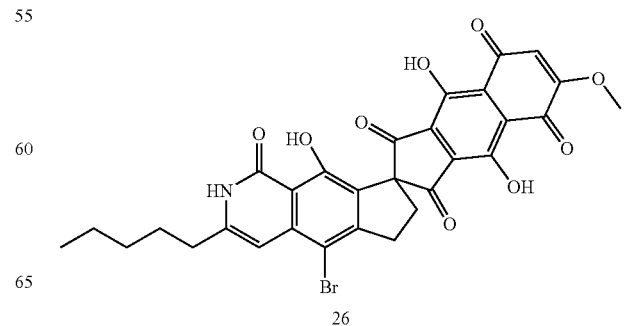

26

Surprisingly it has also been found that the methoxy groups in fredericamycin and the derivatives according to the invention can be exchanged under alkali or earth alkali acetate catalysis by oxygen nucleophiles such as alcohols or polyols. Thereby, the alcohols can carry a multitude of different substituents (table 4).

Diagram 10

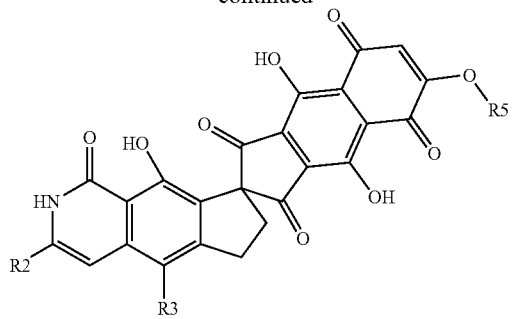

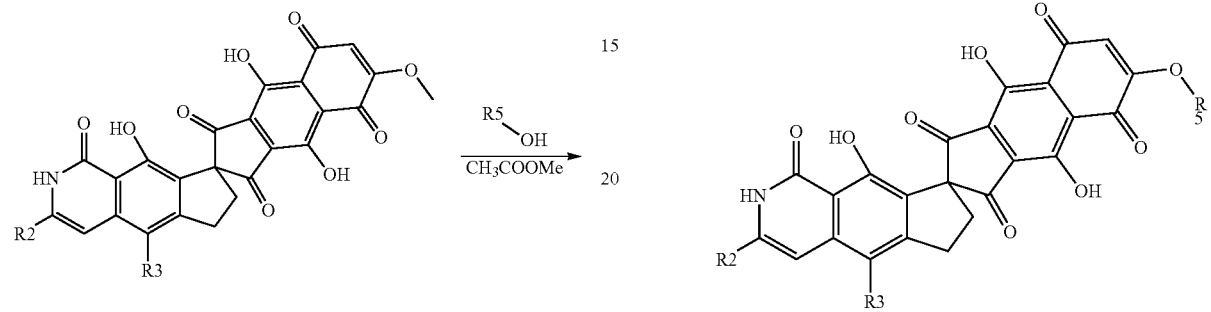

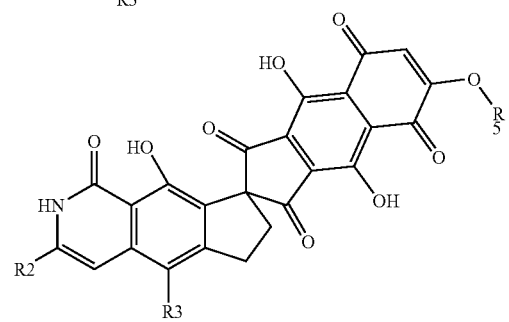

TABLE 4

| Example | R2 | R3 | R5 | UV$_{max}$ (nm) | m/e | Yield (%) |
|---|---|---|---|---|---|---|
| 243 | H$_3$C-CH=CH-CH=CH-CH$_3$ | H | H$_3$C-CH$_2$- | 504 | (M + H) 554 | 97 |
| 244 | H$_3$C-CH=CH-CH=CH-CH$_3$ | H | H$_3$C-CH$_2$-CH$_2$-CH$_2$- | 500 | (M+) 582 | 96 |
| 245 | H$_3$C-CH=CH-CH=CH-CH$_3$ | H | (H$_3$C)$_2$CH- | 500 | (M + H) 568 | 70 |
| 246 | H$_3$C-CH=CH-CH=CH-CH$_3$ | H | (H$_3$C)(CH$_3$)N-CH$_2$-CH$_2$- | 504 | (M + H) 597 | 36 |
| 247 | H$_3$C-CH=CH-CH=CH-CH$_3$ | Br | H$_3$C-CH$_2$- | 504 | (M+) 632/634 | 71 |
| 248 | H$_3$C-CH=CH-CH=CH-CH$_3$ | H | H$_2$C=CH-CH$_2$- | 500 | (M + H) 566 | 91 |
| 249 | H$_3$C-CH=CH-CH=CH-CH$_3$ | H | HO-CH$_2$-CH$_2$- | 499 | (M+) 569 | 52 |
| 250 | H$_3$C-CH=CH-CH=CH-CH$_3$ | H | C$_6$H$_5$-CH$_2$- | 504 | (M + H) 616 | 99 |

TABLE 4-continued

| Example | R2 | R3 | R5 | UV$_{max}$ (nm) | m/e | Yield (%) |
|---|---|---|---|---|---|---|
| 251 | H$_3$C-CH=CH-CH=CH- | H | cyclopropyl-CH$_2$- | 500 | (M+) 580 | 99 |
| 252 | H$_3$C-CH(OH)-CH(OH)-CH(OH)-CH(OH)- | H | H$_3$C-CH$_2$- | 499 | (M + H) 622 | 20 |
| 253 | H$_3$C-CH=CH-CH=CH- | H | -CH$_2$-CH$_2$-NH-C(O)-O-C(CH$_3$)$_3$ | 500 | (M + H) 669 | 99 |
| 254 | H$_3$C-CH=CH-CH=CH- | H | (H$_3$C)$_2$CH-N(CH(CH$_3$)$_2$)-CH$_2$-CH$_2$- | 504 | (M + H) 653 | 48 |
| 255 | H$_3$C-CH=CH-CH=CH- | H | cyclopentyl-CH$_2$- | 504 | (M + H) 594 | 50 |
| 256 | H$_3$C-CH=CH-CH=CH- | H | -CH$_2$-CH$_2$-Br | 499 | (M + H) 632/634 | 99 |

Exchange of the Methoxy Group at the F Ring

The exchange of the methoxy groups at the F ring of the fredericamycin and at the derivatives is possible by primary, secondary or aromatic amines. Thereby, the components are stirred with the appropriate primary or secondary amines at room temperature in DMF or in another inert solvent. With aromatic amines, a catalysis with Lewis acids such as stannous(IV)chloride, etc. is required.

Diagram 11

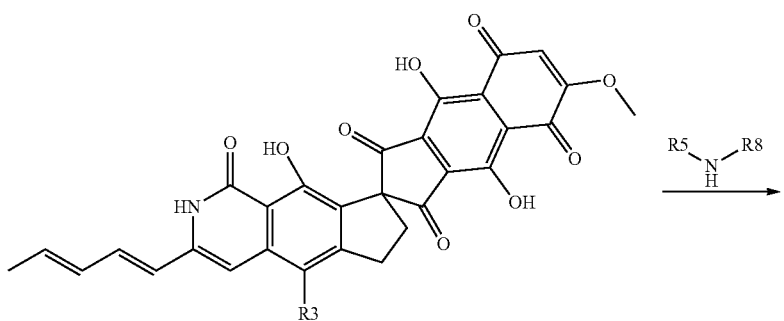

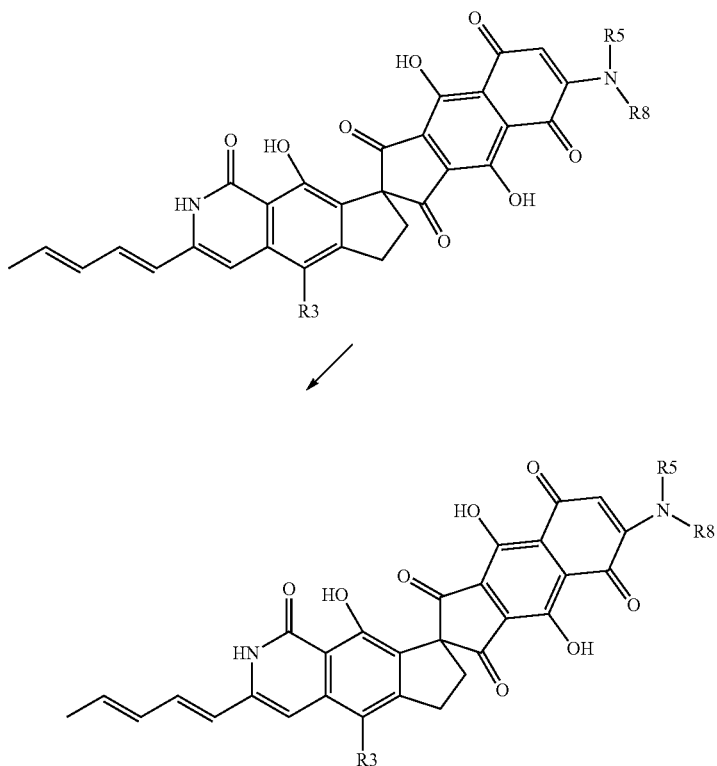
| TABLE 5 | | |
|---|---|---|
| R3 | R5—N—R8 | Example |
| I | H−N(CH3)−cyclopropyl | 257 |
| I | H−N(CH3)−CH2CH2CH2CH3 | 258 |
| Br | H−N(CH3)−CH2CH2CH2CH3 | 259 |
| H | H−N(CH3)−cyclopropyl | 260 |
| H | H−N(phenyl) | 261 |
| TABLE 5-continued | | |
|---|---|---|
| R3 | R5—N—R8 | Example |
| H | N-methylpiperidine | 262 |
| H | $H_3C-N(CH_3)-CH_3$ | 263 |
| H | H−N(CH3)−CH(CH3)2 | 264 |
| H | H−N(CH3)−CH3 | 265 |
| I | H−N(CH3)−CH3 | 266 |

TABLE 5-continued

| R3 | R5—N—R8 | Example |
|---|---|---|
| H | N-methylmorpholine | 267 |
| H | hydrazine (H2N-NH) | 268 |
| H | N-methylpyrrolidine | 269 |
| Br | N-methyl-N-cyclopropylamine | 270 |

Preparation of Heterocyclic Fredericamycin Derivatives

The fredericamycin aldehyde (4) can be reacted to pyridal acetone (271) according to Wittig or Wittig-Horner. Bromation with bromine in DMF yields the dibromo-derivative (272) substituted in the side chain and at the B ring. With the appropriately substituted thioamides or thioureas, the respective thiazole derivatives (273-276) are accessible.

TABLE 6

| R" | Example |
|---|---|
| NH₂ | 273 |
| Ph | 274 |
| CH₃CONH | 275 |
| CH₃ | 276 |

Preparation of Thioanalogoues of Fredericamycin Derivatives

By sulfurization of fredericamycin or its derivatives with Lawesson reagent or $P_4S_{10}$ in pyridine, the derivatives analogous to thiopyridone are accessible (see diagram 13).

Preparation of Thioanalogoues of Fredericamycin Derivatives

By sulfurization of fredericamycin or its derivatives with Lawesson reagent or $P_4S_{10}$ in pyridine, The derivatives analogous to thiopyridone are accessible (see diagram 13).

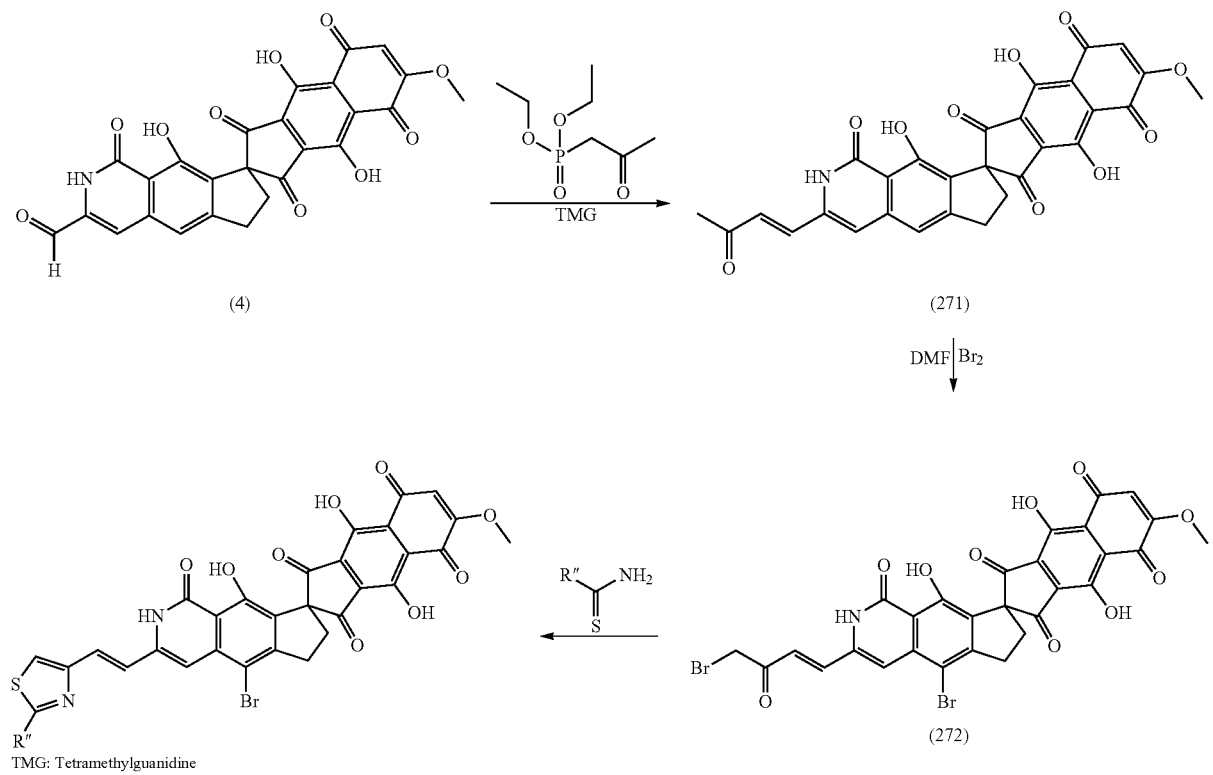

Diagram 12

TMG: Tetramethylguanidine

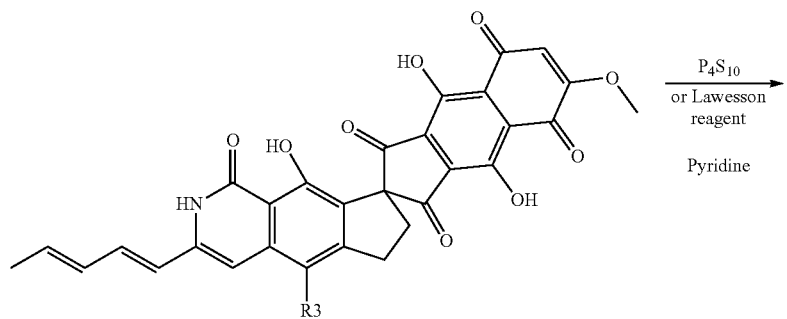
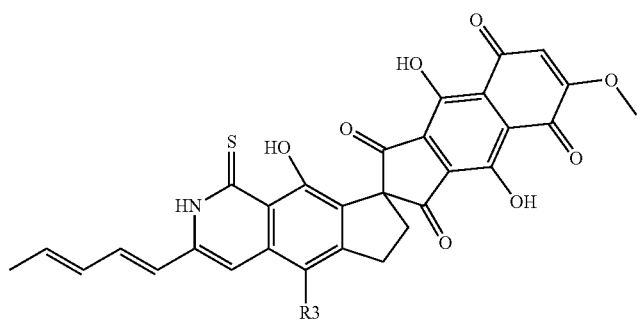
R3: H, (277)
Fredericamycin (1) forms inclusion compounds such as (25) with polysugars such as α-cyclodextrin, that have good water solubility compared to the original substance.
The dextrin inclusion compounds form easily if the components are mixed in the appropriate stoichiometric ratio in a suitable solvent such as DMSO (see diagram 11).
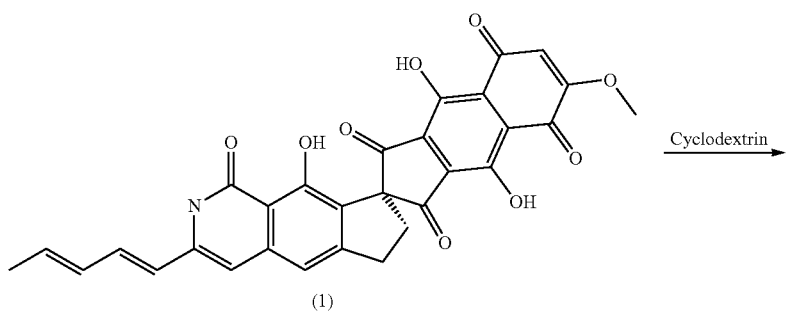

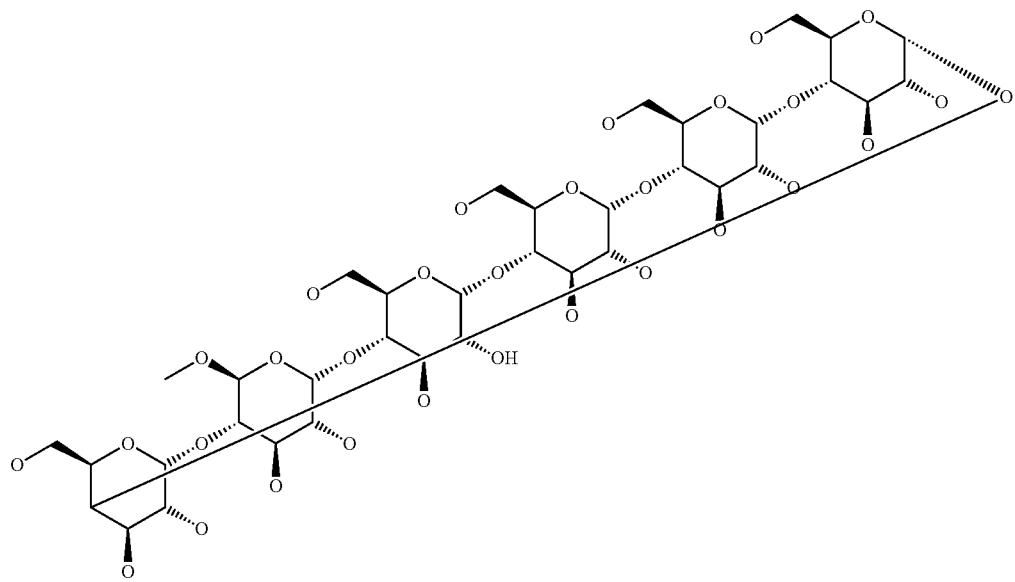
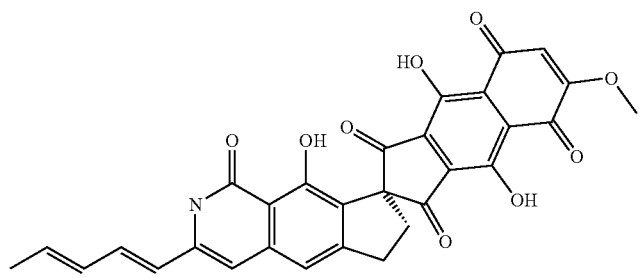
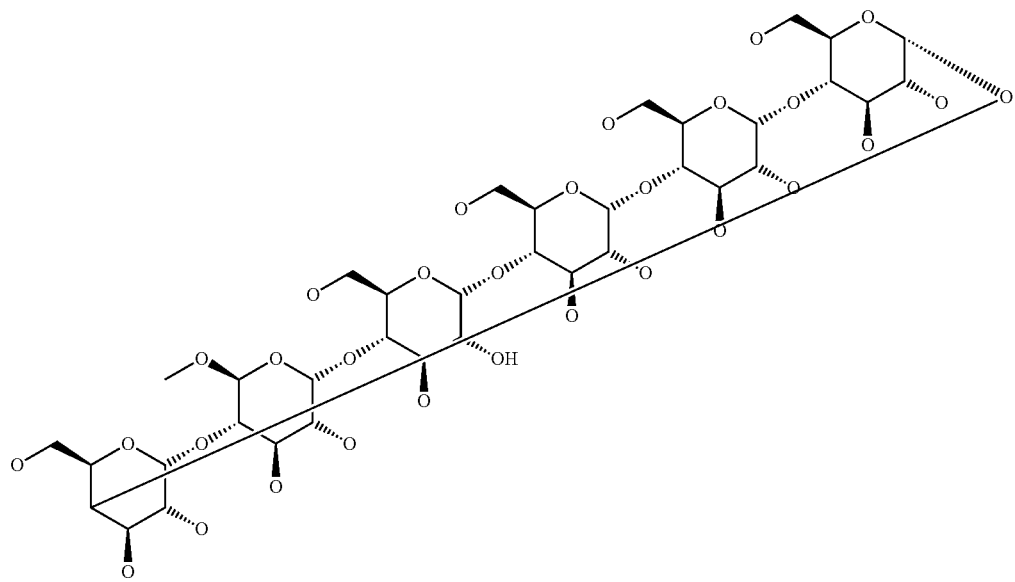
(22)
Biological Activity Against 12 Cancer Cell Lines:
LCL (H460, lung), MACL (MCF7, breast), LXFL (52L, lung), LXFA (629L, lung), MEXF (462NL, melanoma), MEXF (514L, melanoma), MAXF (401NL, breast), RXF (944L, renal), RXF (486L, renal), UXF (1138L, uterus), PRXF (PC3M, prostate), PRXF (22RV1).

Efficacy (IC70) Averaged Over all Cell Lines in μg/mL at 5 Test Concentrations

TABLE 7

| Example/reference | IC70 μg/mL |
|---|---|
| adriamycin | 0.0210 |
| cisplatin | 37.1020 |
| fredericamycin | 0.2790 |
| 1 | 0.1130 |
| 13 | 0.0050 |
| 14 | 0.0070 |
| 22 | 0.0080 |
| 23 | 0.0110 |
| 121 | 0.2020 |
| 127 | 0.1550 |
| 192 | 0.0750 |
| 196 | 0.0950 |
| 197 | 0.0340 |
| 198 | 0.2560 |
| 203 | 0.1590 |
| 212 | 0.2100 |
| 214 | 0.0220 |
| 215 | 0.0720 |
| 217 | 0.1290 |
| 218 | 0.0760 |
| 224 | 0.0470 |
| 225 | 0.1110 |
| 230 | 0.0910 |
| 232 | 0.3170 |
| 233 | 0.1000 |
| 234 | 0.0520 |
| 235 | 0.0810 |
| 236 | 0.1210 |
| 265 | 0.1330 |
| 275 | 0.3680 |
| 276 | 0.0840 |

EXAMPLES

Example 1

1-Desoxy-5-C-[(8R)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphalene]-3-yl]pentitol (2)

Two hundred (200) mg (0.38 mmol) fredericamycin A (1) are dissolved in 30 mL dichloromethane. After addition of 20 mL methanol and 4.4 ml water, 350 mg (2.6 mmol) N-methylmorpholine-N-oxide are added. Under vigorous stirring, 0.2 ml of a 2.5% osmium(IV)oxide solution in t-butanol is added dropwise. The reaction mixture is acidified with 2-3 drops of trifluoracetic acid. After stirring for 48 hours, the reaction is complete according to HPLC control (RP18, acetonitrile water (0.2% acetic acid)). The reaction mixture is added to 400 ml water under vigorous stirring, and the dark red crystalline solid is sucked off through a filter. Drying in HV. Yield: 195 mg (87% of the theoretical value) dark red powder. ES$^-$: M/e=606.2 (M+-H), $\lambda_{max}$: 504.0.

Example 2

Tri-potassium-1-desoxy-5-C-[(8R)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl]pentitol (3)

Twelve (12.0) mg (19.8 μmol) fredericamycin tetrol (2) are dissolved in 1.5 mL absolute pyridine under nitrogen atmosphere. The solution is gassed for 30 min with argon at 0° C. Under the argon atmosphere, 5.94 mL of a 0.01 N KOH solution are added at once at 0° C. The reaction solution immediately turns turquoise. The reaction mixture is stirred for another 1 hour, and subsequently is frozen and lyophilized. Yield: 13.2 mg (100% of the theoretical value); deep blue crystal mass.

Example 3

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde (4)

1.) Fifty (50) mg (82.3 μmol) tetrahydroxy fredericamycin (tetrol (2)) are dissolved in 4 mL DMF. Under vigorous stirring, an aqueous sodium iodate solution (300 mg NaIO$_4$ in 1 mL water) is added dropwise within one hour. After 1 h stirring at room temperature, 2 drops of trifluoracetic acid are added. After stirring for another 30 min, the reaction solution is diluted with 3 ml DMF, and 150 mg NaIO$_4$ dissolved in 0.5 ml water are added.

After another hour, 100 mL water are added. The supernatant over the precipitate is sucked off, and dryed in HV. Dark red crystal powder. Yield: 41 mg (100% of the theoretical value). M/e=501.3, UV$_{max}$: 504.0 nm.

2.) One hundred and nine (109) mg (179 μmol) fredericamycin tetrol (2) are dissolved in 8 mL pyridine. 180 μL water are added. To the reaction mixture, 450 mg (1.08 mmol, 6 eq.) (polystryrylmethyl)trimethylammonium periodate resin are added. Then the mixture is stirred for 12 h at RT. The resin is filtered off; washing and concentrating until dry. Dark red residue.

Yield: 89.9 mg (100% of the theoretical value). M/e=501.3, UV$_{max}$: 504.0 nm.

Example 4

1-[2-Oxo-2-((2E)-2-{[(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl]methylene)ethyl]-dimethylamino trifluoroacetate (118)

Twenty (20) mg (39.9 μmol) fredericamycin aldehyde (4) are dissolved under argon in 1.5 mL absolute DMF. Addition of 9.1 mg (47.9 μmol, 1.2 eq.) acetylhydrazide dimethylammoniumchloride (Girard reagent D) and 20 mg polyvinylpyridine (2% DVB). The mixture is stirred for 2.5 h. Then, 27 mg (80 μmol, 2.0 eq.) aldehyde Wang resin (coating: 3.0 mmol/g) are added and stirred for another 1 h. Then, the resin is filtered, and washed 3× with DMF. Concentration in high vacuum. The residue is dissolved in 1 ml trifluoracetic acid, and concentrated after 10 min until dry.

Red solid; Yield: 28.5 mg (100%); ES$^+$: M/e=601.3, UV$_{max}$: 504.0 nm.

Example 5

1-[2-Oxo-2-((2E)-2-{[(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl]methylene}hydrazino)-ethyl]pyridinium chloride (119)

Fifteen (15) mg (29.9 μmol) fredericamycin aldehyde (4) are dissolved in 3 mL DMF. At room temperature 7.5 mg (40.0 µmol) acethydrazinopyridinium chloride (Girard reagent P) dissolved in 75 µL water are added. The reaction mixture is stirred for 1.5 h at room temperature, and the course of the reaction is monitored by HPLC. When finished, acetic acid ethyl ester is added to the reaction mixture, until a precipitation occurs. After the crystallization is finished, the red solid is sucked off.

Yield: 9.1 mg (44% of the theoretical value). M/e=635.2; $\lambda_{max}$: 486.0.

Example 6

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde oxime (122)

Ten (10) mg (19.4 µmol) fredericamycin aldehyde (4) are dissolved in 2 mL DMF. After addition of 3.1 mg (44.6 µmol) hydroxylammonium chloride, 3.2 µl pyridine are added. Stirring for 2 h at room temperature. The reaction mixture is added to 50 ml water and extracted 3 times with ethyl acetate. After drying and concentration, a deep red amorphous crystal powder was left (HPLC clean).

Yield: 7.4 mg (72% of the theoretical value). ES$^-$: M/e=516.1; $\lambda_{max}$: 500.0 nm.

Example 7

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-O-methyloxime (8)

Ten (10) mg (19.4 µmol) fredericamycin aldehyde (4) are dissolved in 2 mL DMF. After addition of 3.4 mg (40.7 µmol) O-methylhydroxylammonium chloride and 3.2 µl pyridine, the reaction mixture is stirred for 2 h at room temperature. Then, it is added to 100 ml water, and the supernatant is sucked off from the red precipitate (HPLC clean).

Yield: 7.6 mg (71% of the theoretical value). ES$^+$: M/e=531.2; $\lambda_{max}$: 500.0.

Example 8

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-O-benzyloxime (9)

Ten (10) mg (19.4 µmol) fredericamycin aldehyde (4) are dissolved in 2 mL DMF. After addition of 6.4 mg (43.2 µmol) O-benzylhydroxylammonium chloride and 3.2 µl pyridine, the reaction mixture is stirred for 2 h at room temperature. Then, it is added to 50 ml water, and the supernatant is sucked off from the red precipitate (HPLC clean).

Yield: 6.8 mg (57% of the theoretical value). ES$^+$: M/e=607.2; $\lambda_{max}$: 504.0 nm.

Example 9

1-O-({(1E)-[(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl]methylene}amino)-β-D-glucopyranose (10)

Two (2.0) mg (4.0 µmol) fredericamycin aldehyde (4) are dissolved in 150 µL DMF, and 0.86 mg (4.4 µmol) β-aminoxy-D-glucopyranose is added. The mixture is stirred for 24 h at room temperature, and 5 mg (15.0 µmol) aldehyde Wang resin (coating: 3.0 mmol/g) is added. After stirring for another 3 h, the resin is filtered off, washed with DMF, and the filtrate is concentrated in high vacuum until dry.

Yield: 2.7 mg (99% of the theoretical value), red powder; ES$^-$: M/e=678.1; $\lambda_{max}$: 504.0 nm.

Example 10

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-1,1',3',5',8'(2H)-pentone (11)

Thirty (30) mg (49.4 µmol) tetrahydroxy fredericamycin (2) were dissolved in 2 mL pyridine. Twenty (20) mg (93.0 µmol) sodium metaperiodate dissolved in 0.3 ml water are added. After stirring for 4 h, 10 mg (260 µmol) sodium borohydride are added. After 12 h, concentration until dry, and the residue is separated by preparative HPLC.

Yield: 2.6 mg (13% of the theoretical value) red powder. ES$^-$: M/e=503.2; $\lambda_{max}$: 504.0 nm.

Example 11

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carboxylic acid (12)

Fifteen (15) mg (29.9 µmol) fredericamycin aldehyde (4) are dissolved in 1 mL dichloromethane and 0.5 ml t-butanol. Addition of 250 µl 2,4-dimethylbutene. Under stirring at room temperature, a solution of 6.0 mg (53.1 µmol) sodium chlorite (80%) and 5.1 mg sodium hydrogenphosphate in 250 µl water are added dropwise.

After 2.5 h, again a solution of 10.0 mg (88.5 µmol) sodium chlorite and 5 mg sodium dihydrogenphosphate in 200 µl water are added. After altogether 4 h, it is put on water, and extracted with ethyl acetate.

The raw mixture was purified by preparative HPLC (RP18, acetonitrile-water-acetic acid). Red amorphous powder.

Yield: 68.3 mg (53.5% of the theoretical value). E$^-$: M/e=516.1; $\lambda_{max}$: 504.0 nm.

Example 12

Potassium(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carboxylate (13)

6.9 mg (13.3 µmol) Fredericamycin carboxylic acid (12) are dissolved in 5 mL DMF under nitrogen. At room temperature and under oxygen exclusion and vigorous stirring, 1.27 mL (12.7 µmol) of an aqueous 0.01 N KOH solution is added dropwise. It is stirred for 15 minutes at room temperature, and concentrated in high vacuum until dry.

Yield: 7.40 mg (100% of the theoretical value). E$^-$: M/e=516.1; $\lambda_{max}$: 504.0 nm.

Example 13

(8S)-5-bromo-4',9,9'-trihydroxy-6'-methoxy-1,1',3', 5',8'-pentaoxo-1,1',2,3',5',6,7,8'-octahydrospiro[cyclopenta[g]isoquinoline-8,2'-cyclopenta[b]-naphthalene]-1,1',3',5',8'(2H)-pentone (14)

Twenty (20) mg (37.1 μmol) fredericamycin (1) were dissolved in 250 μl DMF, and then 6. 3 mg (35.3 μmol) N-bromosuccinimide in 250 μl DMF were added within one hour at 0° C. The reaction was stirred in a slowly thawing ice bath over night. Then, the DMF is removed in high vacuum, and the residue is purified by preparative HPLC.

Yield: 7 mg (32% of the theoretical value) red crystal mass. M/e=616.1/618.1; $\lambda_{max}$: 486.0 nm.

Example 14

(8S)-5-iodo-4',9,9'-trihydroxy-6'-methoxy-1,1',3',5', 8'-pentaoxo-1,1',2,3',5',6,7,8'-octahydrospiro[cyclopenta[g]isoquinoline-8,2'-cyclopenta[b]-naphthalene]-1,1',3',5',8'(2H)-pentone (15)

Eighty four (84) mg (158 μmol) fredericamycin (1) were dissolved in 1.0 μl DMF, and then 33.0 mg (150.0 μmol) N-iodosuccinimide in 500 μl DMF were added within one hour at 0° C. The reaction was stirred in a slowly thawing ice bath over night. Then, the DMF is removed in high vacuum, and the residue (120 mg (14) with a content of 80%) is purified by preparative HPLC (gradient CH$_3$CN 50-90% over 16 min.)

Yield: 18 mg (17% of the theoretical value) red crystal mass. M/e=665.0; $\lambda_{max}$: 484.0 nm.

Example 15

Methyl-2-{[(benzyloxy)carbonyl]amino}-3-[(8S)-4', 9,9'-trihydroxy-6'-methoxy-1,1',3',5',8'-pentaoxo-1, 1',2,3',5',6,7,8'-octahydrospiro[cyclopenta[g]isoquinoline-8,2'-cyclopenta[b]-naphthalene]-3-yl] acrylate (23)

Sixty six (66) mg (200 μmol) Z-α-phosphonoglycine trimethylester are dissolved under argon in 1 mL absolute pyridine, and 25 μL 1,1,3,3-tetramethylguanidine are added at 0° C. After 40 min. 20 mg (40 μmol) fredericamycin aldehyde (4) is added at 0° C. After 15 min. 20 ml 1 M acetic acid is added, and the mixture is extracted 3× with acetic acid. The raw product is purified by preparative HPLC (RP18, acetonitrile-water).

Yield: 10.0 mg (36% of the theoretical value). M/e=706.4; $\lambda_{max}$: 492.0 nm.

Example 16

(8S)-9-hydroxy-4',6',9'-trimethoxy-2-methyl-3-[(1E, 3E)-penta-1,3-dienyl]-6,7-dihydrospiro[cyclopenta [g]isoquinoline-8,2'-cyclopenta[b]-naphthalene]-1,1', 3',5',8'(2H)-pentone (24)

Ten (10) mg (15 μmol) fredericamycin (1) were dissolved under protective gas in 4 ml absolute DMF. At RT, 400 μl (4311 μmol) methyliodide and 81 mg powdered potassium carbonate are added. The reactions mixture is then stirred at RT for 20 h, and is then transferred onto water. Extraction with ethyl acetate, and purification of the residue by separating chromatography on chloroform/methanol 30/1.

Yield: 4 mg (37% of the theoretical value). Yellow residue. M/e=582.3; $\lambda_{max}$: 368.0 nm.

Example 17

Fredericamycin A 1:2 complex with α-cyclodextrin (22)

Ten (10) mg fredericamycin (0.025 mMol) are added to a solution of 50 mg α-cyclodextrin (0.050 mMol) in 500 μl dimethylsulfoxide. The solution is then diluted with 5 ml water. A stock solution prepared in such way can be diluted as desired with water.

$\lambda_{max}$=504.0 nm.

Example 18

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde(4-methylpiperazine-1-yl)hydrazone (111)

Five (5) mg (9.42 μmol) fredericamycin aldehyde (4) are dissolved in 500 μl DMF and 25 μl trifluoracetic acid. At room temperature, 1.30 mg (11.3 μmol) 1-amino-4-methyl-piperazine is added. After stirring for 4.5 h at room temperature, 1 equivalent each of Wang aldehyde resin and sulfonohydrazide resin is added and stirred for 2 h.

Filtration and concentration of the reaction solution at high vacuum.

Red powder. Yield: 5.4 mg (91% of the theoretical value). M/e=599 (M+H)+; $\lambda_{max}$: 504.0 nm.

Example 19

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-4,5-dihydro-1H-imidazole-2-yl-hydrazone (123)

Five (5.00) mg (9.42 μmol) fredericamycin aldehyde (4) are dissolved in 500 μl DMF and 25 μl trifluoracetic acid. At room temperature, 2.05 mg (11.3 μmol) 2-hydrazino-2-imidazolin hydrobromide is added. After stirring for 4.5 h at room temperature, 1 equivalent each of Wang aldehyde resin and sulfonohydrazide resin are added and stirred for 2 h. Separation of the resin by filtration and concentration of the reaction solution at high vacuum.

Red powder. Yield: 3.9 mg (67% of the theoretical value). M/e=584 (M+H)+; $\lambda_{max}$: 504.0 nm.

Example 20

4',9,9'-Trihydroxy-6'-methoxy-3-{(E)-[(4-oxo-2-thioxo-1,3-thiazolidin-3-yl)imino]methyl}-6,7-dihydrospiro[cyclopenta[g]isoquinoline-8,2'-cyclopenta [b]-naphthalene]-1,1',3',5',8'(2H)-pentone (123)

Five (5.00) mg (9.42 μmol) fredericamycin aldehyde (4) are dissolved in 500 μl DMF and 25 μl trifluoracetic acid. At room temperature, 1.67 mg (11.3 μmol) 2N-aminorhodanide are added. After stirring for 4.5 h at room temperature, 1 equivalent each of Wang aldehyde resin and sulfonohydrazide resin are added and stirred for 2 h.

Example 21

4',9,9'-Trihydroxy-6'-methoxy-1,1',3',5',8'-pentaoxo-1,1',2,3',5',6,7,8'-octahydrospiro[cyclopentag]isoquinoline-8,2'-cyclopenta[b]-naphthalene]-3-carbaldehyde-O-(2-morpholine-4-ylethyl)oxime (27)

Five (5.00) mg (9.42 µmol) fredericamycin aldehyde (4) are dissolved in 500 µl DMF and 25 µl trifluoracetic acid. At room temperature, 2.47 mg (11.3 µmol) N-(aminoxyethyl) morpholine dihydrochloride is added. After stirring for 4.5 h at room temperature, 1 equivalent of Wang aldehyde resin (3.1 mg, 9.4 µmol, coating: 3.0 mmol/g) as well as 1 equivalent sulfonohydrazide resin (6.1 mg, 9.4 mmol, 1.5 mmol) are added and stirred for 2 h.

Filtration and concentration of the reaction solution.

Red powder. Yield: 6.1 mg (98% of the theoretical value). M/e=630 (M+H)+; $\lambda_{max}$: 504.0 nm.

Example 22

(8S)-5-chloro-4',6',9'-trimethoxy-2-methoxy-3-[(1E,3E)-penta-1,3-dienyl]-6,7-dihydrospiro[cyclopenta[g]isoquinoline-8,2'-cyclopenta[b]-naphthalene]-1,1',3',5',8'(2H)-pentone (34)

Three hundred (300) mg (556.6 µmol) fredericamycin (1) are dissolved under argon in 10 µl DMF, and then 75.0 mg (556.6 µmol) N-chlorosuccinimide are added. The reaction is stirred for 5 h at 40° C. The reaction mixture is then added to 400 ml methanol/water 1:1, and the red precipitate is sucked off and dried at high vacuum.

Yield: 305 mg (96% of the theoretical value) red crystal mass. M/e=573/575; $\lambda_{max}$: 504.0 nm.

Example 23

(8S)-5-fluoro-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1',3',5',8'(2H)-pentone (35)

Fifty (50) mg (92.8 µmol) fredericamycin (1) are dissolved in 5 ml DMF under argon, and then 33.0 mg (93.5 µmol) 1-chloromethyl-4-fluoro-1,4-diazoniabicyclo[2.2.2]octane bis(tetrafluoroborate) Selectfluor (is added. The reaction is stirred for 24 h at room temperature. The reaction mixture is then added to 200 ml water, and is extracted with ethyl acetate. The concentrated raw product is purified by preparative HPLC (RP18, acetonitrile-water-acetic acid).

Yield: 7.1 mg (14% of the theoretical value) red crystal mass. M/e=557; $\lambda_{max}$: 504.0 nm.

Example 24

1-Desoxy-5-C-[(8R)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl]-pentitol (36)

Hundred twenty (120) mg (209 mmol) chlorofredericamycin (34) are dissolved in 25.0 ml dichloromethane. After addition of 3.6 ml methanol and 0.8 ml water, 197 mg (1.46 mmol) N-methylmorpholine-N-oxide is added. Under vigorous stirring, 0.12 ml of a 2.5% solution of osmium(IV)oxide in t-butanol is added dropwise. After stirring for 27 hours, the reaction is complete, according to HPLC monitoring (RP18, acetonitrile-water (0.2% acetic acid)). The reaction mixture is added to 200 ml water under vigorous stirring, and the dark red solid is sucked off. Drying in HV.

Yield: 101 mg (75% of the theoretical value) dark red powder. M/e=641/643; $\lambda_{max}$: 504.0.

Example 25

(8S)-4',9,9'-trihydroxy-5-bromo-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde (37)

Hundred (100) mg (200 µmol) fredericamycin aldehyde (4) are dissolved under argon in 5 ml DMF. Then, 200 µl of a 1M bromine solution in DMF is added. After stirring for 1.5 h at RT, another 20 µl bromine solution are added. According to HPLC monitoring, the reaction mixture is complete after 3.5 h.

Add to 150 ml water, and shake out with dichloromethane.

Yield: 96 mg (83% of the theoretical value) dark red powder. M/e=579/581; $\lambda_{max}$: 504.0.

Example 26

1,2,3,4-Tetrahydro-5-bromo-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1',3',5',8'(2H)-pentone (26)

Eight (8.0) mg (0.0128 mmol) 1,2,3,4-tetrahydrofredericamycin (25) are dissolved in 1 ml absolute DMF under nitrogen. Then a solution of 2.3 mg (0.0128 mmol) bromine in 0.25 ml DMF is added dropwise to the solution. Stirring at room temperature over 24 h. The reaction mixture is concentrated to half volume in high vacuum, and is then transferred onto 100 ml water. The supernatant is sucked off from the precipitate and dried in a vacuum.

Red crystal powder 8.1 mg (88% of the theoretical value) m/e=621/623; $\lambda_{max}$: 499 nm.

Example 27

(8S)-4',9,9'-trihydroxy-6'-benzylamino-3-[(1E,3E)-penta-1,3-dienyl]-6,7-dihydrospiro[cyclopenta[g]isoquinoline-8,2'-cyclopenta[b]-naphthalene]-1,1',3',5',8'(2H)-pentone Twenty (20) mg (37.1 µmol) fredericamycin are dissolved in 1 ml DMF under argon, then 4.76 mg (44.50 µmol) benzylamine are added at room temperature. According to HPLC (RP18, acetonitrile/water), a homogenous new product has formed after 3 h. The reaction mixture is concentrated at high vacuum until dry.

Red crystal mass; Yield: 23 mg (100% of the theoretical value) M/e=615.3 (M+H); $\lambda_{max}$: 492 nm.

Example 28

(8S)-5-chloro-4',9,9'-trihydroxy-6'-benzylamino-3-[(1E,3E)-penta-1,3-dienyl]-6,7-dihydrospiro[cyclopenta[g]isoquinoline-8,2'-cyclopenta[b]-naphthalene]-1,1',3',5',8'(2H)-pentone Five (5.0) mg (8.71 µmol) 5-chlorofredericamycin are dissolved in 1 ml DMF under argon, then 1.12 mg (10.45 µmol)

benzylamine are added at room temperature. After 29 h, the reaction mixture is concentrated at high vacuum until dry.

Red crystal mass; Yield: 5 mg (89% of the theoretical value) M/e=649.1 (M+H); $\lambda_{max}$: 492 nm.

Example 28

Translator: 28a (8S)-4',9,9'-trihydroxy-6'-ethanolamino-3-[(1E,3E)-penta-1,3-dienyl]-6,7-dihydrospiro[cyclopenta[g]isoquinoline-8,2'-cyclopenta[b]-naphthalene]-1,1',3',5',8'(2H)-pentone Ten (10) mg (18.6 μmol) fredericamycin are dissolved in 1 ml DMF under argon, then 1.36 mg (22.3 μmol) ethanolamine are added at room temperature. According to HPLC (RP18, acetonitrile/water), a homogenous new product has formed after 3 h. The reaction mixture is concentrated at high vacuum until dry.

Red crystal mass; Yield: 9 mg (85% of the theoretical value) M/e=569.3 (M+H); $\lambda_{max}$: 500 nm.

Example 29

(8S)-4',9,9'-trihydroxy-6'-(4-piperidylmethylamino)-3-[(1E,3E)-penta-1,3-dienyl]-6,7-dihydrospiro[cyclopenta[g]isoquinoline-8,2'-cyclopenta[b]-naphthalene]-1,1',3',5',8'(2H)-pentone Ten (10) mg (18.6 μmol) fredericamycin are dissolved in 1 ml DMF under argon, then 2.7 Pl (22.3 μmol) 4-aminomethylpiperidine are added at room temperature. The reaction mixture is concentrated at high vacuum until dry after 24 h.

Red crystal mass; Yield: 11 mg (99% of the theoretical value) M/e=622.3 (M+H); $\lambda_{max}$: 492 nm.

Examples 100-142

The compounds 100-142 can be generated analogously to examples 7, 8, 9, 10, 18, 19 and 20:

Example 100

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydepyridine-2-yl-hydrazone (100)

Yield: (95% of the theoretical value) MS: M/e=593.1; $\lambda_{max}$: 500.0 nm.

Example 101

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde[4-(trifluoromethyl)pyrimidine-2-yl]hydrazone (101)

Yield: (95% of the theoretical value) MS: M/e=562.1; $\lambda_{max}$: 500.0 nm.

Example 102

N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]pyridyl-3-carbohydrazine (102)

Yield: (95% of the theoretical value) MS: M/e=621.1; $\lambda_{max}$: 492.0 nm.

Example 103

N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]isonicotinohydrazine (103)

Yield: (95% of the theoretical value) MS: M/e=621.1; $\lambda_{max}$: 500.0 nm.

Example 104

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-1,2,4-triazole-4-ylhydrazone (104)

Yield: (80% of the theoretical value) MS: M/e=568.1; $\lambda_{max}$: 500.0 nm.

Example 105

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-4,5-dihydro-1H-imidazole-2ylhydrazone (105)

Yield: (95% of the theoretical value) MS: M/e=584.1; $\lambda_{max}$: 492.0 nm.

Example 106

N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-2-furohydrazine (106)

Yield: (95% of the theoretical value) MS: M/e=610.0; $\lambda_{max}$: 492.0 nm.

Example 107

4-Amino-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]benzohydrazine (107)

Yield: (95% of the theoretical value) MS: M/e=635.1; $\lambda_{max}$: 492.0 nm.

Example 108

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydethiosemicarbazone (108)

Yield: (95% of the theoretical value) MS: M/e=558.0; $\lambda_{max}$: 492.0 nm.

Example 109

N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]thiophene-2-carbohydrazine (109)

Yield: (95% of the theoretical value) MS: M/e=626.0; $\lambda_{max}$: 492.0 nm.

Example 110

2-(1H-indole-3-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazine (110)

Yield: (95% of the theoretical value) MS: M/e=673.1; 1$\lambda_{max}$: 492.0 nm.

Example 111

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde(4-methylpiperazine-1-yl)hydrazone (111)

Yield: (95% of the theoretical value) MS: M/e=599.1; $\lambda_{max}$: 492.0 nm.

Example 112

2-Oxo-2-{(2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-hydrazino)acetamide (112)

Yield: (95% of the theoretical value) MS: M/e=587.1; $\lambda_{max}$: 492.0 nm.

Example 113

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-1,1',3',5',8'(2H)-pentone (113)

Yield: (95% of the theoretical value) MS: M/e=632.0; $\lambda_{max}$; $\lambda_{max}$:500.0 nm.

Example 114

{(2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-hydrazino}acetonitrile (114)

Yield: (95% of the theoretical value) MS: M/e=583.1; $\lambda_{max}$: 492.0 nm.

Example 115

2-Amino-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]benzohydrazine (115)

Yield: (95% of the theoretical value) MS: M/e=635.1; $\lambda_{max}$: 492.0 nm.

Example 116

4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[2-morpholine-4-yl-ethyl]oxime (116)

Yield: (85% of the theoretical value) MS: M/e=630.1; $\lambda_{max}$: 492.0 nm.

Example 117

(2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazinecarboximidamide (117)

Yield: (95% of the theoretical value) MS: M/e=558.1; $\lambda_{max}$: 500.0 nm.

Example 118

2-(Dimethylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazine (118)

Yield: (85% of the theoretical value) MS: M/e=601.1; $\lambda_{max}$: 492.0 nm.

Example 119

1-[2-Oxo-2-((2E)-2-{[(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene}hydrazino)ethyl]pyridinium chloride (119)

Yield: (85% of the theoretical value) MS: M/e=635.1; $\lambda_{max}$: 492.0 nm.

Example 120

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-methyloxime (120)

Yield: (90% of the theoretical value) MS: M/e=531.1; $\lambda_{max}$: 492.0 nm.

Example 121

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-benzyloxime (121)

Yield: (95% of the theoretical value) MS: M/e=607.1; $\lambda_{max}$: 492.0 nm.

Example 122

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde oxime (122)

Yield: (95% of the theoretical value) MS: M/e=517.1; $\lambda_{max}$: 482.0 nm.

Example 123

1-O-({(1E)-[(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene}amino)-β-D-glucopyranose (123)

Yield: (95% of the theoretical value) MS: M/e=679.1; $\lambda_{max}$: 500.0 nm.

Example 124

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-phenylsemicarbazone (124)

Yield: (95% of the theoretical value) MS: M/e=635.1; $\lambda_{max}$: 492.0 nm.

Example 125

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydesemicarbazone (125)

Yield: (95% of the theoretical value) MS: M/e=559.1; $\lambda_{max}$: 492.0 nm.

Example 126

2-Piperidino-4-yl-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (126)

Yield: (95% of the theoretical value) MS: M/e=641.1; $\lambda_{max}$: 492.0 nm.

Example 127

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-chlorobenzyl)oxime (127)

Yield: (95% of the theoretical value) MS: M/e=641.1; $\lambda_{max}$: 492.0 nm.

Example 128

N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-(2-methyl-1,3-thiazole-4yl)carbohydrazide (128)

Yield: (95% of the theoretical value) MS: M/e=641.1; $\lambda_{max}$: 492.0 nm.

Example 129

2-(1H-imidazole-1-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (129)

Yield: (90% of the theoretical value) MS: M/e=624.1; $\lambda_{max}$: 500.0 nm.

Example 130

2-(Acetylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (130)

Yield: (95% of the theoretical value) MS: M/e=615.1; $\lambda_{max}$: 492.0 nm.

Example 131

2-(4-Methylpiperazine-1-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (131)

Yield: (50% of the theoretical value) MS: M/e=656.1; $\lambda_{max}$: 492.0 nm.

Example 132

2-Morpholine-4-yl-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene] acetohydrazide (132)

Yield: (60% of the theoretical value) MS: M/e=643.1; $\lambda_{max}$: 492.0 nm.

Example 133

2-(Methylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene] acetohydrazide (133)

Yield: (70% of the theoretical value) MS: M/e=587.1; $\lambda_{max}$: 492.0 nm.

Example 134

2-[Isopropyl(methyl)amino]-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene] acetohydrazide (134)

Yield: (70% of the theoretical value) MS: M/e=629.1; $\lambda_{max}$: 492.0 nm.

Example 135

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[2-(dimethylamino)ethyl]oxime (127)

Yield: (90% of the theoretical value) MS: M/e=588.1; $\lambda_{max}$: 492.0 nm.

Example 136

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[3-(4-(3-chlorophenyl)-piperazine-1-yl)propyl]oxime (136)

Yield: (85% of the theoretical value) MS: M/e=753.1; $\lambda_{max}$: 492.0 nm.

Example 137

4',9,9'-Trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[3-(dimethylamino)propyl]oxime (137)

Yield: (70% of the theoretical value) MS: M/e=602.1; $\lambda_{max}$: 492.0 nm.

Example 138

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydepyridine-2-yl-hydrazone (138)

Yield: (95% of the theoretical value) MS: M/e=627.0; $\lambda_{max}$: 500.0 nm.

Example 139

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde[4-(trifluoromethyl)pyrimidine-2-yl]hydrazone (139)

Yield: (95% of the theoretical value) MS: M/e=696.0; $\lambda_{max}$: 500.0 nm.

Example 140

(8S)-5-chloro-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]pyridyl-3-carbohydrazine (140)

Yield: (95% of the theoretical value) MS: M/e=655.0; $\lambda_{max}$: 500.0 nm.

Example 141

(8S)-5-chloro-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene] isonicotinohydrazide (141)

Yield: (95% of the theoretical value) MS: M/e=655.0; $\lambda_{max}$: 500.0 nm.

Example 142

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-1,2,4-triazole-4-ylhydrazone (142)

Yield: (90% of the theoretical value) MS: M/e=602.0; $\lambda_{max}$: 500.0 nm.

Example 143

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-4,5-dihydro-1H-imidazole-2-ylhydrazone (143)

Yield: (95% of the theoretical value) MS: M/e=618.0; $\lambda_{max}$: 500.0 nm.

Example 144

(8S)-5-chloro-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-2-furohydrazide (144)

Yield: (95% of the theoretical value) MS: M/e=644.0; $\lambda_{max}$: 500.0 nm.

Example 145

(8S)-5-chloro-4-amino-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-benzohydrazide (145)

Yield: (95% of the theoretical value) MS: M/e=669.0; $\lambda_{max}$: 500.0 mm.

Example 146

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydethiosemicarbazone (146)

Yield: (95% of the theoretical value) MS: M/e=609.0; $\lambda_{max}$:500.0 nm.

Example 147

(8S)-5-chloro-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]thiophene-2-carbohydrazide (147)

Yield: (95% of the theoretical value) MS: M/e=660.0; $\lambda_{max}$: 500.0 nm.

Example 148

(8S)-5-chloro-2-(1H-indole-3-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (148)

Yield: (95% of the theoretical value) MS: M/e=707.1; $\lambda_{max}$: 500.0 nm.

Example 149

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde(4-methylpiperazine-1-yl)hydrazone (149)

Yield: (95% of the theoretical value) MS: M/e=633.1; $\lambda_{max}$: 500.0 nm.

Example 150

(8S)-5-chloro-2-oxo-2-{(2E)-2-[4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazino}acetamide (150)

Yield: (95% of the theoretical value) MS: M/e=621.0; $\lambda_{max}$: 500.0 nm.

Example 151

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-1,1',3',5',8'(2H)-pentone (151)

Yield: (95% of the theoretical value) MS: M/e=665.3; $\lambda_{max}$: 500.0 nm.

Example 152

(8S)-5-chloro-{(2E)-2-[4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazino}acetonitrile (152)

Yield: (95% of the theoretical value) MS: M/e=617.1; $\lambda_{max}$: 500.0 nm.

Example 153

(8S)-5-chloro-2-amino-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]benzohydrazide (153)

Yield: (95% of the theoretical value) MS: M/e=669.1; $\lambda_{max}$: 500.0 nm.

Example 154

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[2-morpholine-4-yl-ethyl)oxime (154)

Yield: (95% of the theoretical value) MS: M/e=664.1; $\lambda_{max}$: 500.0 nm.

Example 155

(8S)-5-chloro-(2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazinecarboximidamide (155)

Yield: (95% of the theoretical value) MS: M/e=592.1; $\lambda_{max}$: 500.0 nm.

Example 156

(8S)-5-chloro-2-(dimethylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (156)

Yield: (95% of the theoretical value) MS: M/e=635.1; $\lambda_{max}$: 500.0 nm.

Example 157

(8S)-5-chloro-1-[2-oxo-2-((2E)-2-1[(8S)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazino)ethyl]pyridinium chloride (157)

Yield: (95% of the theoretical value) MS: M/e=669.1; $\lambda_{max}$: 500.0 nm.

Example 158

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-O-methyloxime (158)

Yield: (95% of the theoretical value) MS: M/e=565.0; $\lambda_{max}$: 500.0 nm.

Example 159

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-O-benzyloxime (159)

Yield: (95% of the theoretical value) MS: M/e=641.1; $\lambda_{max}$: 500.0 nm.

Example 160

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde oxime (160)

Yield: (95% of the theoretical value) MS: M/e=551.1; $\lambda_{max}$: 500.0 nm.

Example 161

(8S)-5-chloro-1-O-(((1E)-[(8S)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]amino)-β-D-glucopyranose (161)

Yield: (95% of the theoretical value) MS: M/e=713.1; $\lambda_{max}$: 500.0 nm.

Example 162

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-phenylsemicarbazone (162)

Yield: (95% of the theoretical value) MS: M/e=669.1; $\lambda_{max}$: 500.0 nm.

Example 163

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydesemicarbazone (163)

Yield: (90% of the theoretical value) MS: M/e=593.0; $\lambda_{max}$: 500.0 nm.

Example 164

(8S)-5-chloro-2-piperidino-4-yl-N'-[(1E)-[(8S)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (164)

Yield: (95% of the theoretical value) MS: M/e=675.1; $\lambda_{max}$: 500.0 nm.

Example 165

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-chlorobenzyl)oxime (165)

Yield: (90% of the theoretical value) MS: M/e=675.0; $\lambda_{max}$: 500.0 nm.

Example 166

(8S)-5-chloro-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]a-2-methyl-1,3-thiazole-4yl-carbohydrazide (166)

Yield: (95% of the theoretical value) MS: M/e=675.0; $\lambda_{max}$: 500.0 nm.

Example 167

(8S)-5-chloro-2-(1H-imidazole-1-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (1647)

Yield: (90% of the theoretical value) MS: M/e=658.1; $\lambda_{max}$: 500.0 nm.

Example 168

(8S)-5-chloro-2-(acetylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (164)

Yield: (95% of the theoretical value) MS: M/e=649.0; $\lambda_{max}$: 500.0 nm.

Example 169

(8S)-5-chloro-2-(4-methylpiperazine-1-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (169)

Yield: (60% of the theoretical value) MS: M/e=690.1; $\lambda_{max}$: 500.0 nm.

Example 170

(8S)-5-chloro-2-morpholine-4-yl-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (170)

Yield: (60% of the theoretical value) MS: M/e=677.1; $\lambda_{max}$: 500.0 nm.

Example 171

(8S)-5-chloro-2-(methylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (171)

Yield: (70% of the theoretical value) MS: M/e=621.1; $\lambda_{max}$: 500.0 nm.

Example 172

(8S)-5-chloro-2-[isopropyl(methyl)amino]-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (172)

Yield: (95% of the theoretical value) MS: M/e=675.1; $\lambda_{max}$: 500.0 nm.

Example 173

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[2-(dimethylamino)ethyl]-oxime (173)

Yield: (60% of the theoretical value) MS: M/e=622.0; $\lambda_{max}$: 500.0 nm.

Example 174

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[3-(4-(3-chlorophenyl)-piperazine-1-yl)propyl]-oxime (174)

Yield: (90% of the theoretical value) MS: M/e=787.1; $\lambda_{max}$: 500.0 nm.

Example 175

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[3-(dimethylamino)propyl]oxime (175)

Yield: (75% of the theoretical value) MS: M/e=636.1; $\lambda_{max}$: 500.0 nm.

Example 176

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydepyridine-2-yl-hydrazone (176)

Yield: (95% of the theoretical value) MS: M/e=670.9; $\lambda_{max}$: 500.0 nm.

Example 177

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde[4-(trifluoromethyl)pyrimidine-2-yl]hydrazone (177)

Yield: (95% of the theoretical value) MS: M/e=739.9; $\lambda_{max}$: 500.0 nm.

Example 178

(8S)-5-bromo-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]pyridyl-3-carbohydrazide (178)

Yield: (90% of the theoretical value) MS: M/e=699.0; $\lambda_{max}$: 500.0 nm.

Example 179

(8S)-5-bromo-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]isonicotinohydrazide (179)

Yield: (90% of the theoretical value) MS: M/e=699.0; $\lambda_{max}$: 500.0 nm.

Example 180

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-1,2,4-triazole-4-ylhydrazone (180)

Yield: (70% of the theoretical value) MS: M/e=645.9; $\lambda_{max}$: 492.0 nm.

Example 181

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-4,5-dihydro-1H-imidazole-2-ylhydrazone (181)

Yield: (95% of the theoretical value) MS: M/e=662.0; $\lambda_{max}$: 492.0 nm.

Example 182

(8S)-5-bromo-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-2-furohydrazide (182)

Yield: (95% of the theoretical value) MS: M/e=688.9; $\lambda_{max}$: 492.0 nm.

Example 183

(8S)-5-bromo-4-amino-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]benzohydrazide (183)

Yield: (95% of the theoretical value) MS: M/e=713.0; $\lambda_{max}$: 500.0 nm.

Example 184

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydethiosemicarbazone (184)

Yield: (95% of the theoretical value) MS: M/e=653.0; $\lambda_{max}$: 500.0 nm.

Example 185

(8S)-5-bromo-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]thiophene-2-carbohydrazide (185)

Yield: (95% of the theoretical value) MS: M/e=704.0; $\lambda_{max}$: 492.0 nm.

Example 186

(8S)-5-bromo-2-(1H-indole-3-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (186)

Yield: (95% of the theoretical value) MS: M/e=751.1; $\lambda_{max}$: 500.0 nm.

Example 187

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde(4-methylpiperazine-1-yl)hydrazone (187)

Yield: (95% of the theoretical value) MS: M/e=677.1; $\lambda_{max}$: 500.0 nm.

Example 188

(8S)-5-bromo-2-oxo-2-[(2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazino}acetamide (188)

Yield: (95% of the theoretical value) MS: M/e=665.0; $\lambda_{max}$: 500.0 nm.

Example 189

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-1,1',3',5',8'(2H)-pentone (189)

Yield: (95% of the theoretical value) MS: M/e=709.9; $\lambda_{max}$: 492.0 nm.

Example 190

(8S)-5-bromo-((2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazino)acetonitrile (190)

Yield: (95% of the theoretical value) MS: M/e=661.0; $\lambda_{max}$: 500.0 nm.

Example 191

(8S)-5-bromo-2-amino-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]benzohydrazide (191)

Yield: (70% of the theoretical value) MS: M/e=713.0; $\lambda_{max}$: 492.0 nm.

Example 192

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[2-morpholine-4-yl-ethyl)oxime (192)

Yield: (95% of the theoretical value) MS: M/e=708.0; $\lambda_{max}$: 500.0 nm.

Example 193

(8S)-5-bromo-(2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]hydrazinecarboximidamide (193)

Yield: (95% of the theoretical value) MS: M/e=636.0; $\lambda_{max}$: 500.0 nm.

Example 194

(8S)-5-bromo-2-(dimethylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (194)

Yield: (95% of the theoretical value) MS: M/e=679.0; $\lambda_{max}$: 500.0 nm.

Example 195

(8S)-5-bromo-1-[2-oxo-2-((2E)-2-{[(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylenelhydrazino)ethyl]pyridinium chloride (195)

Yield: (95% of the theoretical value) MS: M/e=713.0; $\lambda_{max}$: 500.0 nm.

Example 196

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-methyloxime (196)

Yield: (95% of the theoretical value) MS: M/e=609.0; $\lambda_{max}$: 492.0 nm.

Example 197

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-O-benzyloxime (197)

Yield: (95% of the theoretical value) MS: M/e=685.0; $\lambda_{max}$: 492.0 nm.

Example 198

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde oxime (198)

Yield: (95% of the theoretical value) MS: M/e=595.0; $\lambda_{max}$: 492.0 nm.

Example 199

(8S)-5-bromo-1-O-(((1E)-[(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene}amino)-β-D-glucopyranose (199)

Yield: (90% of the theoretical value) MS: M/e=757.0; $\lambda_{max}$: 500.0 nm.

Example 200

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde-phenylsemicarbazone (200)

Yield: (90% of the theoretical value) MS: M/e=713.0; $\lambda_{max;\ \lambda max}$:500.0 nm.

Example 201

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehydesemicarbazone (201)

Yield: (90% of the theoretical value) MS: M/e=637.0; $\lambda_{max}$: 492.0 nm.

Example 202

(8S)-5-bromo-2-piperidino-4-yl-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (201)

Yield: (90% of the theoretical value) MS: M/e=719.0; $\lambda_{max}$: 500.0 nm.

Example 203

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-chlorobenzyl)oxime (203)

Yield: (95% of the theoretical value) MS: M/e=718.0; $\lambda_{max}$: 492.0 nm.

Example 204

(8S)-5-bromo-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]-2-methyl-1,3-thiazole-4yl-carbohydrazide (204)

Yield: (95% of the theoretical value) MS: M/e=718.9; $\lambda_{max}$: 492.0 nm.

Example 205

(8S)-5-bromo-2-(1H-imidazole-1-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (205)

Yield: (95% of the theoretical value) MS: M/e=702.0; $\lambda_{max}$: 500.0 nm.

Example 206

(8S)-5-bromo-2-(acetylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (206)

Yield: (95% of the theoretical value) MS: M/e=693.0; $\lambda_{max}$: 492.0 nm.

Example 207

(8S)-5-bromo-2-(4-methylpiperazine-1-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (207)

Yield: (90% of the theoretical value) MS: M/e=734.1; $\lambda_{max}$: 500.0 nm.

Example 208

(8S)-5-bromo-2-morpholine-4-yl-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (208)

Yield: (95% of the theoretical value) MS: M/e=721.1; $\lambda_{max}$: 500.0 nm.

Example 209

(8S)-5-bromo-2-(methylamino)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (209)

Yield: (95% of the theoretical value) MS: M/e=665.0; $\lambda_{max}$: 500.0 nm.

Example 210

(8S)-5-bromo-2-[isopropyl(methyl)amino]-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (210)

Yield: (95% of the theoretical value) MS: M/e=707.0; $\lambda_{max}$: 500.0 nm.

Example 211

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[2-(dimethylamino)ethyl]oxime (211)

Yield: (95% of the theoretical value) MS: M/e=666.0; $\lambda_{max}$: 500.0 nm.

Example 212

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[3-(4-(3-chlorophenyl)-piperazine-1-yl)propyl]oxime (212)

Yield: (95% of the theoretical value) MS: M/e=831.0; $\lambda_{max}$: 500.0 nm.

Example 213

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[3-(dimethylamino)propyl]oxime (213)

Yield: (95% of the theoretical value) MS: M/e=680.0; $\lambda_{max}$: 492.0 nm.

Example 214

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-isopropyloxime (214)

Yield: (95% of the theoretical value) MS: M/e=559.2; $\lambda_{max}$: 500.0 nm.

Example 215

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-n-hexyloxime (215)

Yield: (99% of the theoretical value) MS: M/e=601.3; $\lambda_{max}$: 500.0 nm.

Example 216

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-fluorobenzyl)oxime (216)

Yield: (99% of the theoretical value) MS: M/e=625.2; $\lambda_{max}$: 500.0 nm.

Example 217

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-chlorobenzyl)oxime (217)

Yield: (99% of the theoretical value) MS: M/e=641.2; $\lambda_{max}$: 500.0 nm.

Example 218

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-fluorobenzyl)oxime (218)

Yield: (99% of the theoretical value) MS: M/e=625.3; $\lambda_{max}$: 500.0 mm.

Example 219

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-isopropyloxime (219)

Yield: (80% of the theoretical value) MS: M/e=593.2; $\lambda_{max}$: 500.0 nm.

Example 220

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-n-hexyloxime (220)

Yield: (90% of the theoretical value) MS: M/e=635.3; $\lambda_{max}$: 500.0 nm.

Example 221

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-fluorobenzyl)oxime (221)

Yield: (85% of the theoretical value) MS: M/e=659.3; $\lambda_{max}$: 500.0 nm.

Example 222

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-chlorobenzyl)oxime (222)

Yield: (80% of the theoretical value) MS: M/e=675.3; $\lambda_{max}$: 500.0 nm.

Example 223

(8S)-5-chloro-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-fluorobenzyl)oxime (223)

Yield: (80% of the theoretical value) MS: M/e=659.3; $\lambda_{max}$: 500.0 nm.

Example 224

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-isopropyloxime (224)

Yield: (90% of the theoretical value) MS: M/e=639.3; $\lambda_{max}$: 492.0 nm.

Example 225

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-n-hexyloxime (225)

Yield: (95% of the theoretical value) MS: M/e=679.3; $\lambda_{max}$: 492.0 nm.

Example 226

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-fluorobenzyl)oxime (226)

Yield: (95% of the theoretical value) MS: M/e=703.3; $\lambda_{max}$: 492.0 nm.

Example 227

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-chlorobenzyl)oxime (227)

Yield: (95% of the theoretical value) MS: M/e=719.3; $\lambda_{max}$: 492.0 nm.

Example 228

(8S)-5-bromo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-fluorobenzyl)oxime (228)

Yield: (95% of the theoretical value) MS: M/e=705.3; $\lambda_{max}$: 492.0 nm.

Example 229

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-isopropyloxime (229)

Yield: (99% of the theoretical value) MS: M/e=685.3; $\lambda_{max}$:500.0 nm.

Example 230

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-n-hexyloxime (230)

Yield: (99% of the theoretical value) MS: M/e=727.4; $\lambda_{max}$: 500.0 nm.

Example 231

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-fluorobenzyl)oxime (231)

Yield: (99% of the theoretical value) MS: M/e=751.3; $\lambda_{max}$: 500.0 nm.

Example 232

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(4-chlorobenzyl)oxime (232)

Yield: (99% of the theoretical value) MS: M/e=767.3; $\lambda_{max}$: 500.0 nm.

Example 233

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-fluorobenzyl)oxime (233)

Yield: (99% of the theoretical value) MS: M/e=751.3; $\lambda_{max}$: 500.0 nm.

Example 234

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-benzyloxime (234)

Yield: (99% of the theoretical value) MS: M/e=733.3; $\lambda_{max}$: 500.0 nm.

Example 235

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[2-morpholine-4-yl-ethyl)oxime (235)

Yield: (99% of the theoretical value) MS: M/e=756.3; $\lambda_{max}$: 500.0 nm.

Example 236

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-methyloxime (236)

Yield: (95% of the theoretical value) MS: M/e=657.3; $\lambda_{max}$: 492.0 nm.

Example 237

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-(3-chlorobenzyl)oxime (237)

Yield: (99% of the theoretical value) MS: M/e=767.3; $\lambda_{max; \lambda max}$:492.0 nm.

Example 238

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-[3-(4-(3-chlorophenyl)-piperazine-1-yl)propyl]oxime (238)

Yield: (99% of the theoretical value) MS: M/e=879.4; $\lambda_{max}$: 500.0 nm.

Example 239

(8S)-5-iodo-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde oxime (239)

Yield: (99% of the theoretical value) MS: M/e=643.3; $\lambda_{max}$: 492.0 nm.

Example 240

(8S)-5-iodo-2-(4-methylpiperazine-1-yl)-N'-[(1E)-(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene]acetohydrazide (240)

Yield: (99% of the theoretical value) MS: M/e=782.3; $\lambda_{max}$: 500.0 nm.

Example 241

(8S)-5-iodo-2-morpholine-4-yl-N'-[(1E)-(4',9,9'-trihydroxy-6'-methoxy-1,1',3',5',8'-pentaoxo-1,1',2,3', 5',6,7,8'-octahydrospiro[cyclopentag]isoquinoline-8, 2'-cyclopenta[b]-naphthalene]-3-yl)methylene] acetohydrazide (241)

Yield: (99% of the theoretical value) MS: M/e=782.3; $\lambda_{max}$: 500.0 nm.

Example 242

(8S)-5-iodo-2-oxo-2-{(2E)-2-[(4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl)methylene] hydrazino}acetamide (242)

Yield: (99% of the theoretical value) MS: M/e=713.3; $\lambda_{max}$: 500.0 nm.

Example 243

(8S)-4',9,9'-trihydroxy-6'-ethoxy-3-[(1E,3E)-penta-1, 3-dienyl]-6,7-dihydrospiro[cyclopenta[g]isoquinoline-8,2'-cyclopenta[b]-naphthalene]-1,1'-3',5',8' (2H)-pentone (243)

Five (5) mg (0.0095 mmol) fredericamycin (1) are suspended in 2.0 ml ethanol. Under $N_2$ atmosphere, 90 mg sodium acetate are added and boiled under reflux. After a few minutes, the suspension turns into a deep blue solution. After 24 h it is cooled, transferred onto water and shaken out with ethyl acetate (0.1% $CF_3COOH$). After drying and concentration, a chromatographically homogenous, red powder is left.
Yield: 5.0 mg (97% of the theoretical value) MS=554 (M+H)+; $\lambda_{max}$: 504.0 nm.

Example 244

(8S)-4',9,9'-trihydroxy-6'-n-butoxy-3-[(1E,3E)-penta-1,3-dienyl]-6,7-dihydrospiro[cyclopenta[g] isoquinoline-8,2'-cyclopenta[b]-naphthalene]-1,1'-3', 5',8'(2H)-pentone (244)

Six (6) mg (0.0114 mmol) fredericamycin (1) are suspended in 3.0 ml n-butanol. Under $N_2$ atmosphere, 50 mg potassium acetate are added and heated to 100° C. After a few minutes, the suspension turns into a deep blue solution. The solution is left for 1 h at this temperature, and is then cooled. It is transferred onto water and shaken out with ethyl acetate (0.1% $CF_3COOH$). After drying and concentration, a chromatographically homogenous red powder is left.
Yield: 6.2 mg (96% of the theoretical value) MS=582 (M)+; $\lambda_{max}$: 500.0 nm.

Example 245

(8S)-4',9,9'-trihydroxy-6'-n-isopropyloxy-3-[(1E, 3E)-penta-1,3-dienyl]-6,7-dihydrospiro[cyclopenta [g]isoquinoline-8,2'-cyclopenta[b]-naphthalene]-1,1'-3',5',8'(2H)-pentone (245)

Five (5) mg (0.0095 mmol) fredericamycin (1) are suspended in 3.0 ml n-propanol. Under $N_2$ atmosphere, 50 mg potassium acetate (anhydrous) are added and heated to 80° C. After a few minutes, the suspension turns into a deep blue solution. The solution is left for 48 h at this temperature, and is then cooled. It is transferred onto water and shaken out with ethyl acetate (0.1% $CF_3COOH$). After drying and concentration, a chromatographically homogenous red powder is left.
Yield: 3.7 mg (70% of the theoretical value) MS=568 (M+H)+; $\lambda_{max}$: 500.0 nm.

Example 246

(8S)-4',9,9'-trihydroxy-6'-(2-dimethylaminoethoxy)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone (246)

6.1 mg (0.01159 mmol) fredericamycin (1) are suspended in 3.5 ml N,N-Dimethylaminoethanol. Under $N_2$ atmosphere, 52 mg anhydrous potassium acetate are added and heated to 80° C. After a few minutes, the suspension turns into a deep blue solution. The solution is left for 1.5 h at this temperature, and is then cooled. It is transferred onto water and shaken out with ethyl acetate (0.1% $CF_3COOH$). After drying and concentration, a chromatographically homogenous red powder is left.
Yield: 2.4 mg (36% of the theoretical value); MS=597 (M+H)+; $\lambda_{max}$: 504.0 nm.

Example 247

(8S)-5-bromo-4',9,9'-trihydroxy-6'-(2-dimethylaminoethoxy)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone (247)

Ten (10.0) mg (0.019 mmol) bromofredericamycin (14) are suspended in 3.0 ml ethanol. Under $N_2$ atmosphere, 50 mg anhydrous potassium acetate are added and heated to 80° C. After a few minutes, the suspension turns into a deep blue solution. The solution is left for 48 h at this temperature, and is then cooled. It is transferred onto water and shaken out with ethyl acetate (0.1% $CF_3COOH$). After drying and concentration, a chromatographically homogenous red powder is left.
Yield: 7.2 mg (71% of the theoretical value); MS=632/634 (M+H)+; $\lambda_{max}$: 504.0 nm.

Example 248

(8S)-4',9,9'-trihydroxy-6'-allyloxy-3-[(1E,3E)-penta-1,3-dienyl]-6,7-dihydrospiro[cyclopenta[g]isoquinoline-8,2'-cyclopenta[b]-naphthalene]-1,1'-3',5',8' (2H)-pentone (248)

9.6 mg (0.01824 mmol) fredericamycin (1) are suspended in 3.0 ml allyl alcohol. Under $N_2$ atmosphere, 58 mg anhydrous potassium acetate are added and heated to 70° C. After a few minutes, the suspension turns into a deep blue solution. The solution is left for 2.5 h at this temperature, and is then cooled. It is transferred onto water and shaken out with ethyl acetate (0.1% $CF_3COOH$). After drying and concentration, a chromatographically homogenous red powder is left.
Yield: 9.2 mg (91% of the theoretical value); MS=566 (M+H)+; $\lambda_{max}$: 500.0 nm.

The compounds 249, 250, 251, 252, 253, 254, 255 were generated analogously to the instructions 244-248:

Example 249

(8S)-4',9,9'-trihydroxy-6'-(2-hydroxyethoxy)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone (249)

Yield: 5.2 mg (52% of the theoretical value); MS=569 (M)+; $\lambda_{max}$: 499.0 nm.

Example 250

(8S)-4',9,9'-trihydroxy-6'-benzyloxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone (250)

Yield: 10.2 mg (99% of the theoretical value); MS=616 (M+H)+; $\lambda_{max}$: 504.0 nm.

Example 251

(8S)-4',9,9'-trihydroxy-6'-cyclopropylmethoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone (251)

Yield: 12.9 mg (99% of the theoretical value); MS=580 (M)+; $\lambda_{max}$:500.0 nm.

Example 252

1-Desoxy-5-C-[(8R)-4',9,9'-trihydroxy-6'-ethoxy-1,1',3',5',8'-pentaoxo-1,1',2,3',5',6',7',8'-octahydrospiro[cyclopenta[g]isoquinoline-8,2'-cyclopenta[b]-naphthalene]-3-yl]pentitol (252)

Yield: 2.0 mg (20% of the theoretical value); MS=622 (M+H)+; $\lambda_{max}$: 499.0 nm.

Example 253

(8S)-4',9,9'-trihydroxy-6'-(2-t-butoxycarbonylaminoethoxy)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone (253)

Yield: 12.9 mg (99% of the theoretical value); MS=669 (M)+; $\lambda_{max}$: 500.0 mm.

Example 254

(8S)-4',9,9'-trihydroxy-6'-(2-N,N-diisopropylaminoethoxy)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone (249)

Yield: 5.8 mg (48% of the theoretical value); MS=653 (M+H)+; $\lambda_{max}$: 500.0 nm.

Example 255

1-Desoxy-5-C-[(8R)-4',9,9'-trihydroxy-6'-ethoxy-1,1',3',5',8'-pentaoxo-1,1',2,3',5',6,7,8'-octahydrospiro[cyclopenta[g]isoquinoline-8,2'-cyclopenta[b]-naphthalene)-3-yl]pentitol (255)

Yield: 5.5 mg (50% of the theoretical value); MS=594 (M+H)+; $\lambda_{max}$: 500.0 nm.

Example 256

(8S)-4',9,9'-trihydroxy-6'-(2-bromoethoxy)-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (256)

10.6 mg (0.02014 mmol) fredericamycin (1) are suspended in 2.0 ml bromoethanol. Under $N_2$ atmosphere, 150 mg anhydrous potassium acetate are added and heated to 120° C. After a few minutes, the suspension turns into a deep blue solution. After 12 hours, addition of another 150 mg potassium acetate. The solution is left for another 12 h at this temperature, and is then cooled. It is transferred onto water and shaken out with ethyl acetate (0.1% $CF_3COOH$). After drying and concentration, a chromatographically homogenous red powder is left.
Yield: 11.5 mg (99% of the theoretical value); MS=632/634 (M+H)+; $\lambda_{max}$: 499.0 nm.

Example 257

(8S)-5-iodo-4',9,9'-trihydroxy-6'-cyclopropylamino-3-[(1E,3E)-penta-1,3-dienyl]-6,7-dihydrospiro[cyclopent[g]isoquinoline-8,2'-cyclopenta[b]-naphthalene]-1,1'-3',5',8'(2H)-pentone (257)

Five (5.0) mg (7.5 µmol) 5-iodofredericamycin (15) are dissolved under argon in 1.0 ml anhydrous DMF. After addition of 0.64 mg (11.2 µmmol) cyclopropylamine, it is stirred at room temperature for 3 h. Excess cycloprolylamine and DMF are removed at high vacuum. After drying and concentration, a chromatographically homogenous red powder is left.
Yield: 5.1 mg (99%); MS=691.3 (M+H)+; $\lambda_{max}$: 504.0 nm.

Example 258

(8S)-5-iodo-4',9,9'-trihydroxy-6'-n-butylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (258)

Five (5.0) mg (7.5 µmol) 5-iodofredericamycin (15) are dissolved under argon in 1.0 ml anhydrous DMF. After addition of 0.82 mg (11.2 µmmol) n-butylamine, it is stirred at room temperature for 20 h. Excess n-butylamine and DMF are removed at high vacuum. After drying and concentration, a chromatographically homogenous red powder is left.
Yield: 5.3 mg (99%); MS=707.3 (M+H)+; $\lambda_{max}$: 504.0 nm.

Example 259

(8S)-5-bromo-4',9,9'-trihydroxy-6'-n-butylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (259)

Five (5.0) mg (8.1 µmol) 5-bromofredericamycin (15) are dissolved under argon in 1.0 ml anhydrous DMF. After addi-

Example 260

(8S)-4',9,9'-trihydroxy-6'-cyclopropylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (260)

Five (5.0) mg (9.3 µmol) fredericamycin (1) are dissolved under argon in 1.0 ml anhydrous DMF. After addition of 2.12 mg (37.2 µmmol) cyclopropylamine, it is stirred at room temperature for 2 h. Excess cyclopropylamine and DMF are removed at high vacuum. After drying and concentration, a chromatographically homogenous red powder is left.

Yield: 5.1 mg (99%); MS=565.4 (M+H)+; $\lambda_{max}$: 510.0 nm.

Example 261

(8S)-4',9,9'-trihydroxy-6'-anilino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (261)

Five (5.0) mg (9.3 µmol) fredericamycin (1) are dissolved under argon in 1.0 ml anhydrous DMF. After addition of 3.46 mg (37.2 µmmol) aniline and 37.2 µg stannous(IV)chloride (1.0 M in CH$_2$Cl$_2$), it is heated to 60° C. The reaction mixture is stirred for 24 h, and then excess diethanolaminomethyl polystyrene resin is added. Stir for 1 h. Exhaust off the resin and wash with DMF. The organic phase is concentrated at high vacuum. A chromatographically homogenous red powder is left.

Yield: 5.5 mg (99%); MS=601.1 (M+H)+; $\lambda_{max}$: 504.0 nm.

Example 262

(8S)-4',9,9'-trihydroxy-6'-piperidino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (262)

Five (5.0) mg (9.3 µmol) fredericamycin (1) are dissolved under argon in 1.0 ml anhydrous DMF. After addition of 3.16 mg (37.2 µmmol) piperidine, it is stirred for 22 h at room temperature. Excess amine and DMF are removed in high vacuum. A chromatographically homogenous red powder is left.

Yield: 5.5 mg (99%); MS=593.4 (M+H)+; $\lambda_{max}$: 504.0 nm.

Example 263

(8S)-4',9,9'-trihydroxy-6'-dimethylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (263)

Five (5.0) mg (9.3 µmol) fredericamycin (1) are dissolved under argon in 1.0 ml anhydrous DMF. After addition of 1.67 mg (37.2 µmmol) dimethylamine (2M in MeOH), it is stirred for 4 h at room temperature. Excess amine and DMF are removed in high vacuum. A chromatographically homogenous red powder is left.

Yield: 5.5 mg (99%); MS=553.6 (M+H)+; $\lambda_{max}$: 526.0 nm.

Example 264

(8S)-4',9,9'-trihydroxy-6'-isopropylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (264)

Five (5.0) mg (9.3 µmol) fredericamycin (1) are dissolved under argon in 1.0 ml anhydrous DMF. After addition of 2.19 mg (37.2 µmmol) isopropylamine, it is stirred for 4 h at room temperature. Excess amine and DMF are removed in high vacuum. A chromatographically homogenous red powder is left.

Yield: 5.2 mg (99%); MS=567.3 (M+H)+; $\lambda_{max}$: 504.0 nm.

Example 265

(8S)-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (265)

Five (5.0) mg (9.3 µmol) fredericamycin (1) are dissolved under argon in 1.0 ml anhydrous DMF. After addition of 0.34 mg (11.1 µmmol) methylamine (2M in CH$_3$OH), it is stirred for 19 h at room temperature. Excess amine and DMF are removed in high vacuum. A chromatographically homogenous red powder is left.

Yield: 5.0 mg (99%); MS=539.2 (M+H)+; $\lambda_{max}$: 504.0 nm.

Example 266

(8S)-5-iodo-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (266)

Five (5.0) mg (7.5 µmol) 5-iodofredericamycin (1) are dissolved under argon in 1.0 ml anhydrous DMF. After addition of 0.28 mg (9.0 µmmol) methylamine (2M in CH$_3$OH), it is stirred for 2 h at room temperature. Excess amine and DMF are removed in high vacuum. A chromatographically homogenous red powder is left.

Yield: 5.0 mg (99%); MS=665.2 (M+H)+; $\lambda_{max}$: 492.0 nm.

Example 267

(8S)-4',9,9'-trihydroxy-6'-morpholino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (267)

Five (5.0) mg (9.3 µmol) fredericamycin (1) are dissolved under argon in 1.0 ml anhydrous DMF. After addition of 3.24 mg (37.2 µmmol) morpholine, it is stirred for 18 h at room temperature. Excess amine and DMF are removed in high vacuum. A chromatographically homogenous red powder is left.

Yield: 5.5 mg (99%); MS=595.5 (M+H)+; $\lambda_{max}$: 518.0 nm.

--- tion of 0.89 mg (12.2 µmmol) n-butylamine, it is stirred at room temperature for 20 h. Excess n-butylamine and DMF are removed at high vacuum. After drying and concentration, a chromatographically homogenous red powder is left.

Yield: 5.3 mg (99%); MS=659.4/661.4 (M+H)+; $\lambda_{max}$: 504.0 nm.

Example 268

(8S)-4',9,9'-trihydroxy-6'-amino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (268)

Five (5.0) mg (9.3 µmol) fredericamycin (1) are dissolved under argon in 1.0 ml anhydrous DMF. After addition of 0.67 mg (37.2 µmmol) ammonia (2M in EtOH), it is stirred for 24 h at room temperature. Excess ammonia and DMF are removed in high vacuum. A chromatographically homogenous red powder is left.

Yield: 4.8 mg (99%); MS=525.4 (M+H)+; $\lambda_{max}$: 504.0 nm.

Example 269

(8S)-4',9,9'-trihydroxy-6'-pyrrolidino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (269)

Five (5.0) mg (9.3 µmol) fredericamycin (1) are dissolved under argon in 1.0 ml anhydrous DMF. After addition of 0.99 mg (13.9 µmmol) pyrrolidine, it is stirred for 19 h at room temperature. Excess amine and DMF are removed in high vacuum. A chromatographically homogenous red powder is left.

Yield: 5.3 mg (99%); MS=579.2 (M+H)+; $\lambda_{max}$: 554.0 nm.

Example 270

(8S)-5-bromo-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-1,1'-3',5',8'(2H)-pentone (270)

Five (5.0) mg (8.1 µmol) 5-bromofredericamycin (1) are dissolved under argon in 1.0 ml anhydrous DMF. After addition of 0.70 mg (12.2 µmmol) cyclopropylamine, it is stirred for 5 h at room temperature. Excess cyclopropylamine and DMF are removed in high vacuum. A chromatographically homogenous red powder is left.

Yield: 5.0 mg (99%); MS=643.4/645.4 (M+H)+; $\lambda_{max}$: 492.0 nmn.

Example 271

2-[Acetyl]-3-[(8S)-4',9,9'-trihydroxy-6'-methylamino-3-[(1E,3E)-penta-1,3-dienyl]-6,7-dihydrospiro[cyclopent[g]isoquinoline-8,2'-cyclopenta[b]-naphthalene]-3-yl]ethene (271)

79.5 mg (479 µmol) (2-oxo-propyl)-phosphonic acid dimethylester are dissolved under argon in 8 ml absolute pyridine, and 60.2 µl (479 µmol) 1,1,3,3-tetramethylguanidine are added at 0° C. After 5 minutes, 80.0 mg (159.7 µmol) fredericamycin aldehyde (4) is added at 0° C. After 2 hours, 100 ml 1 M hydrochloric acid are added, and the supernatant is sucked off from the precipitate. Dry under high vacuum.

Yield: 60.0 mg (69% of the theoretical value); M/e=542.2; $\lambda_{max}$: 492.0 nm.

Example 272

2-[Bromoacetyl]-3-[(8S)-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-3-yl]ethene (272)

Fifty (50.0) mg (92.4 µmol) acetyl fredericamycin are dissolved under argon in 5 ml absolute DMF, and then 36.9 mg (231.1 µmol) bromine as a 1 M bromine solution in DMF are added under exclusion of light. It is stirred for 23 h under exclusion of light, and then 100 ml water are added. The precipitate is sucked off and dried under high vacuum.

Yield: 57.0 mg (87% of the theoretical value) red powder; M/e=697.9/699.9/701.9; M+; $\lambda_{max}$: 504.0 nm.

Example 273

2-[2-Amino-thiazole-4-yl]-3-[(8S)-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-3-yl]ethene (273)

Twenty (20.0) mg (28.7 µmol) bromoacetyl fredericamycin (273) are dissolved under argon in 4 ml absolute DMF. At room temperature, first 3.3 mg (43.0 µmol) thiourea, and then 20 mg IR120H+ are added. After 2 hours, it is filtered off the resin, and added to 50 ml water. The precipitate is dried under high vacuum. Red powder.

Yield: 18.0 mg (93% of the theoretical value); M/e=676.1/678.1; (M+H); $\lambda_{max}$: 492.0 nm.

Example 274

2-[2-Phenyl-thiazole-4-yl]-3-[(8S)-4',9,9'-trihydroxy-6'-methylamino-3-[(1E,3E)-penta-1,3-dienyl]-6,7-dihydrospiro[cyclopenta[g]isoquinoline-8,2'-cyclopenta[b]-naphthalene]-3-yl]ethene (274)

Five (5.0) mg (7.2 µmol) bromoacetyl fredericamycin (273) are dissolved under argon in 1 ml absolute DMF. At room temperature, first 1.5 mg (10.8 µmol) thiobenzamide, and then 5 mg IR120H+ are added. After 3.5 h, addition of hydrazinosulfonyl resin, and stirring for 2 h. It is filtered off the resin, and added to 10 ml water. The precipitate is dried under high vacuum. Red powder.

Yield: 3.0 mg (57% of the theoretical value); M/e=737.2/739.2; (M+H); $\lambda_{max}$: 492.0 nm.

Example 275

2-[2-Acetylamino-thiazole-4-yl]-3-[(8S)-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-3-yl]ethene (275)

Five (5.0) mg (7.2 µmol) bromoacetyl fredericamycin (273) are dissolved under argon in 1 ml absolute DMF. At room temperature, first 1.3 mg (10.8 µmol) acetylthiourea, and then 5 mg IR120H+ are added. After 22 h, addition of hydrazinosulfonyl resin, and stirring for 2 h. It is filtered off the resin, and added to 10 ml water. The precipitate is dried under high vacuum. Red powder.

Yield: 2.0 mg (39% of the theoretical value); M/e=718.3/720.4; (M+H); $\lambda_{max}$: 492.0 nm.

Example 276

2-[2-Methyl-thiazole-4-yl]-3-[(8S)-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-3-yl]ethene (276)

Five (5.0) mg (7.2 µmol) bromoacetyl fredericamycin (273) are dissolved under argon in 1 ml absolute DMF. At room temperature, first 0.81 mg (10.8 µmol) thioacetamide, and then 5 mg IR120H+ are added. After 2 h, addition of hydrazinosulfonyl resin, and stirring for 2 h. It is filtered off the resin, and added to 10 ml water. The precipitate is dried at high vacuum. Red powder.
Yield: 3.0 mg (62% of the theoretical value); M/e=675.2/677.2; (M+H); $\lambda_{max}$: 492.0 nm.

Example 277

(8S)-4',9,9'-trihydroxy-6'-methylamino-3-[(1E,3E)-penta-1,3-dienyl]-6,7-dihydrospiro[cyclopentag]isoquinoline-8,2'-cyclopenta[b]-naphthalene]-1-thio-1,1'-3',5',8'(2H)-tetrone-thiofredericamycin (277)

Ten (10.0) mg (18.5 µmol) fredericamycin (1) are dissolved under argon in 2 ml absolute pyridine. After addition of 20.5 mg (92.5 mmol) phosphorous-V-sulfide, it is heated for 12 h to 60° C. Addition of another 20.5 mg (92.5 mmol) phosphorous-V-sulfide. According to HPLC (acetonitrile/water $CF_3COOH$), the reaction was complete after 1 h. It is transferred onto water and shaken out with ethyl acetate. Dry and concentrate. Purple-red powder.
Yield: 5.0 mg (49% of the theoretical value); M/e=55.7; (M+H); $\lambda_{max}$: 504.0 nm.

Example A

Water Solubility of the Fredericamycin Derivatives

The water solubility of the various fredericamycin derivatives can be determined in a 0.9% NaCl solution with a pH of 7.
The compounds (22) and (3) dissolve very well. Compound (6) dissolves well, and compounds (2), (10), and (13) are soluble. Compounds (5), (7), (11) and (12) are sufficiently and markedly better soluble than fredericamycin (compound (1)).

The invention claimed is:
1. A compound according to the general formula Ia or Ib:

wherein in each
R1 means H,
R3 means H, F, Cl, Br, or I and
R2 means $(CH_2)_rCH=N-NHCO-R23$, $(CH_2)_rCH=N-NHC(O)NH-R23$, $(CH_2)_rCH=N-NHC(S)NH-R23$, $(CH_2)_rCH=N-NHC(NH)NH-R23$, $(CH_2)_rCH=N-NHC(NH)-R23$, $(CH_2)_rCH=N-NHCO-CH_2NHCOR21$, $(CH_2)_rCH=N-NHCS-R23$, $(CH_2)_rCH=N-NR21R22$, $(CH_2)_rCH=N-N-(C_3NX'R211R212R213R214)$, $-(CH_2)_rCH=N-NHSO_2$ aryl, or $-(CH_2)_rCH=N-NHSO_2$ heteroaryl, with r=0, 1, 2, 3, 4, 5, wherein X'=NR215, O, or S, and R211, R212, R213, R214, and R215 are independently H or $C_1$-$C_6$ alkyl,
R21, R22 are independently H, $C_1$-$C_{14}$ alkyl, $C_1$-$C_{14}$ alkanoyl, $C_1$-$C_6$ alkylhydroxy, $C_1$-$C_6$ alkoxy, $C_1$-$C_6$ alkylamino, $C_1$-$C_6$alkylamino-$C_1$-$C_6$ alkyl, $C_1$-$C_6$ alkylamino-di-$C_1$-$C_6$-alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, or R21 and R22, together with the N, form a ring with 4, 5, 6, 7, or 8 members, which may optionally contain still another heteroatom selected from the group N, O, and S,
R23 independently of R21, has the same meanings as R21, or $CH_2$-pyridinium salts, $CH_2$-tri-$C_1$-$C_6$ alkylammonium salts, $CONH_2$, $CSNH_2$, CN, or $CH_2CN$,
R24 independently of R21, has the same meanings as R21, or H, CN, $COCH_3$, COOH, COOR21, CONR21R22, $NH_2$, or NHCOR21,
R25 independently of R21, has the same meanings as R21, or H, CN, $COCH_3$, COOH, COOR21, CONR21R22, $NH_2$, or NHCOR21,
R24, R25 together with the N, form a ring with 4, 5, 6, 7, or 8 members, which may optionally contain still another heteroatom selected from the group N, O, and S,
R31, R32 are independently $C_1$-$C_6$ alkyl, or R31 and R32, together with the N, form a ring with 4, 5, 6, 7, or 8 members, which may optionally contain still another heteroatom selected from the group N, O, and S,
R5 means $C_1$-$C_{20}$ alkyl,
R4, R6, R7 independently mean H,
R41 independently from R21, has the same meanings as R21, X means O, Y means O, S, NR9, wherein R9 may be H or $C_1$-$C_6$ alkyl,
as well their stereoisomers, tautomers, and their physiologically tolerable salts,
wherein heterocycloalkyl by itself or as part of another substituent means a group selected from the group consisting of pyrrolidine, piperidine, morpholine,

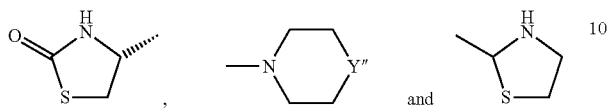

wherein Y" means $CH_2$, S, O, NH, or $NC_1$-$C_6$ alkyl, and
wherein heteroaryl by itself or as part of another substituent means a ring system selected from the group consisting of

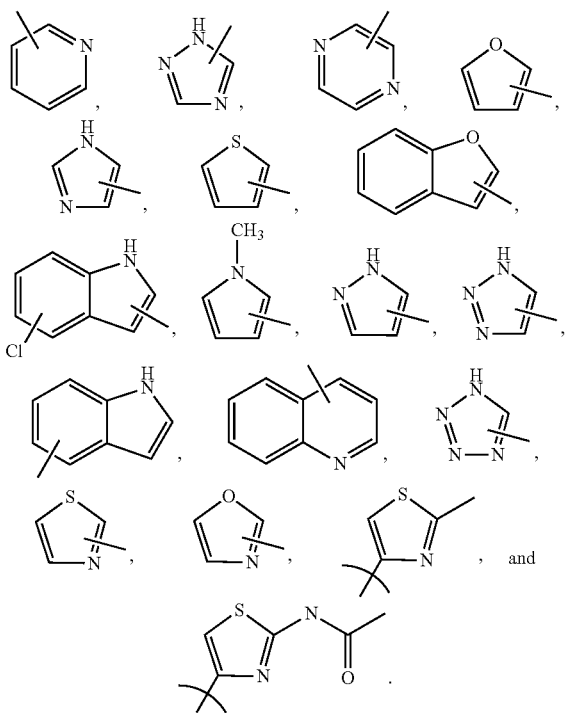

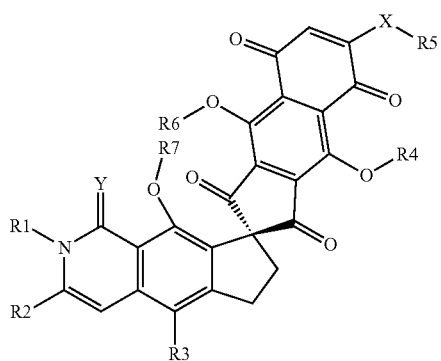

2. The compound according to claim 1, wherein Formula Ia or Ib adopts the stereochemistry of Formula IIa or IIb

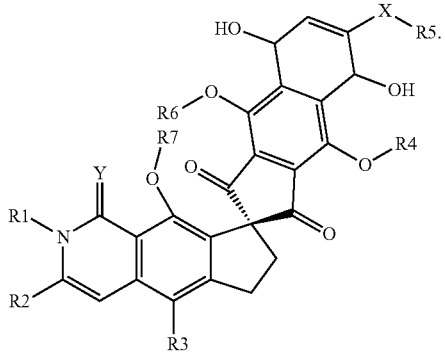

3. The compound according to claim 1, wherein R3 means F, Cl, Br, or I.

4. The compound according to claim 1, wherein R3 means $(CH_2)_r$CH=N—NHCO—R23, $(CH_2)_r$CH=N—NHC(O)NH—R23, $(CH_2)_r$CH=N—NHC(S)NH—R23, $(CH_2)_r$CH=N—NHC(NH)NH—R23, $(CH_2)_r$CH=N—NHC(NH)—R23, $(CH_2)_r$CH=N—NHCO—$CH_2$NHCOR21, $(CH_2)_r$CH=N—NHCS—R23, $(CH_2)_r$CH=N—NR21R22,

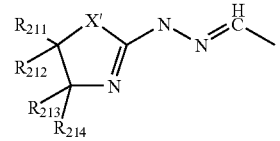

$(CH_2)_r$CH=N—N—($C_3$NX'R211R212R213R214), $(CH_2)_r$CH=N—$NHSO_2$ aryl, or $(CH_2)_r$CH=N—$NHSO_2$ heteroaryl, with r=0, 1, 2, 3, 4, 5, wherein X'=NR215, O, or S, and R211, R212, R213, R214, and R215 are independently H or $C_1$-$C_6$ alkyl.

5. The compound according to claim 1, wherein
R1 means H,
R2 means CH=N—NR21R22,

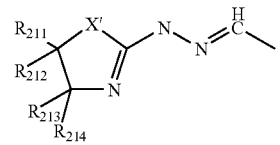

—CH=N—$NHSO_2$ aryl, —CH=N—$NHSO_2$ heteroaryl, or CH=N—NHCO—R23, wherein X'=NR215, O, or S, and R211, R212, R213, R214, and R215 are independently H or $C_1$-$C_6$ alkyl, R21, R22 independently mean $C_1$-$C_6$ alkyl, cycloalkyl, aryl, $C_1$-$C_4$ alkylaryl, heteroaryl, or $C_1$-$C_4$ alkylheteroaryl, R23 independently of R21, has the same meanings as R21, or $CH_2$-pyridinium salts, or $CH_2$-tri-$C_1$-$C_6$ alkylammonium salts, R24 independently of R21, has the same meanings as R21, or H, CN, $COCH_3$, COOH, COOR21, CONR21R22, $NH_2$, or NHCOR21, R25 independently of R21, has the same meanings as R21, or H, CN, $COCH_3$, COOH, COOR21, CONR21R22, $NH_2$, or NHCOR21, R24, R25 together mean $C_4$-$C_8$ cycloalkyl,
R3 means F, Cl, Br, or I,
R31 independently means $C_1$-$C_6$ alkyl, R5 means $C_1$-$C_6$ alkyl,
R4, R6, R7 independently mean H,
R41 independently from R21, has the same meanings as R21,
X means O,
Y means O, or S.

6. A composition comprising a compound according to claim 1, a carrier and adjuvants.

7. A method of treating cancer in a patient comprising administering an effective amount of a compound of claim 1 to said patient wherein said cancer is melanoma or a tumor selected from the group consisting of lung, breast, renal, uterine and prostate tumors.

8. The compound according to claim 1, wherein R3 is H, and R2 is CH=N—NHCO—R23, —CH=N—NR21R22,

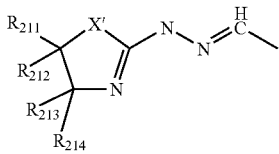

or CH=N—NHCO—R23, wherein X'=NR215, O, or S, and R211, R212, R213, R214, and R215 are independently H or $C_1$-$C_6$ alkyl.

9. The compound of claim 1, wherein
R3 is H and
R2 is —(CH$_2$)$_r$CH=N—NHCO—R23, —(CH$_2$)$_r$CH=N—NR21R22, —(CH$_2$)$_r$CH=N—NHC(S)NHR23, —(CH$_2$)$_r$CH=N—NHC(NH)NH—R23, or —(CH$_2$)$_r$CH=N—NHC(O)NH—R23.

10. The compound of claim 9, wherein X is O; Y is O; R5 is $C_1$-$C_{20}$ alkyl, and R4, R6, and R7 are each independently H.

11. The compound of claim 1, wherein
R3 is Cl, Br or I; and
R2 is (CH$_2$)$_r$CH=CN—NR21R22, (CH$_2$)$_r$CH=N—NHCO—R23, (CH$_2$)$_r$C=N—NHC(S)NH—R23, (CH$_2$)$_r$CH=N—NHC(NH)NH—R23, (CH$_2$)$_r$CH=N—NHC(O)NH—R23, (CH$_2$)$_r$CH=NR21, or (CH$_2$)$_r$CH=N—NHCO—CH$_2$NHCOR21.

12. The compound of claim 11, wherein X is O; Y is O; R5 is $C_1$-$C_{20}$ alkyl, and R4, R6, and R7 are each independently H.

* * * * *